United States Patent
Wigley et al.

(10) Patent No.: US 10,602,744 B2
(45) Date of Patent: Mar. 31, 2020

(54) AGRICULTURALLY BENEFICIAL MICROBES, MICROBIAL COMPOSITIONS, AND CONSORTIA

(71) Applicant: BIOCONSORTIA, INC., Davis, CA (US)

(72) Inventors: Peter Wigley, Auckland (NZ); Susan Turner, Davis, CA (US); Caroline George, Auckland (NZ); Thomas Williams, Davis, CA (US); Kelly Roberts, Davis, CA (US); Graham Hymus, Davis, CA (US); Kelvin Lau, Auckland (NZ)

(*) Notice: Subject to any disclaimer, the term of this patent is extended or adjusted under 35 U.S.C. 154(b) by 0 days.

(21) Appl. No.: 15/549,815

(22) PCT Filed: Feb. 9, 2016

(86) PCT No.: PCT/US2016/017204
§ 371 (c)(1),
(2) Date: Aug. 9, 2017

(87) PCT Pub. No.: WO2016/130586
PCT Pub. Date: Aug. 18, 2016

(65) Prior Publication Data
US 2018/0020671 A1    Jan. 25, 2018

Related U.S. Application Data

(60) Provisional application No. 62/113,792, filed on Feb. 9, 2015, provisional application No. 62/165,620, filed on May 22, 2015, provisional application No. 62/280,503, filed on Jan. 19, 2016.

(51) Int. Cl.
| | |
|---|---|
| *A01N 63/02* | (2006.01) |
| *A01N 63/00* | (2020.01) |
| *C12N 1/20* | (2006.01) |
| *C12R 1/01* | (2006.01) |
| *C12R 1/41* | (2006.01) |
| *C12R 1/38* | (2006.01) |
| *C12R 1/07* | (2006.01) |

(52) U.S. Cl.
CPC ............. *A01N 63/00* (2013.01); *A01N 63/02* (2013.01); *C12N 1/20* (2013.01); *C12R 1/01* (2013.01); *C12R 1/07* (2013.01); *C12R 1/38* (2013.01); *C12R 1/41* (2013.01)

(58) Field of Classification Search
None
See application file for complete search history.

(56) References Cited

U.S. PATENT DOCUMENTS 9,615,584 B2 *  4/2017  Reddy .................... C05F 11/08

FOREIGN PATENT DOCUMENTS

WO    WO 2014/210372 A1    12/2014

OTHER PUBLICATIONS

Zhang et al. International Journal of Systematic and Evolutionary Microbiology (2012), vol. 62, pp. 2731-2736.*
Choi, et al., "*Acidovorax soli* sp. Nov., isolated from landfill soil," *Int. J. Syst. Evol. Microbiol.* 60:2715-2718 (Dec. 2010).
International Search Report and Written Opinion for International Application No. PCT/US2016/017204, dated Aug. 10, 2016 (13 pages).
Li, "Phenotypic variation and molecular signaling in the interaction of the rhizosphere bacteria *Acidovorax* sp. N35 and Rhizobium radiobacter F4 with roots," Dissertation, LMU Munchen: Faculty of Biology, retrieved 20, 2016 from https://edoc.ub.uni-muenchen.de/12657, Abstract (Feb. 10, 2011).

* cited by examiner

*Primary Examiner* — Medina A Ibrahim
(74) *Attorney, Agent, or Firm* — Barnes & Thornburg LLP; Ryan L. Marshall; Jonathan Hartley

(57) ABSTRACT

The disclosure relates to isolated microorganisms-including novel strains of the microorganisms-microbial consortia, and agricultural compositions comprising the same. Furthermore, the disclosure teaches methods of utilizing the described microorganisms, microbial consortia, and agricultural compositions comprising the same, in methods for imparting beneficial properties to target plant species. In particular aspects, the disclosure provides methods of increasing desirable plant traits in agronomically important crop species.

4 Claims, 11 Drawing Sheets

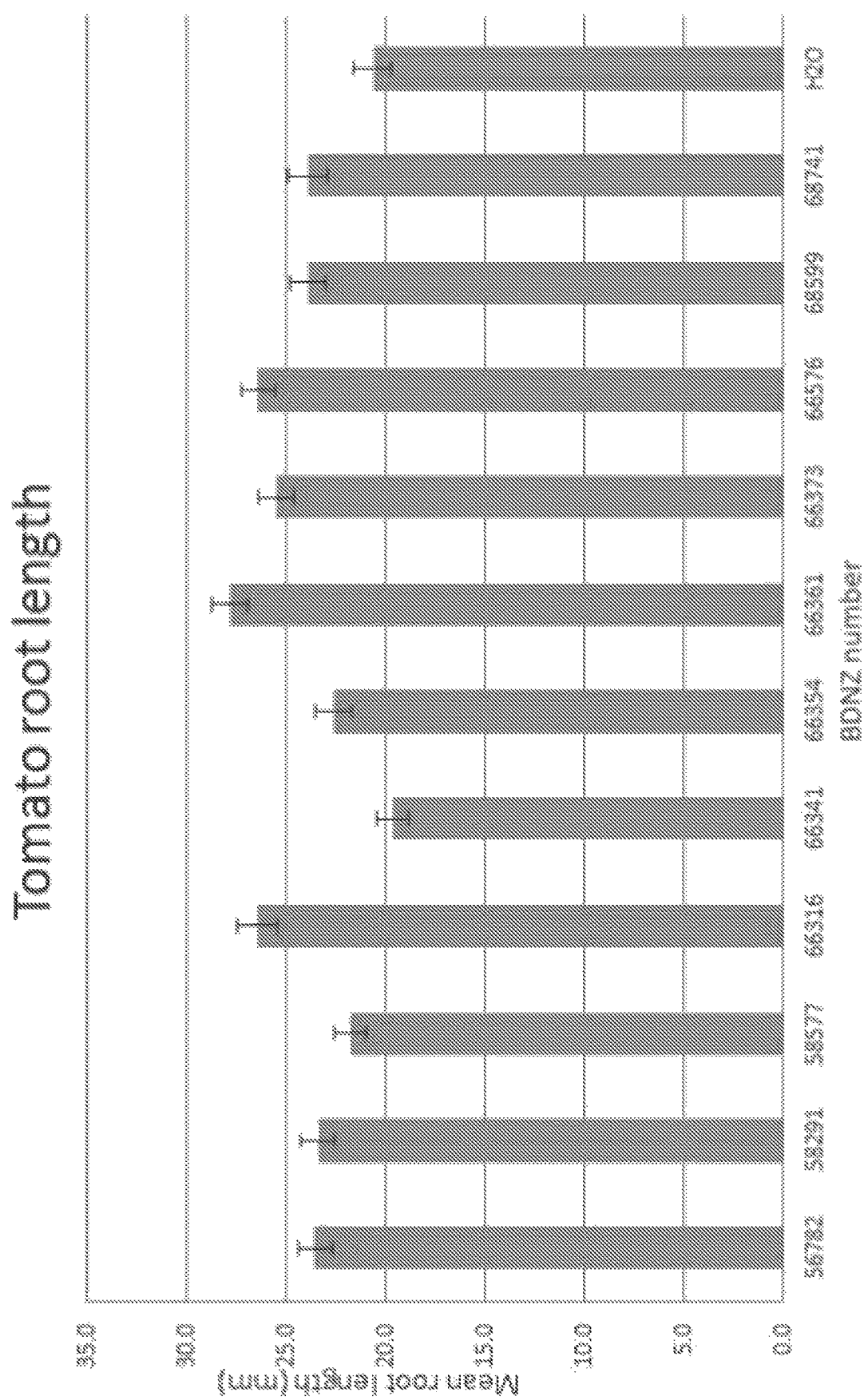

AGRICULTURALLY BENEFICIAL MICROBES, MICROBIAL COMPOSITIONS, AND CONSORTIA

CROSS REFERENCE TO RELATED APPLICATIONS

This application is a 371 national phase of PCT/US2016/017204, filed Feb. 9, 2016, and claims the benefit under 35 U.S.C. § 119(e) to U.S. Provisional Patent Application No. 62/113,792, filed on Feb. 9, 2015, and U.S. Provisional Patent Application No. 62/165,620, filed on May 22, 2015, and U.S. Provisional Patent Application No. 62/280,503, filed on Jan. 19, 2016, each of which is hereby incorporated by reference in its entirety for all purposes.

FIELD

The present disclosure relates to isolated and biologically pure microorganisms that have application, inter cilia, in agriculture. The disclosed microorganisms can be utilized in their isolated and biologically pure states, as well as being formulated into agriculturally acceptable compositions. Further, the disclosure provides agriculturally beneficial microbial consortia, containing at least two members of the disclosed microorganisms, as well as methods of utilizing said consortia in agricultural applications.

BACKGROUND

According to the United Nations World Food Program, there are close to 900 million malnourished people in the world. The malnourishment epidemic is particularly striking in the developing nations of the world, where one in six children is underweight. The paucity of available food can be attributed to many socioeconomic factors; however, regardless of ultimate cause, the fact remains that there is a shortage of food available to feed a growing world population, which is expected to reach 9 billion people by 2050. The United Nations estimates that agricultural yields must increase by 70-100% to teed the projected global population in 2050.

These startling world population and malnutrition figures highlight the importance of agricultural efficiency and productivity, in sustaining the world's growing population. The technological advancements achieved by modern row crop agriculture, which has led to never before seen crop yields, are impressive. However, despite the advancements made by technological innovations such as genetically engineered crops and new novel pesticidal and herbicidal compounds, there is a need for improved crop performance, in order to meet the demands of an exponentially increasing global population.

Scientists have estimated that if the global agricultural "yield gap" (which is the difference between the best observed yield and results elsewhere) could be closed, then worldwide crop production would rise by 45-70%. That is, if all farmers, regardless of worldwide location, could achieve the highest attainable yield expected for their respective regions, then a great majority of the deficiencies in worldwide food production could be addressed. However, solving the problem of how to achieve higher yields across a heterogenous worldwide landscape are difficult.

Often, yield gaps can be explained by inadequate water, substandard farming practices, inadequate fertilizers, and the non-availability of herbicides and pesticides. However, to vastly increase the worldwide use of water, fertilizers, herbicides, and pesticides, would not only be economically infeasible for most of the world, but would have negative environmental consequences.

Thus, meeting global agricultural yield expectations, by simply scaling up current high-input agricultural systems utilized in most of the developed world is simply not feasible.

There is therefore an urgent need in the art for improved methods of increasing crop performance and imparting beneficial traits to desired plant species.

SUMMARY OF THE DISCLOSURE

The present disclosure addresses this important issue of how to improve crop performance, thereby closing the worldwide yield gap, along with providing ways of imparting other beneficial traits to plant species.

The solution to increasing crop performance and increasing yield proffered by the present disclosure is not detrimental to the earth's resources, as it does not rely upon increased water consumption or increased input of synthetic chemicals into a system. Rather, the present disclosure utilizes microbes to impart beneficial properties, including increased yields, to desirable plants.

The disclosure therefore offers an environmentally sustainable solution that allows farmers to increase yields of important crops, which is not reliant upon increased utilization of synthetic herbicides and pesticides.

In embodiments, the disclosure provides for an efficient and broadly applicable agricultural platform utilizing microbes and microbial consortia that promote one or more desirable plant properties.

In some embodiments, a single microbe is utilized. In some aspects, the single microbe is isolated and purified. In some aspects, the single microbe is a taxonomic species of bacteria. In some aspects, the single microbe is an identifiable strain of a taxonomic species of bacteria. In some aspects, the single microbe is a novel, newly discovered strain of a taxonomic species of bacteria.

In some embodiments, a single microbe from Table 1 is utilized. In other embodiments, a single microbe from Table 2 is utilized. In yet other embodiments, a single microbe from Table 3 is utilized.

In some embodiments, a microbe from the genus *Bosea* is utilized.

In some aspects, the single microbe—whether a taxonomically identifiable species or strain—is combined with one or more other microbes of a different species or strain. In certain aspects, the combination of two or more microbes forms a consortia or consortium. The terms consortia and consortium are utilized interchangeably.

In certain aspects, the disclosure provides for the development of highly functional microbial consortia that help promote the development and expression of a desired phenotypic or genotypic plant trait. In some embodiments, the consortia of the present disclosure possess functional attributes that are not found in nature, when the individual microbes are living alone. That is, in various embodiments, the combination of particular microbial species into consortia, leads to the microbial combination possessing functional attributes that are not possessed by any one individual member of the consortia when considered alone.

In some embodiments, this functional attribute possessed by the microbial consortia is the ability to impart one or more beneficial properties to a plant species, for example: increased growth, increased yield, increased nitrogen utilization efficiency, increased stress tolerance, increased drought tolerance, increased photosynthetic rate, enhanced water use efficiency, increased pathogen resistance, modifications to plant architecture that don't necessarily impact plant yield, but rather address plant functionality, etc.

The ability to impart these beneficial properties upon a plant is not possessed, in some embodiments, by individual microbes as they would occur in nature. Rather, in some embodiments, it is by the hand of man combining these microbes into consortia that a functional composition is developed, said functional composition possessing attributes and functional properties that do not exist in nature.

However, in other embodiments, the disclosure provides for individual isolated and biologically pure microbes that are able to impart beneficial properties upon a desired plant species, without the need to combine said microbes into consortia.

In embodiments, the microbial consortia can be any combination of individual microbes from Table 1. In other embodiments, the microbial consortia can be any combination of individual microbes from Table 2. In yet other embodiments, the microbial consortia can be any combination of individual microbes from Table 3. In yet other embodiments, the microbial consortia can be any combination of individual microbes from any of Tables 1-3. In certain embodiments, the microbial consortia comprise two microbes, or three microbes, or four microbes, or five microbes, or six microbes, or seven microbes, or eight microbes, or nine microbes, or 10 microbes, or more than 10 microbes.

Another object of the disclosure relates to the use of the isolated microbes and microbial consortia as plant growth promoters. In other aspects, the isolated microbes and microbial consortia function as growth modifiers, which can, e.g. subvert normal senescence that leads to increased biomass.

Yet another object of the disclosure relates to the use of the isolated microbes and microbial consortia as soil health enhancers and plant health enhancers.

Another object of the disclosure is to design a microbial consortium, which is able to perform multidimensional activities in common. In certain aspects, the microbes comprising the consortium act synergistically. In aspects, the effect that the microbial consortium has on a certain plant characteristic is greater than the effect that would be observed had any one individual microbial member of the consortium been utilized singularly. That is, in some aspects, the consortium exhibit a greater than additive effect upon a desired plant characteristic, as compared to the effect that would be found if any individual member of the consortium had been utilized by itself.

In some aspects, the consortia lead to the establishment of other plant-microbe interactions, e.g. by acting as primary colonizers or founding populations that set the trajectory for the future microbiome development.

In embodiments, the disclosure is directed to synergistic combinations (or mixtures) of microbial isolates.

In some aspects, the consortia taught herein provide a wide range of agricultural applications, including: improvements in yield of grain, fruit, and flowers; improvements in growth of plant parts; improved resistance to disease; improved survivability in extreme climate; and improvements in other desired plant phenotypic characteristics. Significantly, these benefits to plants can be obtained without any hazardous side effects to the environment.

In some aspects, the individual microbes of the disclosure, or consortia comprising same, can be combined into an agriculturally acceptable composition.

In some embodiments, the agricultural compositions of the present disclosure include, but are not limited to: wetters, compatibilizing agents, antifoam agents, cleaning agents, sequestering agents, drift reduction agents, neutralizing agents, buffers, corrosion inhibitors, dyes, odorants, spreading agents, penetration aids, sticking agents, binders, dispersing agents, thickening agents, stabilizers, emulsifiers, freezing point depressants, antimicrobial agents, fertilizers, pesticides, herbicides, inert carriers, polymers, and the like.

In one embodiment of the present disclosure, the microbes (including isolated single species, or strains, or consortia), are supplied in the form of seed coatings or other applications to the seed. In embodiments, the seed coating may be applied to a naked and untreated seed. In other embodiments, the seed coating may be applied as a seed overcoat to a previously treated seed.

In some embodiments, the applied microbes may become endophytic and consequently will be present in the growing plant that was treated and its subsequent offspring. In other embodiments the microbes might be applied at the same time as a co-treatment with seed treatments.

In one embodiment of the present disclosure, the microbes are supplied in the form of granules, or plug, or soil drench that is applied to the plant growth media. In other embodiments, the microbes are supplied in the form of a foliar application, such as a foliar spray or liquid composition. The foliar spray or liquid application may be applied to a growing plant or to a growth media, e.g. soil.

In embodiments, the agricultural compositions of the disclosure can be formulated as: (1) solutions; (2) wettable powders; (3) dusting powders; (4) soluble powders; (5) emulsions or suspension concentrates; (6) seed dressings, (7) tablets; (8) water-dispersible granules; (9) water soluble granules (slow or fast release); (10) microencapsulated granules or suspensions; and (11) as irrigation components, among others. In certain aspects, the compositions may be diluted in an aqueous medium prior to conventional spray application. The compositions of the present disclosure can be applied to the soil, plant, seed, rhizosphere, rhizosheath, or other area to which it would be beneficial to apply the microbial compositions.

Still another object of the disclosure relates to the agricultural compositions being formulated to provide a high colony forming units (CFU) bacterial population or consortia. In some aspects, the agricultural compositions have adjuvants that provide for a pertinent shelf life. In embodiments, the CFU concentration of the taught agricultural compositions is higher than the concentration at which the microbes would exist naturally, outside of the disclosed methods. In another embodiment, the agricultural composition contains the microbial cells in a concentration of $10^3$-$10^{12}$ CFU per gram of the carrier or $10^5$-$10^8$ CFU per gram of the carrier. In an aspect, the microbial cells are applied as a seed coat directly to a seed at a concentration of $10^5$-$10^9$ CFU. In other aspects, the microbial cells are applied as a seed overcoat on top of another seed coat at a concentration of $10^5$-$10^9$ CFU. In other aspects, the microbial cells are applied as a co-treatment together with another seed treatment at a concentration of 105-109 CFU.

In aspects, the disclosure is directed to agricultural microbial formulations that promote plant growth. In aspects, the disclosure provides for the taught isolated microbes, and consortia comprising same, to be formulated as an agricultural bioinoculant. The taught bioinoculants can be applied to plants, seeds, or soil. Suitable examples of formulating bioinoculants comprising isolated microbes can be found in U.S. Pat. No. 7,097,830, which is herein incorporated by reference.

The disclosed polymicrobial formulations can: lower the need for nitrogen containing fertilizers, solubilize minerals, protect plants against pathogens, and make available to the plant valuable nutrients, such as phosphate, thus reducing and eliminating the need for using chemical pesticides and chemical fertilizers.

In some embodiments, the isolated and biologically pure microbes of the present disclosure can be utilized, in a method of imparting one or more beneficial properties or traits to a desired plant species.

In some embodiments, the agriculturally acceptable composition containing isolated and biologically pure microbes of the present disclosure can be utilized, in a method of imparting one or more beneficial properties or traits to a desired plant species.

In some embodiments, the consortia of the present disclosure can be utilized, in a method of imparting one or more beneficial properties or traits to a desired plant species.

In some embodiments, the agriculturally acceptable composition containing consortia of the present disclosure can be utilized, in a method of imparting one or more beneficial properties or traits to a desired plant species.

In some aspects, the isolated and biologically pure microbes of the present disclosure, and/or the consortia of the present disclosure, are derived from an accelerated microbial selection process ("AMS" process). The AMS process utilized in some aspects of the present disclosure is described, for example, in: (1) International Patent Application No. PCT/NZ2012/000041, published on Sep. 20, 2012, as International Publication No. WO 2012125050 A1, and (2) International Patent Application No. PCT/NZ2013/000171, published on Mar. 27, 2014, as international Publication No. WO 2014046553 A1, each of these PCI Applications is herein incorporated by reference in their entirety for all purposes. The AMS process is described in the present disclosure, for example, in FIGS. 1-4.

However, in other embodiments, the microbes of the present disclosure are not derived from an accelerated microbial selection process. In some aspects, the microbes utilized in embodiments of the disclosure are chosen from amongst members of microbes present in a database. In particular aspects, the microbes utilized in embodiments of the disclosure are chosen from microbes present in a database based upon particular characteristics of said microbes.

The present disclosure provides that a plant element or plant part can be effectively augmented, by coating said plant element or plant part with an isolated microbe or microbial consortia, in an amount that is not normally found on the plant element or plant part Some embodiments described herein are methods for preparing an agricultural seed composition, or seed coating, comprising: contacting the surface of a seed with a formulation comprising a purified microbial population that comprises at least one isolated microbe that is heterologous to the seed. Further embodiments entail preparing an agricultural plant composition, comprising: contacting the surface of a plant with a formulation comprising a purified microbial population that comprises at least one isolated microbe that is heterologous to the plant.

In some aspects, applying an isolated microbe, microbial consortia, and/or agricultural composition of the disclosure to a seed or plant modulates a trait of agronomic importance. The trait of agronomic importance can be, e.g., disease resistance, drought tolerance, heat tolerance, cold tolerance, salinity tolerance, metal tolerance, herbicide tolerance, chemical tolerance, improved water use efficiency, improved nitrogen utilization, improved resistance to nitrogen stress, improved nitrogen fixation, pest resistance, herbivore resistance, pathogen resistance, increased yield, increased yield under water limited conditions, health enhancement, vigor improvement, growth improvement, photosynthetic capability improvement, nutrition enhancement, altered protein content, altered oil content, increased biomass, increased shoot length, increased root length, improved root architecture, increased seed weight, faster seed germination, altered seed carbohydrate composition, altered seed oil composition, number of pods, delayed senescence, stay-green, and altered seed protein composition. In some aspects, at least 2, 3, 4, or more traits of agronomic importance are modulated. In some aspects, the modulation is a positive effect on one of the aforementioned agronomic traits.

In some aspects, the isolated microbes, consortia, and/or agricultural compositions of the disclosure can be applied to a plant, in order to modulate or alter a plant characteristic such as altered oil content, altered protein content, altered seed carbohydrate composition, altered seed oil composition, altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, decreased biomass, increased root length, decreased root length, increased seed weight, increased shoot length, decreased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome relative to a reference plant.

In some embodiments, the agricultural formulations taught herein comprise at least one member selected from the group consisting of an agriculturally compatible carrier, a tackifier, a microbial stabilizer, a fungicide, an antibacterial agent, an herbicide, a nematicide, an insecticide, a plant growth regulator, a rodenticide, and a nutrient The methods described herein can include contacting a seed or plant with at least 100 CFU or spores, at least 300 CFU or spores, at least 1,000 CFU or spores, at least 3,000 CFU or spores, at least 10,000 CFU or spores, at least 30,000 CFU or spores, at least 100,000 CFU or spores, at least 300,000 CFU or spores, at least 1,000,000 CFU or spores or more, of the microbes taught herein.

In some embodiments of the methods described herein, an isolated microbe of the disclosure is present in a formulation in an amount effective to be detectable within and/or on a target tissue of an agricultural plant. For example, the microbe is detected in an amount of at least 100 CFU or spores, at least 300 CFU or spores, at least 1,000 CFU or spores, at least 3,000 CFU or spores, at least 10,000 CFU or spores, at least 30,000 CFU or spores, at least 100,000 CFU or spores, at least 300,000 CFU or spores, at least 1,000,000 CFU or spores, or more, in and/or on a target tissue of a plant. Alternatively or in addition, the microbes of the disclosure may be present in a formulation in an amount effective to increase the biomass and/or yield of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied. Alternatively or in addition, the microbes of the disclosure may be present in a formulation in an amount effective to detectably modulate an agronomic trait of interest of a plant that has had such a formulation applied thereto, by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with a reference agricultural plant that has not had the formulations of the disclosure applied.

In some embodiments, the agricultural compositions taught herein are shelf-stable. In some aspects, the microbes taught herein are freeze dried. Also described herein are a plurality of isolated microbes confined within an object selected from the group consisting of: bottle, jar, ampule, package, vessel, bag, box, bin, envelope, carton, container, silo, shipping container, truck bed, and case.

In some aspects, combining a selected plant species with a disclosed microbe operational taxonomic unit (OTU), strain, or composition comprising any of the aforementioned leads to improved yield from crops and generation of products thereof. Therefore, in one aspect, the present disclosure provides a synthetic combination of a seed of a first plant and a preparation of a microbe(s) that is coated onto the surface of the seed of the first plant, such that the microbe is present at a higher level on the surface of the seed, than is present on the surface of an uncoated reference seed. In another aspect, the present disclosure provides a synthetic combination of a part of a first plant and a preparation of a microbe(s) that is coated onto the surface of the part of the first plant, such that the microbe is present at a higher level on the surface of the part of the first plant, than is present on the surface of an uncoated reference plant part. The aforementioned methods can be used alone, or in parallel with plant breeding and transgenic technologies.

BRIEF DESCRIPTION OF THE FIGURES

FIG. 11 shows a graphic representation of the average root length, in millimeters, of tomato at 4 days post treatment with individual microbial strains. Tomato seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 50 seeds each. Root length was measured at 4 days post treatment. The mean length of roots of the water control seed can be seen in the far right bar labelled "H2O". Results show that germination rates were good for all strains tested and some strains caused a relative increase in root length at 4 days post inoculation (DPI) compared to the water control in vitro.

Figure 1:
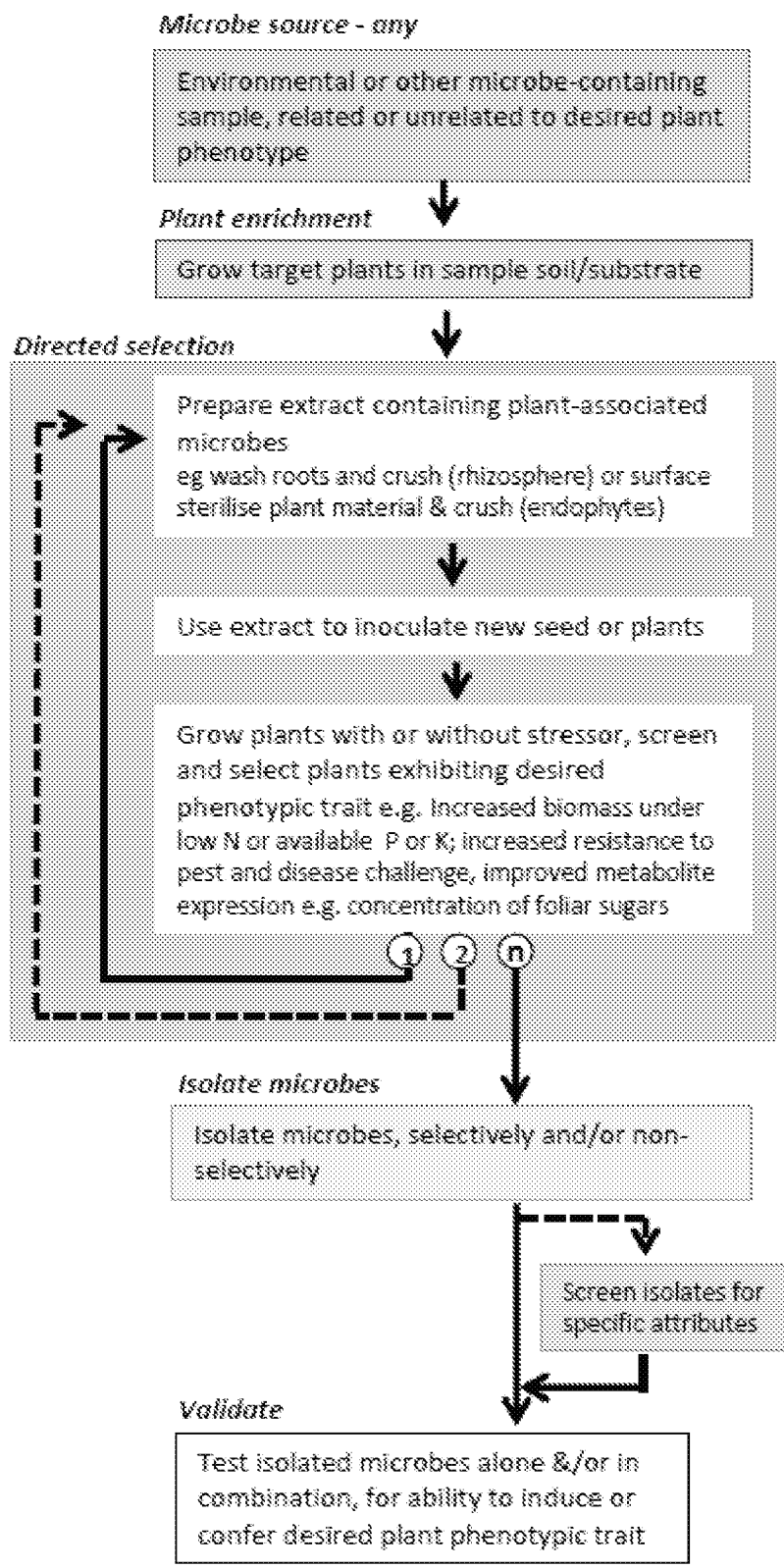
FIG. 1 shows a generalized process schematic of a disclosed method of accelerated microbial selection (AMS), also referred to herein as directed microbial selection. When the process is viewed in the context of a microbial consortium, the schematic is illustrative of a process of directed evolution of a microbial consortium. The process is one method, by which the beneficial microbes of the present disclosure were obtained.
Figure 2:
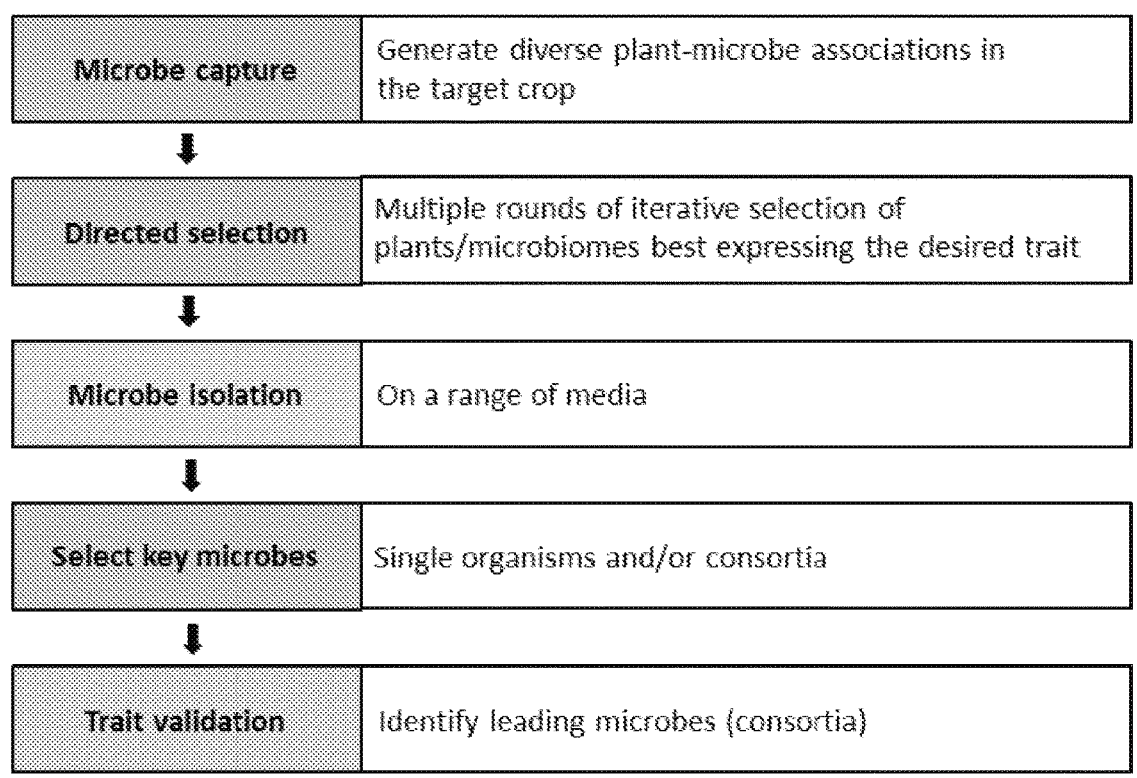
FIG. 2 shows a generalized process flow chart of an embodiment, by which the beneficial microbes of the present disclosure were obtained.
Figure 3:
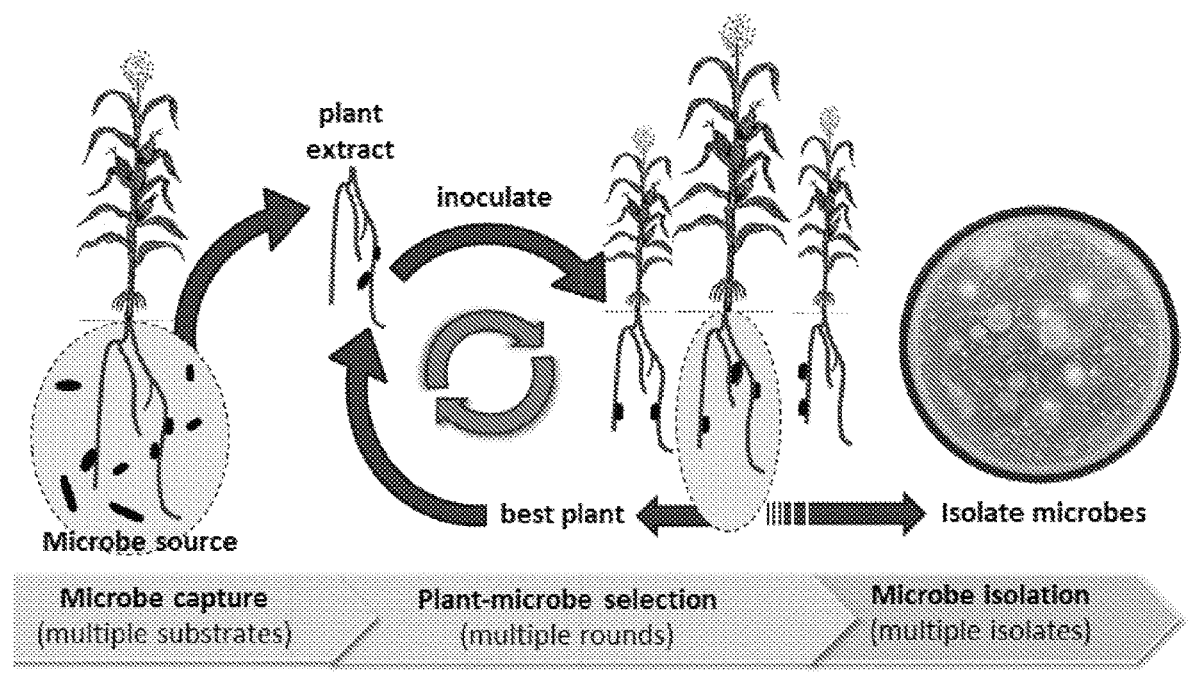
FIG. 3 shows a graphic representation and associated flow chart of an embodiment, by which the beneficial microbes of the present disclosure were obtained.
Figure 4:
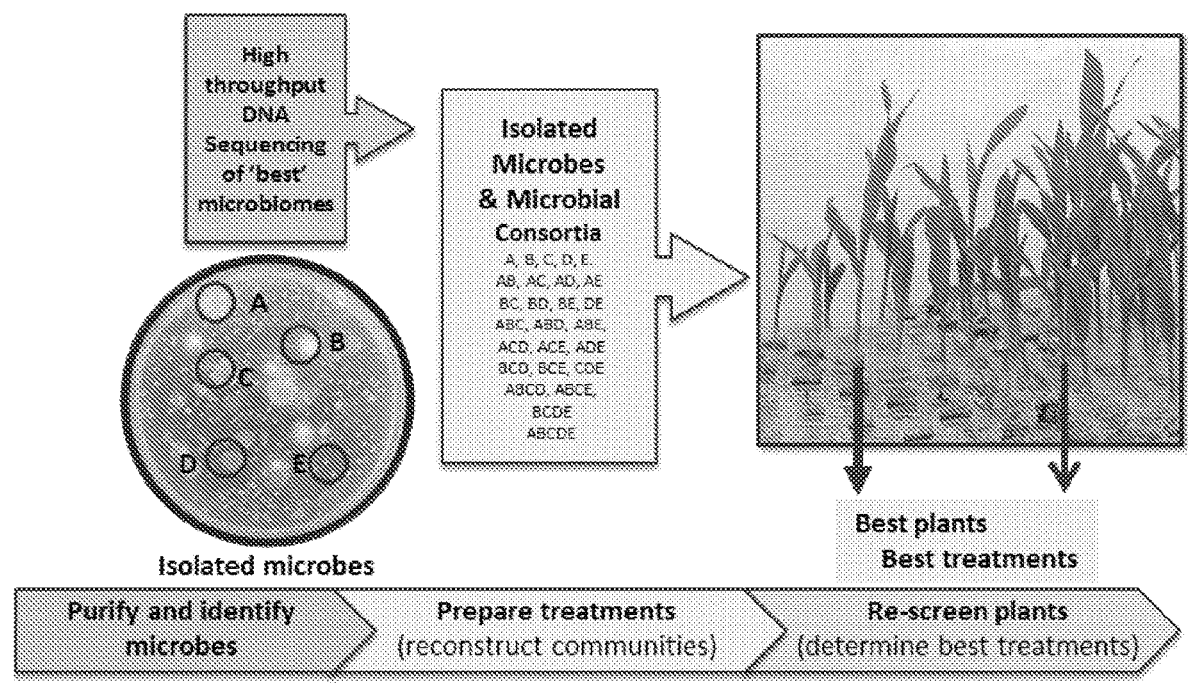
FIG. 4 shows a graphic representation and associated flow chart of an embodiment, by which the beneficial microbes of the present disclosure were obtained.

BUDAPEST TREATY ON THE INTERNATIONAL RECOGNITION OF THE DEPOSIT OF MICROORGANISMS FOR THE PURPOSE OF PATENT PROCEDURES

The microorganisms described in this Application were deposited with the Agricultural Research Service Culture Collection (NRRL), which is an International Depository Authority, located at 1815 North University Street, Peoria, Ill. 61604, USA.

The deposits were made under the terms of the Budapest Treaty on the International Recognition of the Deposit of Microorganisms for the Purposes of Patent Procedure.

The deposits were made in accordance with, and to satisfy, the criteria set forth in 37 C.F.R. §§ 1.801-1.809 and the Manual of Patent Examining Procedure §§ 2402-2411.05.

The NRRL accession numbers, dates of deposit, and descriptions for the aforementioned Budapest Treaty deposits are provided in Tables 1-3.

TABLE 1

| Microbial Species | Strains | Origin | Budapest Treaty International Depositary Authority Accession No. & Date of Deposit | Representative Deposited Species Available to the Public |
|---|---|---|---|---|
| 1. *Azotobacter chroococcum* | BDNZ57597 | NZ | | DSM-2286* |
| 2. *Pantoea agglomerans* (recently reassigned to *Pantoea vagans*) | BDNZ54499 BDNZ55529 BDNZ57547 | NZ | NRRL B-67224 Jan. 29, 2016 | |
| 3. *Pantoea agglomerans* (recently reassigned to *Pantoea vagans*) | BCI 1208 BCI 1274 BCI 1355 | US | | DSM-23078* |
| 4. *Pseudomonas fluorescens* | BDNZ54480 BDNZ56530 BDNZ56249 | NZ | | DSM-50090* |
| 5. *Pseudomonas fluorescens* | BCI 1352 | US | | DSM-50090* |
| 6. *Pseudomonas oryzihabitans* | BDNZ55530 | NZ | NRRL B-67225 Jan. 29, 2016 | |
| 7. *Pseudomonas oryzihabitans* | BCI 1184 BCI 1195 BCI 1199 | US | | DSM-6835* |
| 8. *Pseudomonas putida* | BDNZ60303 | NZ | | DSM-291* |
| 9. *Pseudomonas putida* | BCI 159 BCI 178 BCI 234 BCI 235 BCI 244 BCI 357 BCI 360 BCI 363 BCI 365 BCI 367 BCI 368 BCI 369 BCI 370 BCI 372 BCI 375 BCI 458 BCI 459 BCI 460 BCI 461 BCI 462 BCI 467 BCI 469 BCI 470 BCI 571 BCI 593 BCI 731 BCI 791 BCI 802 BCI 805 BCI 806 BCI 809 BCI 1312 | US | | DSM-291* |

TABLE 1-continued

| Microbial Species | Strains | Origin | Budapest Treaty International Depositary Authority Accession No. & Date of Deposit | Representative Deposited Species Available to the Public |
|---|---|---|---|---|
| | BCI 1314 | | | |
| | BCI 1315 | | | |
| | BCI 1319 | | | |
| | BCI 1330 | | | |
| | BCI 1333 | | | |
| | BCI 1351 | | | |
| | BCI 1353 | | | |
| | BCI 1356 | | | |
| | BCI 1358 | | | |
| | BCI 1363 | | | |
| 10. *Rahnella aquatilis* | BDNZ56532 | NZ | NRRL B-67228 Jan. 29, 2016 | |
| | BDNZ57157 | | | |
| | BDNZ58013 | | NRRL B-67229 Jan. 29, 2016 | |
| 11. *Rahnella aquatilis* | BCI 29 | US | NRRL B-67165 Dec. 18, 2015 | |
| | BCI 1158 | | | |
| 12 *Rhizobium etli* | BDNZ60473 | NZ | | DSM-11541* |
| 13 *Rhodococcus erythropolis* | BDNZ54093 | NZ | NRRL B-67227 Jan. 29, 2016 | |
| | BDNZ54299 | | | |
| 14 *Rhodococcus erythropolis* | BCI 1182 | US | | DSM-43066* |
| 15. *Stenotrophomonas maltophilia* | BDNZ54073 | NZ | NRRL B-67226 Jan. 29, 2016 | |
| 16 *Stenotrophomonas maltophilia* | BCI 7 | US | | DSM-50170* |
| | BCI 64 | | | |
| | BCI 77 | | | |
| | BCI 115 | | | |
| | BCI 120 | | | |
| | BCI 164 | | | |
| | BCI 171 | | | |
| | BCI 181 | | | |
| | BCI 271 | | | |
| | BCI 343 | | | |
| | BCI 344 | | | |
| | BCI 380 | | | |
| | BCI 539 | | | |
| | BCI 545 | | | |
| | BCI 551 | | | |
| | BCI 574 | | | |
| | BCI 588 | | | |
| | BCI 590 | | | |
| | BCI 601 | | | |
| | BCI 602 | | | |
| | BCI 606 | | | |
| | BCI 607 | | | |
| | BCI 610 | | | |
| | BCI 617 | | | |
| | BCI 618 | | | |
| | BCI 619 | | | |
| | BCI 620 | | | |
| | BCI 623 | | | |
| | BCI 665 | | | |
| | BCI 693 | | | |
| | BCI 787 | | | |
| | BCI 790 | | | |
| | BCI 793 | | | |
| | BCI 795 | | | |
| | BCI 808 | | | |
| | BCI 903 | | | |
| | BCI 908 | | | |
| | BCI 970 | | | |
| | BCI 996 | | | |
| | BCI 997 | | | |
| | BCI 1032 | | | |
| | BCI 1092 | | | |
| | BCI 1096 | | | |
| | BCI 1116 | | | |
| | BCI 1224 | | | |
| | BCI 1279 | | | |
| | BCI 1316 | | | |
| | BCI 1320 | | | |
| | BCI 1322 | | | |
| | BCI 1325 | | | |
| | BCI 1331 | | | |
| | BCI 1344 | | | |

TABLE 1-continued

| Microbial Species | Strains | Origin | Budapest Treaty International Depositary Authority Accession No. & Date of Deposit | Representative Deposited Species Available to the Public |
|---|---|---|---|---|
| | BCI 1350 | | | |
| | BCI 1357 | | | |
| | BCI 1362 | | | |

*Denotes a microbial species that has been deposited and is available to the public, but said species is not a deposit of the exact BCI or BDNZ strain.

TABLE 2

| Microbial Species | Strain | Origin | Budapest Treaty International Depositary Authority Accession No. & Date of Deposit | Representative Deposited Species Available to the Public |
|---|---|---|---|---|
| 1. *Azospirillum lipoferum* | BDNZ57661 | NZ | | DSM-1838* |
| | BDNZ66460 | | | |
| 2. *Bacillus megaterium* | BDNZ55076 | NZ | | DSM-32* |
| 3. *Bacillus megaterium* | BCI 251 | US | | DSM-32* |
| | BCI 255 | | | |
| | BCI 262 | | | |
| | BCI 264 | | | |
| 4. *Bacillus psychrosaccharolyticus* | BDNZ66518 | NZ | | DSM-13778* |
| | BDNZ66544 | | | |
| 5. *Duganella zoogloeoides* | BDNZ66500 | NZ | | DSM-16928* |
| 6. *Herbaspirillum huttiense* | BDNZ54487 | NZ | | DSM-10281* |
| 7. *Herbaspirillum huttiense* | BCI 9 | US | | DSM-10281* |
| 8. *Paenibacillus chondroitinus* | BDNZ57634 | NZ | | DSM-5051* |
| 9. *Paenibacillus polymyxa* | BDNZ55146 | NZ | | DSM-36* |
| | BDNZ66545 | | | |
| 10. *Paenibacillus polymyxa* | BCI 1118 | US | | DSM-36* |

*Denotes a microbial species that has been deposited and is available to the public, but said species is not a deposit of the exact BCI or BDNZ strain.

TABLE 3

| Microbial Species | Strain | Origin | Budapest Treaty International Depositary Authority Accession No. & Date of Deposit | Representative Deposited Species Available to the Public |
|---|---|---|---|---|
| 1. *Flavobacterium glaciei* | BDNZ66487 | NZ | | DSM-19728* |
| 2. *Massilia niastensis* | BDNZ55184 | NZ | NRRL B-67235 Feb. 8, 2016 | |
| | BCI 1217 | US | NRRL B-67199 Dec. 29, 2015 | |
| 3. *Massilia kyonggiensis* (*Massilia albidiflava*) | BCI 36 | US | | DSM-17472* |
| 4. *Sphingobium yanoikuyae* | BDNZ57662 | NZ | | DSM-7462* |
| 5. *Bacillus subtilis* | BDNZ 66347 | NZ | | DSM-1088* |
| 6. *Bacillus subtilis* | BCI 395 | US | | DSM-1088* |
| | BCI 989 | | | |
| | BCI 1089 | | | |
| 7. *Bosea minatitlanensis* | BDNZ 66354 | NZ | | DSM-13099* |
| 8. *Bosea thiooxidans* | BDNZ 54522 | NZ | | DSM-9653* |
| 9. *Bosea thiooxidans* | BCI 703 | US | NRRL B-67187 Dec. 29, 2015 | |
| | BCI 985 | | | |
| | BCI 1111 | | | |
| 10. *Bosea robinae* | BCI 1041 | US | NRRL B-67186 Dec. 29, 2015 | |
| | BCI 689 | | | |
| | BCI 765 | | | |
| 11. *Bosea eneae* | BCI 1267 | US | NRRL B-67185 Dec. 29, 2015 | |
| 12. *Caulobacter henrici* | BDNZ66341 | NZ | | DSM-4730* |
| 13. *Pseudoduganella violaceinigra* | BDNZ66361 | NZ | | DSM-15887* |
| 14. *Luteibacter yeojuensis* | BDNZ 50815 | NZ | | DSM-17673* |
| 15. *Mucilaginibacter gossypii* | BDNZ66321 | NZ | | |

TABLE 3-continued

| | Microbial Species | Strain | Origin | Budapest Treaty International Depositary Authority Accession No. & Date of Deposit | Representative Deposited Species Available to the Public |
|---|---|---|---|---|---|
| 16. | Mucilaginibacter gossypii | BCI 142<br>BCI 1156<br>BCI 1307 | US | | |
| 17. | Paenibacillus amylolyticus | BDNZ66316 | NZ | | DSM-11730* |
| 18. | Polaromonas ginsengisoli | BDNZ 66373 | NZ | NRRL B-67231<br>Feb. 8, 2016 | DSM-14656* |
| | | BDNZ 66821 | NZ | NRRL B-67234<br>Feb. 8, 2016 | |
| 19. | Ramlibacter henchirensis | BDNZ 66331 | NZ | | DSM-14656* |
| 20. | Ramlibacter henchirensis | BCI 739 | US | NRRL B-67208<br>Dec. 29, 2015 | |
| 21. | Rhizobium leguminosarum bv trifolii | BDNZ 61433 | NZ | | DSM-1980* |
| 22. | Rhizobium pisi | BDNZ 66326 | NZ | | DSM-30132* |
| 23. | Rhodoferax ferrireducens | BDNZ 66374 | NZ | | DSM-15236* |
| 24. | Sphingobium chlorophenolicum | BDNZ 61473 | NZ | | DSM-24952* |
| 25. | Sphingobium quisquiliarum | BDNZ 66576 | NZ | | DSM-24952* |
| 26. | Herbaspirillum frisingense | BDNZ 50525 | NZ | | DSM-13128* |
| 27. | Caulibacter henrici | BDNZ 66341 | NZ | | DSM-3695* |
| 28. | Chitinophaga arvensicola | BDNZ 56343 | NZ | | DSM-3695* |
| 29. | Duganella violaceinigra | BDNZ 66361 | NZ | NRRL B-67232<br>Feb. 8. 2016 | DSM-15887* |
| | | BDNZ 58291 | NZ | NRRL B-67233<br>Feb. 8, 2016 | |
| 30. | Frateuria sp. | BDNZ 52707 | NZ | | DSM-6220*<br>(Frateuria aurantia) |
| | | BDNZ 60517 | | | DSM-26515*<br>(Frateuria terrea) |
| 31. | Janthinobacterium sp. | BDNZ 54456<br>BDNZ 63491 | NZ | | |
| 32. | Luteibacter rhizovicinus | BDNZ 65069 | NZ | | DSM-16549* |
| 33. | Lysinibacillus fusiformis | BDNZ 64366 | NZ | | DSM-2898* |
| 34. | Novosphingobium rosa | BDNZ 65589<br>BDNZ 65619 | NZ | | DSM-7285* |
| 35. | Rhizobium miluonense | BDNZ 65070 | NZ | | |
| 36. | Stenotrophomonas chelatiphaga | BDNZ 54952 | NZ | | DSM-21508* |
| 37. | Stenotrophomonas chelatiphaga | BDNZ 47207 | NZ | | DSM-21508* |
| 38. | Stenotrophomonas chelatiphaga | BDNZ 64212 | NZ | | DSM-21508* |
| 39. | Stenotrophomonas chelatiphaga | BNDZ 64208 | NZ | | DSM-21508* |
| 40. | Stenotrophomonas chelatiphaga | BDNZ 58264 | NZ | | DSM-21508* |
| 41. | Stenotrophomonas rhizophila | BDNZ 50839 | NZ | | DSM-14405* |
| 42. | Stenotrophomonas rhizophila | BDNZ 48183 | NZ | | DSM-14405* |
| 43. | Stenotrophomonas rhizophila | BDNZ 45125 | NZ | | DSM-14405* |
| 44. | Stenotrophomonas rhizophila | BDNZ 46120 | NZ | | DSM-14405* |
| 45. | Stenotrophomonas rhizophila | BDNZ 46012 | NZ | | DSM-14405* |
| 46. | Stenotrophomonas rhizophila | BDNZ 51718 | NZ | | DSM-14405* |
| 47. | Stenotrophomonas rhizophila | BDNZ 56181 | NZ | | DSM-14405* |
| 48. | Stenotrophomonas rhizophila | BDNZ 54999 | NZ | | DSM-14405* |
| 49. | Stenotrophomonas rhizophila | BDNZ 54850 | NZ | | DSM-14405* |
| 50. | Stenotrophomonas rhizophila | BDNZ 54841 | NZ | | DSM-14405* |
| 51. | Stenotrophomonas rhizophila | BDNZ 66478 | NZ | | DSM-14405* |
| 52. | Stenotrophomonas rhizophila | BDNZ 46856 | NZ | | DSM-14405* |
| 53. | Stenotrophomonas rhizophila | BDNZ 65303 | NZ | | DSM-14405* |
| 54. | Stenotrophomonas terrae | BDNZ 68599 | NZ | | DSM-15236* |
| 55. | Stenotrophomonas terrae | BDNZ 68741 | NZ | | DSM-18941* |
| 56. | Achromobacter spanius | BCI 385 | US | | DSM-23806* |

TABLE 3-continued

| | Microbial Species | Strain | Origin | Budapest Treaty International Depositary Authority Accession No. & Date of Deposit | Representative Deposited Species Available to the Public |
|---|---|---|---|---|---|
| 57. | *Acidovorax soli* | BCI 690 | US | NRRL B-67182 Dec. 29, 2015 | |
| 58. | *Arthrobacter cupressi* | BCI 59 | US | NRRL B-67183 Dec. 29, 2015 | |
| 59. | *Arthrobacter mysorens* | BCI 700 | US | | DSM-12798* |
| 60. | *Arthrobacter pascens* | BCI 682 | US | | DSM-20545* |
| 61. | *Bacillus oleronius* | BCI 1071 | US | | DSM-9356* |
| 62. | *Bacillus cereus* or *Bacillus thuringiensis* (In Taxonomic Flux) | BCI 715 | US | | DSM-2046* |
| 63. | *Chitinophaga terrae* | BCI 79 | US | NRRL B-67188 Dec. 29, 2015 | |
| 64. | *Delftia lacustris* | BCI 124 | US | NRRL B-67190 Dec. 29, 2015 | |
| 65. | *Duganella radicis* | BCI 105 | US | NRRL B-67192 Dec. 29, 2015 | |
| 66. | *Duganella radicis* | BCI 57 | US | | |
| 67. | *Duganella radicis* | BCI 31 | US | NRRL B-67166 Jan. 13, 2016 | |
| 68. | *Dyadobacter soli* | BCI 68 | US | NRRL B-67194 Dec. 29, 2015 | |
| 69. | *Exiguobacterium acetylicum* | BCI 23 | US | | DSM-20416* |
| 70. | *Exiguobacterium acetylicum* | BCI 83 | US | | DSM-20416* |
| 71. | *Exiguobacterium acetylicum* | BCI 125 | US | | DSM-20416* |
| 72. | *Exiguobacterium aurantiacum* | BCI 50 | US | NRRL B-67175 Dec. 18, 2015 | |
| 73. | *Exiguobacterium* sp. (In Taxonomic Flux) | BCI 81 | US | | DSM-27935* |
| 74. | *Exiguobacterium sibiricum* | BCI 116 | US | NRRL B-67167 Dec. 18, 2016 | |
| 75. | *Herbaspirillum chlorophenolicum* | BCI 58 | US | NRRL B-67236 Feb. 8, 2016 | DSM-17796* |
| 76. | *Kosakonia radicincitans* | BCI 107 | US | | DSM-16656* |
| 77. | *Massilia kyonggiensis* (*Massilia albidiflava*) | BCI 97 | US | NRRL B-67198 Dec. 29, 2015 | |
| 78. | *Microbacterium* sp. | BCI 688 | US | | DSM-16050* |
| 79. | *Microbacterium oleivorans* | BCI 132 | US | NRRL B-67170 Dec. 18, 2015 | |
| 80. | *Mucilaginibacter gossypii* | BCI 142 | US | | |
| 81. | *Novosphigobium lindaniclasticum* | BCI 684 | US | NRRL B-67201 Dec. 29, 2015 | |
| 82. | *Novosphingohbium resinovorum* | BCI 557 | US | NRRL B-67202 Dec. 29, 2015 | |
| 83. | *Novosphingobium sediminicola* | BCI 136 | US | | DSM-27057* |
| 84. | *Novosphingohium sediminicola* | BCI 82 | US | | DSM-27057* |
| 85. | *Novosphingobium sediminicola* | BCI 130 | US | NRRL B-67168 Dec. 18, 2015 | |
| 86. | *Paenibacillus glycanilyticus* | BCI 418 | US | NRRL B-67204 Dec. 29, 2015 | |
| 87. | *Pedobacter rhizosphaerae* (*Pedobacter soli*) | BCI 598 | US | NRRL B-67205 Dec. 29, 2015 | |
| 88. | *Pedobacter terrae* | BCI 91 | US | NRRL B-67206 Dec. 29, 2015 | |
| 89. | *Pseudomonas jinjuensis* | BCI 804 | US | NRRL B-67207 Dec. 29, 2015 | |
| 90. | *Rhizobium grahamii* | BCI 691 | US | | |
| 91. | *Rhizobium lemnae* (taxonomic name changed December 2015 to *Rhizobium rhizoryzae*) | BCI 34 | US | NRRL B-67210 Dec. 29, 2015 | |
| 92. | *Agrobacterium fabrum* or *Rhizobium pusense* (In Taxonomic Flux) | BCI 106 | US | NRRL B-67212 Dec. 29, 2015 | DSM-22668* |
| 93. | *Agrobacterium fabrum* or *Rhizobium pusense* (In Taxonomic Flux) | BCI 11 | US | | DSM-22668* |
| 94. | *Agrobacterium fabrum* or *Rhizobium pusense* (In Taxonomic Flux) | BCI 609 | US | | DSM-22668* |

TABLE 3-continued

| | Microbial Species | Strain | Origin | Budapest Treaty International Depositary Authority Accession No. & Date of Deposit | Representative Deposited Species Available to the Public |
|---|---|---|---|---|---|
| 95. | Ensifer adhaerens | BCI 131 | US | NRRL B-67169 Dec. 18, 2015 | |
| 96. | Sphingopyxis alaskensis | BCI 914 | US | NRRL B-67215 Dec. 29, 2015 | DSM-13593* |
| 97. | Variovorax ginsengisoli | BCI 137 | US | NRRL B-67216 Dec. 29, 2015 | |
| 98. | Bacillus niacini | BCI 4718 | US | NRRL B-67230 Feb. 8, 2016 | DSM-2923* |
| 99. | Exiguobacterium sibiricum | BCI 116 | US | NRRL B-67167 Dec. 18, 2015 | |
| 100. | Chryseobacterium daecheongenese | BCI 45 | US | NRRL B-67172 Dec. 18, 2015 | |
| 101. | Achromobacter pulmonis | BCI 49 | | NRRL B-67174 Dec. 18, 2015 | |
| 102. | Acidovorax soli | BCI 648 | | NRRL B-67181 Dec. 29, 2015 | |
| 103. | Arthrobacter cupressi | BCI 62 | | NRRL B-67184 Dec. 29, 2015 | |
| 104. | Chininophaga terrae | BCI 109 | | NRRL B-67189 Dec. 29, 2015 | |
| 105. | Delftia lacustris | BCI 2350 | | NRRL B-67191 Dec. 29, 2015 | |
| 106. | Duganella violaceinigra | BCI 2204 | | NRRL B-67193 Dec. 29, 2015 | |
| 107. | Dyadobacter soli | BCI 96 | | NRRL B-67195 Dec. 29, 2015 | |
| 108. | Flavobacterium glacei | BCI 4005 | | NRRL B-67196 Dec. 29, 2015 | |
| 109. | Herbaspirillum chlorophenolicum | BCI 162 | | NRRL B-67197 Dec. 29, 2015 | |
| 110. | Novosphingobium lindaniclasticum | BCI 608 | | NRRL B-67200 Dec. 29, 2015 | |
| 111. | Nocosphingobium resinovorum | BCI 3709 | | NRRL B-67203 Dec. 29, 2015 | |
| 112. | Ramlibacter henchirensis | BCI 1959 | | NRRL B-67209 Dec. 29, 2015 | |
| 113. | Rhizobium rhizoryzae | BCI 661 | | NRRL B-67211 Dec. 29, 2015 | |
| 114. | Sinorhizobium chiapanecum (Ensifer adhaerens) | BCI 111 | | NRRL B-67213 Dec. 29, 2015 | |
| 115. | Sphingopyxis alaskensis | BCI 412 | | NRRL B-67214 Dec. 29, 2015 | |
| 116. | Variovorax ginsengisoli | BCI 3078 | | NRRL B-67217 Dec. 29, 2015 | |
| 117. | Kosakonia radicincitans | BCI 44 | | NRRL B-67171 Dec. 18, 2015 | |
| 118. | Pedobacter terrae | BCI 53 | | NRRL B-67176 Dec. 18, 2015 | |
| 119. | Rhizobium sp. (Agrobacterium fabrum) | BCI 46 | | NRRL B-67173 Dec. 18, 2015 | |

*Denotes a microbial species that has been deposited and is available to the public, but said species is not a deposit of the exact BCI or BDNZ strain.

DETAILED DESCRIPTION

Definitions

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "microorganism" or "microbe" should be taken broadly. These terms are used interchangeably and include, but are not limited to, the two prokaryotic domains, Bacteria and Archaea, as well as eukaryotic fungi and protists. In some embodiments, the disclosure refers to the "microbes" of Tables 1-3, or the "microbes" of various other tables present in the disclosure. This characterization can refer to not only the identified taxonomic bacterial genera of the tables, but also the identified taxonomic species, as well as the various novel and newly identified bacterial strains of said tables.

The term "microbial consortia" or "microbial consortium" refers to a subset of a microbial community of individual microbial species, or strains of a species, which can be described as carrying out a common function, or can be described as participating in, or leading to, or correlating with, a recognizable parameter or plant phenotypic trait. The community may comprise two or more species, or strains of a species, of microbes. In some instances, the microbes coexist within the community symbiotically.

The term "microbial community" means a group of microbes comprising two or more species or strains. Unlike microbial consortia, a microbial community does not have to be carrying out a common function, or does not have to be participating in, or leading to, or correlating with, a recognizable parameter or plant phenotypic trait.

The term "accelerated microbial selection" or "AMS" is used interchangeably with the term "directed microbial selection" or "DMS" and refers to the iterative selection methodology that was utilized, in some embodiments of the disclosure, to derive the claimed microbial species or consortia of said species.

As used herein, "isolate," "isolated," "isolated microbe," and like terms, are intended to mean that the one or more microorganisms has been separated from at least one of the materials with which it is associated in a particular environment (for example soil, water, plant tissue).

Thus, an "isolated microbe" does not exist in its naturally occurring environment; rather, it is through the various techniques described herein that the microbe has been removed from its natural setting and placed into a non-naturally occurring state of existence. Thus, the isolated strain may exist as, for example, a biologically pure culture, or as spores (or other forms of the strain) in association with an agricultural carrier.

In certain aspects of the disclosure, the isolated microbes exist as isolated and biologically pure cultures. It will be appreciated by one of skill in the art, that an isolated and biologically pure culture of a particular microbe, denotes that said culture is substantially free (within scientific reason) of other living organisms and contains only the individual microbe in question. The culture can contain varying concentrations of said microbe. The present disclosure notes that isolated and biologically pure microbes often "necessarily differ from less pure or impure materials." See, e.g. *In re Bergstrom*, 427 F.2d 1394, (CCPA 1970) (discussing purified prostaglandins), see also, *In re Bergy*, 596 F.2d 952 (CCPA 1979) (discussing purified microbes), see also, *Parke-Davis & Co. v. H.K. Mulford & Co.*, 189 F. 95 (S.D.N.Y. 1911) (Learned. Hand discussing purified adrenaline), *aff'd in part, rev'd in part*, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.*, 253 F.2d 156 (4th Cir. 1958) (discussing purity limitations for vitamin B12 produced by microbes), incorporated herein by reference.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified. However, "individual isolates" can comprise substantially only one genus, species, or strain, of microorganism.

The term "growth medium" as used herein, is any medium which is suitable to support growth of a plant. By way of example, the media may be natural or artificial including, but not limited to: soil, potting mixes, bark, vermiculite, hydroponic solutions alone and applied to solid plant support systems, and tissue culture gels. It should be appreciated that the media may be used alone or in combination with one or more other media. It may also be used with or without the addition of exogenous nutrients and physical support systems for roots and foliage.

In one embodiment, the growth medium is a naturally occurring medium such as soil, sand, mud, clay, humus, regolith, rock, or water. In another embodiment, the growth medium is artificial. Such an artificial growth medium may be constructed to mimic the conditions of a naturally occurring medium; however, this is not necessary. Artificial growth media can be made from one or more of any number and combination of materials including sand, minerals, glass, rock, water, metals, salts, nutrients, water. In one embodiment, the growth medium is sterile. In another embodiment, the growth medium is not sterile.

The medium may be amended or enriched with additional compounds or components, for example, a component which may assist in the interaction and/or selection of specific groups of microorganisms with the plant and each other. For example, antibiotics (such as penicillin) or sterilants (for example, quaternary ammonium salts and oxidizing agents) could be present and/or the physical conditions (such as salinity, plant nutrients (for example organic and inorganic minerals (such as phosphorus, nitrogenous salts, ammonia, potassium and micronutrients such as cobalt and magnesium), pH, and/or temperature) could be amended.

As used herein, the term "plant" includes the whole plant or any parts or derivatives thereof, such as plant cells, plant protoplasts, plant cell tissue cultures from which plants can be regenerated, plant calli, embryos, pollen, ovules, fruit, flowers, leaves, seeds, roots, root tips and the like.

As used herein, the term "cultivar" refers to a variety, strain, or race, of plant that has been produced by horticultural or agronomic techniques and is not normally found in wild populations.

As used herein, the terms "dicotyledon," "dicot" and "dicotyledonous" refer to a flowering plant having an embryo containing two cotyledons. As used herein, the terms "monocotyledon," "monocot" and "monocotyledonous" refer to a flowering plant having an embryo containing only one cotyledon. There are of course other known differences between these groups, which would be readily recognized by one of skill in the art.

As used herein, "improved" should be taken broadly to encompass improvement of a characteristic of a plant, as compared to a control plant, or as compared to a known average quantity associated with the characteristic in question. For example, "improved" plant biomass associated with application of a beneficial microbe, or consortia, of the disclosure can be demonstrated by comparing the biomass of a plant treated by the microbes taught herein to the biomass of a control plant not treated. Alternatively, one could compare the biomass of a plant treated by the microbes taught herein to the average biomass normally attained by the given plant, as represented in scientific or agricultural publications known to those of skill in the art. In the present disclosure, "improved" does not necessarily demand that the data be statistically significant (i.e. $p<0.05$); rather, any quantifiable difference demonstrating that one value (e.g. the average treatment value) is different from another e.g. the average control value) can rise to the level of "improved."

As used herein, "inhibiting and suppressing" and like terms should not be construed to require complete inhibition or suppression, although this may be desired in some embodiments.

As used herein, the term "genotype" refers to the genetic makeup of an individual cell, cell culture, tissue, organism (e.g., a plant), or group of organisms.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes. Since the present disclosure, in embodiments, relates to QTLs, i.e. genomic regions that may comprise one or more genes or regulatory sequences, it is in some instances more accurate to refer to "haplotype" (i.e. an allele of a chromosomal segment) instead of "allele", however, in those instances, the term "allele" should be understood to comprise the term "haplotype". Alleles are considered identical when they express a similar phenotype. Differences in sequence are possible but not important as long as they do not influence phenotype.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment. The term "recombinant" refers to a plant having a new genetic makeup arising as a result of a recombination event.

As used herein, the term "molecular marker" or "genetic marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location. Mapping of molecular markers in the vicinity of an allele is a procedure which can be performed by the average person skilled in molecular-biological techniques.

As used herein, the term "trait" refers to a characteristic or phenotype. For example, in the context of some embodiments of the present disclosure, yield of a crop relates to the amount of marketable biomass produced by a plant (e.g., fruit, fiber, grain). Desirable traits may also include other plant characteristics, including but not limited to: water use efficiency, nutrient use efficiency, production, mechanical harvestability, fruit maturity, shelf life, pest/disease resistance, early plant maturity, tolerance to stresses, etc. A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment.

A dominant trait results in a complete phenotypic manifestation at heterozygous or homozygous state; a recessive trait manifests itself only when present at homozygous state.

In the context of this disclosure, traits may also result from the interaction of one or more plant genes and one or more microorganism genes.

As used herein, the term "homozygous" means a genetic condition existing when two identical alleles reside at a specific locus, but are positioned individually on corresponding pairs of homologous chromosomes in the cell of a diploid organism. Conversely, as used herein, the term "heterozygous" means a genetic condition existing when two different alleles reside at a specific locus, but are positioned individually on corresponding pairs of homologous chromosomes in the cell of a diploid organism.

As used herein, the term "phenotype" refers to the observable characteristics of an individual cell, cell culture, organism (e.g., a plant), or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (h) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) Molecular Cloning: A Laboratory Manual (2nd ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, IM NaCl, 1% SDS at 37° C., and a wash in 0.1×SSC at 60° C. Hybridization procedures are well known in the art and are described by e.g. Ausubel et al., 1998 and Sambrook et al., 2001. In some embodiments, stringent conditions are hybridization in 0.25 M Na2HPO4 buffer (pH 7.2) containing 1 mM Na2EDTA, 0.5-20% sodium dodecyl sulfate at 45° C., such as 0.5%, 1%, 2%, 3%, 4%, 5%, 6%, 7%, 8%, 9%, 10%, 11%, 12%, 13%, 14%, 15%, 16%, 17%, 18%, 19% or 20%, followed by a wash in 5×SSC, containing 0.1% (w/v) sodium dodecyl sulfate, at 55° C. to 65° C.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, a "plant promoter" is a promoter capable of initiating transcription in plant cells whether or not its origin is a plant cell, e.g. it is well known that *Agrobacterium* promoters are functional in plant cells. Thus, plant promoters include promoter DNA obtained from plants, plant viruses and bacteria such as *Agrobacterium* and *Bradyrhizobium* bacteria. A plant promoter can be a constitutive promoter or a non-constitutive promoter.

As used herein, a "constitutive promoter" is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or storable markers, allowing easy detection and quantification; high level of production of a transcription factor that is part of a regulatory transcription system; production of compounds that requires ubiquitous activity in the plant; and production of compounds that are required during all stages of plant development. Non-limiting exemplary constitutive promoters include, CaMV 35S promoter, opine promoters, ubiquitin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues, such as stems, leaves, roots, or seeds.

As used herein, "inducible" or "repressible" promoter is a promoter which is under chemical or environmental factors control. Examples of environmental conditions that may effect transcription by inducible promoters include anaerobic conditions, or certain chemicals, or the presence of light.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related plant species to achieve efficient and reliable expression of transgenes in particular tissues. This is one of the main reasons for the large amount of tissue-specific promoters isolated from particular plants and tissues found in both scientific and patent literature.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the disclosure can be operably linked, either directly or indirectly, 5' to the target mRNA, or 3' to the target mRNA, or within the target mRNA, or a first complementary region is 5' and its complement is 3' to the target mRNA.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

In some embodiments, the cell or organism has at least one heterologous trait. As used herein, the term "heterologous trait" refers to a phenotype imparted to a transformed host cell or transgenic organism by an exogenous DNA segment, heterologous polynucleotide or heterologous nucleic acid. Various changes in phenotype are of interest to the present disclosure, including but not limited to modifying the fatty acid composition in a plant, altering the amino acid content of a plant, altering a plant's pathogen defense mechanism, increasing a plant's yield of an economically important trait (e.g., grain yield, forage yield, etc.) and the like. These results can be achieved by providing expression of heterologous products or increased expression of endogenous products in plants using the methods and compositions of the present disclosure A "synthetic combination" can include a combination of a plant and a microbe of the disclosure. The combination may be achieved, for example, by coating the surface of a seed of a plant, such as an agricultural plant, or host plant tissue (root, stem, leaf, etc.), with a microbe of the disclosure. Further, a "synthetic combination" can include a combination of microbes of various strains or species. Synthetic combinations have at least one variable that distinguishes the combination from any combination that occurs in nature. That variable may be, inter ally, a concentration of microbe on a seed or plant tissue that does not occur naturally, or a combination of microbe and plant that does not naturally occur, or a combination of microbes or strains that do not occur naturally together. In each of these instances, the synthetic combination demonstrates the hand of man and possesses structural and/or functional attributes that are not present when the individual elements of the combination are considered in isolation.

In some embodiments, a microbe can be "endogenous" to a seed or plant. As used herein, a microbe is considered "endogenous" to a plant or seed, if the microbe is derived from the plant specimen from which it is sourced. That is, if the microbe is naturally found associated with said plant. In embodiments in which an endogenous microbe is applied to a plant, then the endogenous microbe is applied in an amount that differs from the levels found on the plant in nature. Thus, a microbe that is endogenous to a given plant can still form a synthetic combination with the plant, if the microbe is present on said plant at a level that does not occur naturally.

In some embodiments, a microbe can be "exogenous" (also termed "heterologous") to a seed or plant. As used herein, a microbe is considered "exogenous" to a plant or seed, if the microbe is not derived from the plant specimen from which it is sourced. That is, if the microbe is not naturally found associated with said plant. For example, a microbe that is normally associated with leaf tissue of a maize plant is considered exogenous to a leaf tissue of another maize plant that naturally lacks said microbe. In another example, a microbe that is normally associated with a maize plant is considered exogenous to a wheat plant that naturally lacks said microbe.

Microbes can also be "exogenously disposed" on a given plant tissue. This means that the microbe is placed upon a plant tissue that it is not naturally found upon. For instance, if a given microbe only naturally occurs on the roots of a given plant, then that microbe could be exogenously applied to the above-ground tissue of a plant and would thereby be "exogenously disposed" upon said plant tissue. As such, a microbe is deemed exogenously disposed, when applied on a plant that does not naturally have the microbe present or does not naturally have the microbe present in the number that is being applied The compositions and methods herein may provide for an improved "agronomic trait" or "trait of agronomic importance" to a host plant, which may include, but not be limited to, the following: altered oil content, altered protein content, altered seed carbohydrate composition, altered seed oil composition, and altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, stay-green, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome, compared to an isoline plant grown from a seed without said seed treatment formulation.

Ability to Impart Beneficial Traits Upon a Given Plant Species by Microbes and Consortia of the Disclosure The present disclosure utilizes microbes to impart beneficial properties or beneficial traits) to desirable plant species, such as agronomic species of interest. In the current disclosure, the terminology "beneficial property" or "beneficial trait" is used interchangeably and denotes that a desirable plant phenotypic or genetic property of interest is modulated, by the application of a microbe or microbial consortia as described herein. As aforementioned, in some aspects, it may very well be that a metabolite produced by a given microbe is ultimately responsible for modulating or imparting a beneficial trait to a given plant.

There are a vast number of beneficial traits that can be modulated by the application of microbes of the disclosure. For instance, the microbes may have the ability to impart one or more beneficial properties to a plant species, for example: increased growth, increased yield, increased nitrogen utilization efficiency, increased stress tolerance, increased drought tolerance, increased photosynthetic rate, enhanced water use efficiency, increased pathogen resistance, modifications to plant architecture that don't necessarily impact plant yield, but rather address plant functionality, causing the plant to increase production of a metabolite of interest, etc.

In aspects, the microbes taught herein provide a wide range of agricultural applications, including: improvements in yield of grain, fruit, and flowers, improvements in growth of plant parts, improved resistance to disease, improved survivability in extreme climate, and improvements in other desired plant phenotypic characteristics.

In some aspects, the isolated microbes, consortia, and/or agricultural compositions of the disclosure can be applied to a plant, in order to modulate or alter a plant characteristic such as altered oil content, altered protein content, altered seed carbohydrate composition, altered seed oil composition, altered seed protein composition, chemical tolerance, cold tolerance, delayed senescence, disease resistance, drought tolerance, ear weight, growth improvement, health enhancement, heat tolerance, herbicide tolerance, herbivore resistance, improved nitrogen fixation, improved nitrogen utilization, improved root architecture, improved water use efficiency, increased biomass, increased root length, increased seed weight, increased shoot length, increased yield, increased yield under water-limited conditions, kernel mass, kernel moisture content, metal tolerance, number of ears, number of kernels per ear, number of pods, nutrition enhancement, pathogen resistance, pest resistance, photosynthetic capability improvement, salinity tolerance, staygreen, vigor improvement, increased dry weight of mature seeds, increased fresh weight of mature seeds, increased number of mature seeds per plant, increased chlorophyll content, increased number of pods per plant, increased length of pods per plant, reduced number of wilted leaves per plant, reduced number of severely wilted leaves per plant, and increased number of non-wilted leaves per plant, a detectable modulation in the level of a metabolite, a detectable modulation in the level of a transcript, and a detectable modulation in the proteome relative to a reference plant.

In some aspects, the isolated microbes, consortia, and/or agricultural compositions of the disclosure can be applied to a plant, in order to modulate in a negative way, a particular plant characteristic. For example, in some aspects, the microbes of the disclosure are able to decrease a phenotypic trait of interest, as this functionality can be desirable in some applications. For instance, the microbes of the disclosure may possess the ability to decrease root growth or decrease root length. Or the microbes may possess the ability to decrease shoot growth or decrease the speed at which a plant grows, as these modulations of a plant trait could be desirable in certain applications.

Isolated Microbes—Tables 1-3

In aspects, the present disclosure provides isolated microbes, including novel strains of identified microbial species, presented in Tables 1-3.

In other aspects, the present disclosure provides isolated whole microbial cultures of the species and strains identified in Tables 1-3. These cultures may comprise microbes at various concentrations.

In aspects, the disclosure provides for utilizing a microbe selected from Tables 1-3 in agriculture.

In some embodiments, the disclosure provides isolated microbial species belonging to genera of: *Azotobacter, Azospirillum, Bacillus, Bosea, Caulobacter, Duganella, Flavobacterium, Herbaspirillum, Luteibacter, Massilia, Mucilaginibacter, Pantoeo, Paenibacillus, Polaromonas, Pseudoduganella, Pseudomonas, Rahnella, Ramlibacter, Rhizobium, Rhodococcus, Rhodoferax, Sphingobium,* and *Stenotrophomonas.*

In some embodiments, a microbe from the genus *Bosea* is utilized in agriculture to impart one or more beneficial properties to a plant species.

In some embodiments, the disclosure provides isolated microbial species, selected from the group consisting of: *Azotobacter chroococcum, Pantoea agglomerans* (recently reassigned to *Pantoea vagans*), *Pseudomonas fluorescein, Pseudomonas oryzihabitans, Pseudomonas putida, Rahnella aquatilis, Rhizobium etli, Rhodococcus erythropolis,* and *Stenotrophomonas maltophilia.*

In some embodiments, disclosure provides novel isolated microbial strains of species, selected from the group consisting of: *Azotobacter chroococcum, Pantoea agglomerans* (recently reassigned to *Pantoea vagans*), *Pseudomonas fluorescens, Pseudomonas oryzihabitans, Pseudomonas putida, Rahnella aquatilis, Rhizobium etli, Rhodococcus etythropolis,* and *Stenotrophomonas maltophilia.* Particular novel strains of these aforementioned species can be found in Tables 1-3.

Furthermore, the disclosure relates to microbes having characteristics substantially similar to that of a microbe identified in Tables 1-3.

The isolated microbial species, and novel strains of said species, identified in the present disclosure, are able to impart beneficial properties or traits to target plant species.

For instance, the isolated microbes described in Tables 1-3, or consortia of said microbes, are able to improve plant health and vitality. The improved plant health and vitality can be quantitatively measured, for example, by measuring the effect that said microbial application has upon a plant phenotypic or genotypic trait.

Microbial Consortia—Tables 1-3

In aspects, the disclosure provides microbial consortia comprising a combination of at least any two microbes selected from amongst the microbes identified in Table 1.

In other aspects, the disclosure provides microbial consortia comprising a combination of at least any two microbes selected from amongst the microbes identified in Table 2.

In yet other aspects, the disclosure provides microbial consortia comprising a combination of at least any two microbes selected from amongst the microbes identified in Table 3.

Also, the disclosure provides microbial consortia comprising a combination of at least any two microbes selected from amongst the microbes identified in Tables 1-3.

In certain embodiments, the consortia of the present disclosure comprise two microbes, or three microbes, or four microbes, or five microbes, or six microbes, or seven microbes, or eight microbes, or nine microbes, or ten or more microbes. Said microbes of the consortia are different microbial species, or different strains of a microbial species.

In some embodiments, the disclosure provides consortia, comprising: at least two isolated microbial species belonging to genera of: *Azotobacter, Azospirillum, Bacillus Bosea, Caulobacter, Duganella, Flavobacterium, Herbaspirillum, Luteibacter, Mucilaginibacter, Pantoea, Paenibacillus, Polaromonas, Pseudoduganella, Pseudomonas, Rahnella, Ramlibacter, Rhizobium Rhodococcus, Rhodoferax, Sphingobium,* and *Stenotrophomonas.*

In some embodiments, the disclosure provides consortia, comprising: at least two isolated microbial species, selected from the group consisting of: *Azotobacter chroococcum, Pantoea agglomerans* (recently reassigned to *Pantoea vagans*), *Pseudomonas fluorescens, Pseudomonas oryzihabitans, Pseudomonas putida, Rahnella aquatilis, Rhizobium etli, Rhodococcus erythropolis,* and *Stenotrophomonas maltophilia.*

In some embodiments, the disclosure provides consortia, comprising: at least two novel isolated microbial strains of species, selected from the group consisting of: *Azotobacter chroococcum, Pantoea agglomerans* (recently reassigned to *Pantoea vagans*), *Pseudomonas fluorescens, Pseudomonas oryzihabitans, Pseudomonas putida, Rahnella aquatilis, Rhizobium etli, Rhodococcus erythropolis,* and *Stenotrophomonas maltophilia.* Particular novel strains of these aforementioned species can be found in Tables 1-3.

In particular aspects, the disclosure provides microbial consortia, comprising species as grouped in Tables 4-10. With respect to Tables-4-10, the letters A through I represent a non-limiting selection of microbes of the present disclosure, defined as:

A=*Azotobacter chroococcu* and associated novel strains identified in Table 1;

B=*Pantoea agglomerans* (recently reassigned to *Pantoea vagans*) and associated novel strains identified in Table 1;

C=*Pseudomonas fluorescens* and associated novel strains identified in Table 1;

D=*Pseudomonas oryzihabitans* and associated novel strains identified in Table 1;

E=*Pseudomonas putida* and associated novel strains identified in Table 1;

F=*Rahnella aquatilis* and associated novel strains identified in Table 1;

G=*Rhizobium etli* and associated novel strains identified in Table 1;

H=*Rhodococcus erythropolis* and associated novel strains identified in Table 1; and I=*Stenotrophomonas maltophilia* and associated novel strains identified in Table 1.

TABLE 4

Eight and Nine Strain Consortia

| | | | | | | |
|---|---|---|---|---|---|---|
| A, B, C, D, E, F, G, H | A, B, C, D, E, F, G, I | A, B, C, D, E, F, H, I | A, B, C, D, E, G, H, I | A, B, C, D, F, G, H, I | A, B, C, E, F, G, H, I | |
| A, B, D, E, F, G, H, I | A, C, D, E, F, G, H, I | B, C, D, E, F, G, H, I | A, B, C, D, E, F, G, H, I | | | |

TABLE 5

Seven Strain Consortia

| | | | | | |
|---|---|---|---|---|---|
| A, B, C, D, E, F, G | A, B, C, D, E, F, H | A, B, C, D, E, F, I | A, B, C, D, E, G, H | A, B, C, D, E, G, I | A, B, C, D, E, H, I |
| A, B, C, D, F, G, H | A, B, C, D, F, G, I | A, B, C, D, F, H, I | A, B, C, D, G, H, I | A, B, C, E, F, G, H | A, B, C, E, F, G, I |
| A, B, C, E, F, H, I | A, B, C, E, G, H, I | A, B, C, F, G, H, I | A, B, D, E, F, G, H | A, B, D, E, F, G, I | A, B, D, E, F, H, I |
| A, B, D, E, G, H, I | A, B, D, F, G, H, I | A, B, E, F, G, H, I | A, C, D, E, F, G, H | A, C, D, E, F, G, I | A, C, D, E, F, H, I |
| A, C, D, E, G, H, I | A, C, D, F, G, H, I | A, C, E, F, G, H, I | A, D, E, F, G, H, I | B, C, D, E, F, G, H | B, C, D, E, F, G, I |
| B, C, D, E, F, H, I | B, C, D, E, G, H, I | B, C, D, F, G, H, I | B, C, E, F, G, H, I | B, D, E, F, G, H, I | C, D, E, F, G, H, I |

TABLE 6

Six Strain Consortia

| | | | | | | |
|---|---|---|---|---|---|---|
| A, B, C, D, E, F | A, B, C, D, E, G | A, B, C, D, E, H | A, B, C, D, E, I | A, B, C, D, F, G | A, B, C, D, F, H | A, B, C, D, F, I |
| A, B, C, D, G, H | A, B, C, D, G, I | A, B, C, D, H, I | A, B, C, E, F, G | A, B, C, E, F, H | A, B, C, E, F, I | A, B, C, E, G, H |
| A, B, C, E, G, I | A, B, C, E, H, I | A, B, C, F, G, H | A, B, C, F, G, I | A, B, C, F, H, I | A, B, C, G, H, I | A, B, D, E, F, G |
| A, B, D, E, F, H | A, B, D, E, F, I | A, B, D, E, G, H | A, B, D, E, G, I | A, B, D, E, H, I | A, B, D, F, G, H | A, B, D, F, G, I |
| D, E, F, G, H, I | C, E, F, G, H, I | A, B, D, F, H, I | A, B, D, G, H, I | A, B, E, F, G, H | A, B, E, F, G, I | A, B, E, F, H, I |
| A, B, E, G, H, I | A, B, F, G, H, I | A, C, D, E, F, G | A, C, D, E, F, H | A, C, D, E, F, I | A, C, D, E, G, H | A, C, D, E, G, I |
| A, C, D, E, H, I | A, C, D, F, G, H | A, C, D, F, G, I | A, C, D, F, H, I | A, C, D, G, H, I | A, C, E, F, G, H | A, C, E, F, G, I |
| A, C, E, F, H, I | A, C, E, G, H, I | A, C, F, G, H, I | A, D, E, F, G, H | A, D, E, F, G, I | A, D, E, F, H, I | A, D, E, G, H, I |
| A, D, F, G, H, I | A, E, F, G, H, I | B, C, D, E, F, G | B, C, D, E, F, H | B, C, D, E, F, I | B, C, D, E, G, H | B, C, D, E, G, I |
| B, C, D, E, H, I | B, C, D, F, G, H | B, C, D, F, G, I | B, C, D, F, H, I | B, C, D, G, H, I | B, C, E, F, G, H | B, C, E, F, G, I |
| B, C, E, F, H, I | B, C, E, G, H, I | B, C, F, G, H, I | B, D, E, F, G, H | B, D, E, F, G, I | B, D, E, F, H, I | B, D, E, G, H, I |
| B, D, F, G, H, I | B, E, F, G, H, I | C, D, E, F, G, H | C, D, E, F, G, I | C, D, E, F, H, I | C, D, E, G, H, I | C, D, F, G, H, I |

TABLE 7

Five Strain Consortia

| | | | | | | | |
|---|---|---|---|---|---|---|---|
| A, B, C, D, E | A, B, C, D, F | A, B, C, D, G | A, B, C, D, H | A, B, C, D, I | A, B, C, E, F | A, B, C, E, G | A, B, C, E, H |
| A, B, C, F, H | A, B, C, F, G | A, B, C, F, I | A, B, C, G, H | A, B, C, G, I | A, B, C, H, I | A, B, D, E, F | A, B, D, E, G |
| A, B, D, E, I | A, B, D, F, G | A, B, D, F, H | A, B, D, F, I | A, B, D, G, H | A, B, D, G, I | A, B, D, H, I | A, B, E, F, G |
| A, B, E, F, I | A, B, E, G, H | A, B, E, G, I | A, B, E, H, I | A, B, F, G, H | A, B, F, G, I | A, B, F, H, I | A, B, G, H, I |
| A, C, D, E, G | A, C, D, E, H | A, C, D, E, I | A, C, D, F, G | A, C, D, F, H | A, C, D, F, I | A, C, D, G, H | A, C, D, G, I |
| A, C, E, F, G | A, C, E, F, H | A, C, E, F, I | A, C, E, G, H | A, C, E, G, I | A, C, E, H, I | A, C, F, G, H | A, C, F, G, I |
| A, C, G, H, I | A, D, E, F, G | A, D, E, F, H | A, D, E, F, I | A, D, E, G, H | A, D, E, G, I | A, D, E, H, I | A, D, F, G, H |
| A, D, F, H, I | A, D, G, H, I | A, E, F, G, H | A, E, F, G, I | A, E, F, H, I | A, E, G, H, I | A, F, G, H, I | B, C, D, E, F |
| B, C, D, E, H | B, C, D, E, I | B, C, D, F, G | B, C, D, F, H | B, C, D, F, I | B, C, D, G, H | B, C, D, G, I | B, C, D, H, I |
| B, C, E, F, H | B, C, E, F, I | B, C, E, G, H | B, C, E, G, I | B, C, E, H, I | B, C, F, G, H | B, C, F, G, I | B, C, F, H, I |
| B, D, E, F, G | B, D, E, F, H | B, D, E, F, I | B, D, E, G, H | B, D, E, G, I | B, D, E, H, I | B, D, F, G, H | B, D, F, G, I |
| B, D, G, H, I | B, E, F, G, H | B, E, F, G, I | B, E, F, H, I | B, E, G, H, I | B, F, G, H, I | C, D, E, F, G | C, D, E, F, H |
| C, D, E, G, H | C, D, E, G, I | C, D, E, H, I | C, D, F, G, H | C, D, F, G, I | C, D, F, H, I | C, D, G, H, I | C, E, F, G, H |
| C, E, F, H, I | C, E, G, H, I | C, F, G, H, I | D, E, F, G, H | D, E, F, G, I | D, E, F, H, I | D, E, G, H, I | D, F, G, H, I |
| A, B, C, E, I | A, B, D, E, H | A, B, E, F, H | A, C, D, E, F | A, C, D, H, I | A, C, F, H, I | A, D, F, G, I | B, C, D, E, G |
| B, C, E, F, G | B, C, G, H, I | B, D, F, H, I | C, D, E, F, I | C, E, F, G, I | E, F, G, H, I | | |

TABLE 8

Four Strain Consortia

| | | | | | | | | | |
|---|---|---|---|---|---|---|---|---|---|
| A, B, C, D | A, B, C, E | A, B, C, F | A, B, C, G | A, B, C, H | A, B, C, I | A, B, D, E | A, B, D, F | D, G, H, I | |
| A, B, D, G | A, B, D, H | A, B, D, I | A, B, E, F | A, B, E, G | A, B, E, H | A, B, E, I | A, B, F, G | E, F, G, H | |
| A, B, F, H | A, D, F, H | A, D, F, I | A, D, G, H | A, D, G, I | A, D, H, I | A, E, F, G | A, E, F, H | E, F, G, I | |
| A, B, F, I | A, B, G, H | A, B, G, I | A, B, H, I | A, C, D, E | A, C, D, F | A, C, D, G | A, C, D, H | E, F, H, I | |
| A, C, D, I | A, C, E, F | A, C, E, G | A, C, E, H | A, C, E, I | A, C, F, G | A, C, F, H | A, C, F, I | E, G, H, I | |
| A, C, G, H | A, C, G, I | A, C, H, I | A, D, E, F | A, D, E, G | A, D, E, H | A, D, E, I | A, D, F, G | F, G, H, I | |
| A, E, F, I | A, E, G, H | A, E, G, I | A, E, H, I | A, F, G, H | A, F, G, I | A, F, H, I | A, G, H, I | D, E, F, H | |
| B, C, D, E | B, C, D, F | B, C, D, G | B, C, D, H | B, C, D, I | B, C, E, F | B, C, E, G | B, C, E, H | D, E, F, I | |
| B, C, E, I | B, C, F, G | B, C, F, H | B, C, F, I | B, C, G, H | B, C, G, I | B, C, H, I | B, D, E, F | D, E, G, H | |
| B, D, E, G | B, D, E, H | B, D, E, I | B, D, F, G | B, D, F, H | B, D, F, I | B, D, G, H | B, D, G, I | D, E, G, I | |
| B, D, H, I | B, E, F, G | B, E, F, H | B, E, F, I | B, E, G, H | B, E, G, I | B, E, H, I | B, F, G, H | D, E, H, I | |
| B, F, G, I | B, F, H, I | B, G, H, I | C, D, E, F | C, D, E, G | C, D, E, H | C, D, E, I | C, D, F, G | D, F, G, H | |
| C, D, F, H | C, D, F, I | C, D, G, H | C, D, G, I | C, D, H, I | C, E, F, G | C, E, F, H | C, E, F, I | D, F, G, I | |
| C, E, G, H | C, E, G, I | C, E, H, I | C, F, G, H | C, F, G, I | C, F, H, I | C, G, H, I | D, E, F, G | D, F, H, I | |

TABLE 9

Three Strain Consortia

| | | | | | | | | | |
|---|---|---|---|---|---|---|---|---|---|
| A, B, C | A, B, D | A, B, E | A, B, F | A, B, G | A, B, H | A, B, I | A, C, D | A, C, E | G, H, I | E, F, H |
| A, C, F | A, C, G | A, C, H | A, C, I | A, D, E | A, D, F | A, D, G | A, D, H | A, D, I | F, H, I | E, F, G |
| A, E, F | A, E, G | A, E, H | A, E, I | A, F, G | A, F, H | A, F, I | A, G, H | A, G, I | F, G, I | D, H, I |
| A, H, I | B, C, D | B, C, E | B, C, F | B, C, G | B, C, H | B, C, I | B, D, E | B, D, F | F, G, H | D, G, I |
| B, D, G | B, D, H | B, D, I | B, E, F | B, E, G | B, E, H | B, E, I | B, F, G | B, F, H | E, H, I | E, F, I |
| B, F, I | B, G, H | B, G, I | B, H, I | C, D, E | C, D, F | C, D, G | C, D, H | C, D, I | E, G, I | D, G, H |
| C, E, F | C, E, G | C, E, H | C, E, I | C, F, G | C, F, H | C, F, I | C, G, H | C, G, I | E, G, H | D, F, I |
| C, H, I | D, E, F | D, E, G | D, E, H | D, E, I | D, F, G | D, F, H | | | | |

TABLE 10

Two Strain Consortia

| | | | | | | | | | | | | | | | | |
|---|---|---|---|---|---|---|---|---|---|---|---|---|---|---|---|---|
| A, B | A, C | A, D | A, E | A, F | A, G | A, H | A, I | B, C | B, D | B, E | B, F | B, G | B, H | B, I | C, D |
| C, E | C, F | C, G | C, H | C, I | D, E | D, F | D, G | D, H | D, I | E, F | E, G | E, H | E, I | F, G | F, H |
| F, I | G, H | G, I | H, I | | | | | | | | | | | | |

In some embodiments, the microbial consortia may be selected from any member group from Tables 4-10.

Isolated Microbes—Source Material

The microbes of the present disclosure were obtained, among other places, at various locales in New Zealand and the United States.

Isolated Microbes—Microbial Culture Techniques

The microbes of Tables 1-3 were identified by utilizing standard microscopic techniques to characterize the microbes' phenotype, which was then utilized to identify the microbe to a taxonomically recognized species.

The isolation, identification, and culturing of the microbes of the present disclosure can be effected using standard microbiological techniques. Examples of such techniques may be found in Gerhardt, P. (ed.) Methods for General and Molecular Microbiology. American Society for Microbiology, Washington, D.C. (1994) and Lennette, E. H. (ed.) Manual of Clinical Microbiology, Third Edition. American Society for Microbiology, Washington, D.C. (1980), each of which is incorporated by reference.

Isolation can be effected by streaking the specimen on a solid medium e.g., nutrient agar plates) to obtain a single colony, which is characterized by the phenotypic traits described hereinabove (e.g., Gram positive/negative, capable of forming spores aerobically/anaerobically, cellular morphology, carbon source metabolism, acid/base production, enzyme secretion, metabolic secretions, etc.) and to reduce the likelihood of working with a culture which has become contaminated.

For example, for isolated bacteria of the disclosure, biologically pure isolates can be obtained through repeated subculture of biological samples, each subculture followed by streaking onto solid media to obtain individual colonies. Methods of preparing, thawing, and growing lyophilized bacteria are commonly known, for example, Gherna, R. L. and C. A. Reddy. 2007, Culture Preservation, p 1019-1033. In C. A. Reddy, T. J. Beveridge, J. A. Breznak, G. A. Marzluf, T. M. Schmidt, and L R. Snyder, eds. American Society for Microbiology, Washington, D.C., 1033 pages; herein incorporated by reference. Thus freeze dried liquid formulations and cultures stored long term at −70° C. in solutions containing glycerol are contemplated for use in providing formulations of the present inventions.

The bacteria of the disclosure can be propagated in a liquid medium under aerobic conditions. Medium for growing the bacterial strains of the present disclosure includes a carbon source, a nitrogen source, and inorganic salts, as well as specially required substances such as vitamins, amino acids, nucleic acids and the like. Examples of suitable carbon sources which can be used for growing the bacterial strains include, but are not limited to, starch, peptone, yeast extract, amino acids, sugars such as glucose, arabinose, mannose, glucosamine, maltose, and the like; salts of organic acids such as acetic acid, fumaric acid, adipic acid, propionic acid, citric acid, gluconic acid, malic acid, pyruvic acid, malonic acid and the like; alcohols such as ethanol and glycerol and the like; oil or fat such as soybean oil, rice bran oil, olive oil, corn oil, sesame oil. The amount of the carbon source added varies according to the kind of carbon source and is typically between 1 to 100 gram(s) per liter of medium. Preferably, glucose, starch, and/or peptone is contained in the medium as a major carbon source, at a concentration of 0.1-5% (W/V). Examples of suitable nitrogen sources which can be used for growing the bacterial strains of the present invention include, but are not limited to, amino acids, yeast extract, tryptone, beef extract, peptone, potassium nitrate, ammonium nitrate, ammonium chloride, ammonium sulfate, ammonium phosphate, ammonia or combinations thereof. The amount of nitrogen source varies according to the type of nitrogen source, typically between 0.1 to 30 gram per liter of medium. The inorganic salts, potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc chloride, cupric sulfate, calcium chloride, sodium chloride, calcium carbonate, sodium carbonate can be used alone or in combination. The amount of inorganic acid varies according to the kind of the inorganic salt, typically between 0.001 to 10 gram per liter of medium. Examples of specially required substances include, but are not limited to, vitamins, nucleic acids, yeast extract, peptone, meat extract, malt extract, dried yeast and combinations thereof. Cultivation can be effected at a temperature, which allows the growth of the bacterial strains, essentially, between 20° C. and 46° C. In some aspects, a temperature range is 30° C.-37° C. For optimal growth, in some embodiments, the medium can be adjusted to pH 7.0-7.4. It will be appreciated that commercially available media may also be used to culture the bacterial strains, such as Nutrient Broth or Nutrient Agar available from Difco, Detroit, Mich. It will be appreciated that cultivation time may differ depending on the type of culture medium used and the concentration of sugar as a major carbon source.

In aspects, cultivation lasts between 24-96 hours. Bacterial cells thus obtained are isolated using methods, which are well known in the art. Examples include, but are not limited to, membrane filtration and centrifugal separation. The pH may be adjusted using sodium hydroxide and the like and the culture may be dried using a freeze dryer, until the water content becomes equal to 4% or less. Microbial co-cultures may be obtained by propagating each strain as described hereinabove. It will be appreciated that the microbial strains may be cultured together when compatible culture conditions can be employed.

Isolated Microbes—Microbial Strains

Microbes can be distinguished into a genus based on polyphasic taxonomy, which incorporates all available phenotypic and genotypic data into a consensus classification (Vandamme et al. 1996. Polyphasic taxonomy, a consensus approach to bacterial systematics. *Microbiol Rev* 1996, 60:407-438). One accepted genotypic method for defining species is based on overall genomic relatedness, such that strains which share approximately 70% or more relatedness using DNA-DNA hybridization, with 5° C. or less $\Delta T_m$ (the difference in the melting temperature between homologous and heterologous hybrids), under standard conditions, are considered to be members of the same species. Thus, populations that share greater than the aforementioned 70% threshold can be considered to be variants of the same species.

The 16S rRNA sequences are often used for making distinctions between species, in that if a 16S rRNA sequence shares less than a specified % sequence identity from a reference sequence, then the two organisms from which the sequences were obtained are said to be of different species.

Thus, one could consider microbes to be of the same species, if they share at least 80%, 85%, 90%, 95%, 97%, 98%, or 99% sequence identity across the 16S rRNA sequence. In aspects, a microbe could be considered to be the same species only if it shares at least 95% identity.

Further, one could define microbial strains of a species, as those that share at least 80%, 85%, 90%, 95%, 97%, 98%, or 99% sequence identity across the 16S rRNA sequence. Comparisons may also be made with 23S rRNA sequences against reference sequences. In aspects, a microbe could be considered to be the same strain only if it shares at least 95% identity. In embodiments, "substantially similar genetic characteristics" means a microbe sharing at least 95% identity.

Unculturable microbes often cannot be assigned to a definite species in the absence of a phenotype determination, the microbes can be given a candidatus designation within a genus provided their 16S rRNA sequences subscribes to the principles of identity with known species.

One approach is to observe the distribution of a large number of strains of closely related species in sequence space and to identify clusters of strains that are well resolved from other clusters. This approach has been developed by using the concatenated sequences of multiple core (housekeeping) genes to assess clustering patterns, and has been called multilocus sequence analysis (MLSA) or multilocus sequence phylogenetic analysis. MLSA has been used successfully to explore clustering patterns among large numbers of strains assigned to very closely related species by current taxonomic methods, to look at the relationships between small numbers of strains within a genus, or within a broader taxonomic grouping, and to address specific taxonomic questions. More generally, the method can be used to ask whether bacterial species exist—that is, to observe whether large populations of similar strains invariably fall into well-resolved clusters, or whether in some cases there is a genetic continuum in which clear separation into clusters is not observed.

In order to more accurately make a determination of genera, a determination of phenotypic traits, such as morphological, biochemical, and physiological characteristics are made for comparison with a reference genus archetype. The colony morphology can include color, shape, pigmentation, production of slime, etc. Features of the cell are described as to shape, size, Gram reaction, extracellular material, presence of endospores, flagella presence and location, motility, and inclusion bodies. Biochemical and physiological features describe growth of the organism at different ranges of temperature, pH, salinity and atmospheric conditions, growth in presence of different sole carbon and nitrogen sources. One of ordinary skill in the art would be reasonably apprised as to the phenotypic traits that define the genera of the present disclosure. For instance, colony color, form, and texture on a particular agar (e.g. YMA) was used to identify species of *Rhizobium*.

In one embodiment, the microbes taught herein were identified utilizing 16S rRNA gene sequences. It is known in the art that 16S rRNA contains hypervariable regions that can provide species/strain-specific signature sequences useful for bacterial identification. In the present disclosure, many of the microbes were identified via partial (500-1200 bp) 16S rRNA sequence signatures. In aspects, each strain represents a pure colony isolate that was selected from an agar plate. Selections were made to represent the diversity of organisms present based on any defining morphological characteristics of colonies on agar medium. The medium used, in embodiments, was R2 A, PDA, Nitrogen-free semi-solid medium, or MRS agar. Colony descriptions of each of the 'picked' isolates were made after 24-hour growth and then entered into our database. Sequence data was subsequently obtained for each of the isolates.

Phylogenetic analysis using the 16S rRNA gene was used to define "substantially similar" species belonging to common genera and also to define "substantially similar" strains of a given taxonomic species. Further, we recorded physiological and/or biochemical properties of the isolates that can be utilized to highlight both minor and significant differences between strains that could lead to advantageous behavior on plants.

Agricultural Compositions

In some embodiments, the microbes of the disclosure are combined into agricultural compositions. In some embodiments, the agricultural compositions of the present disclosure include, but are not limited to: wetters, compatibilizing agents (also referred to as "compatibility agents"), antifoam agents, cleaning agents, sequestering agents, drift reduction agents, neutralizing agents and buffers, corrosion inhibitors, dyes, odorants, spreading agents (also referred to as "spreaders"), penetration aids (also referred to as "penetrants"), sticking agents (also referred to as "stickers" or "binders"), dispersing agents, thickening agents (also referred to as "thickeners"), stabilizers, emulsifiers, freezing point depressants, antimicrobial agents, and the like.

In some embodiments, the agricultural compositions of the present disclosure are solid. Where solid compositions are used, it may be desired to include one or more carrier materials with the active isolated microbe or consortia. In some embodiments, the present disclosure teaches the use of carriers including, but not limited to: mineral earths such as silicas, silica gels, silicates, talc, kaolin, attaclay, limestone, chalk, loess, clay, dolomite, diatomaceous earth, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

In some embodiments, the agricultural compositions of the present disclosure are liquid. Thus in some embodiments, the present disclosure teaches that the agricultural compositions disclosed herein can include compounds or salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate.

In some embodiments, the present disclosure teaches that agricultural compositions can include binders such as: polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the agricultural compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the agricultural compositions comprise surfactants. Surfactants are sometimes used, either alone or with other additives, such as mineral or vegetable oils as adjuvants to spray-tank mixes to improve the biological performance of the microbes on the target. The types of surfactants used for bioenhancement depend generally on the nature and mode of action of the microbes. The surface-active agents can be anionic, cationic, or nonionic in character, and can be employed as emulsifying agents, wetting agents, suspending agents, or for other purposes. In some embodiments, the surfactants are non-ionics such as: alky ethoxylates, linear aliphatic alcohol ethoxylates, and aliphatic amine ethoxylates. Surfactants conventionally used in the art of formulation and which may also be used in the present formulations are described, in *McCutcheon's Detergents and Emulsifiers Annual*, MC Publishing Corp., Ridgewood, N.J., 1998, and in *Encyclopedia of Surfactants*, Vol. Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tong oil and the like; and esters of the above vegetable oils, particularly methyl esters.

In some embodiments, the agricultural compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the agricultural compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

In some embodiments, the agricultural compositions of the present disclosure comprise dispersing agents. A dispersing agent is a substance which adsorbs onto the surface of particles and helps to preserve the state of dispersion of the particles and prevents them from re-aggregating. In some embodiments, dispersing agents are added to agricultural compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylate phosphate esters are also used. In some embodiments, such as alkylarylethylene oxide condensates and EO-PO block copolymers are sometimes combined with anionics as dispersing agents for suspension concentrates.

In some embodiments, the agricultural compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in agricultural compositions of the present disclosure are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

In some embodiments, the agricultural compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

In some embodiments, the agricultural compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

In some embodiments, the agricultural compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization of pesticides when the formulation is emulsified into water. Alcohols are sometimes used as co-solvents to increase solvent power.

In some embodiments, the agricultural compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the agricultural compositions comprise one or more thickeners including, but not limited to: montmorillonite, e.g. bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenan; alginates; methyl cellulose; sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

In some embodiments, the agricultural compositions comprise a preservative.

Further, the individual microbes, or microbial consortia, or microbial communities, developed according to the disclosed methods can be combined with known actives available in the agricultural space, such as: pesticide, herbicide, bactericide, fungicide, insecticide, virucide, miticide, nemataicide, acaricide, plant growth regulator, rodenticide, anti-algae agent, biocontrol or beneficial agent. Further, the microbes, microbial consortia, or microbial communities developed according to the disclosed methods can be combined with known fertilizers. Such combinations may exhibit synergistic properties. Further still, the individual microbes, or microbial consortia, or microbial communities, developed according to the disclosed methods can be combined with inert ingredients. Also, in some aspects, the disclosed microbes are combined with biological active agents.

Metabolites Produced by Microbes and Consortia of the Disclosure

In some cases, the microbes of the present disclosure may produce one or more compounds and/or have one or more activities, e.g., one or more of the following: production of a metabolite, production of a phytohormone such as auxin, production of acetoin, production of an antimicrobial compound, production of a siderophore, production of a cellulase, production of a pectinase, production of a chitinase, production of a xylanase, nitrogen fixation, or mineral phosphate solubilization.

For example, a microbe of the disclosure may produce a phytohormone selected from the group consisting of an auxin, a cytokinin, a gibberellin, ethylene, a brassinosteroid, and abscisic acid.

Thus, a "metabolite produced by" a microbe of the disclosure, is intended to capture any molecule (small molecule, vitamin, mineral, protein, nucleic acid, lipid, fat, carbohydrate, etc.) produced by the microbe. Often, the exact mechanism of action, whereby a microbe of the disclosure imparts a beneficial trait upon a given plant species is not known. It is hypothesized, that in some instances, the microbe is producing a metabolite that is beneficial to the plant. Thus, in some aspects, a cell-free or inactivated preparation of microbes is beneficial to a plant, as the microbe does not have to be alive to impart a beneficial trait upon the given plant species, so long as the preparation includes a metabolite that was produced by said microbe and which is beneficial to a plant.

In one embodiment, the microbes of the disclosure may produce auxin (e.g., indole-3-acetic acid (IAA)). Production of auxin can be assayed. Many of the microbes described herein may be capable of producing the plant hormone auxin indole-3-acetic acid (IAA) when grown in culture. Auxin plays a key role in altering the physiology of the plant, including the extent of root growth.

Therefore, in an embodiment, the microbes of the disclosure are present as a population disposed on the surface or within a tissue of a given plant species. The microbes may produce a metabolite in an amount effective to cause a detectable increase in the amount of metabolite that is found on or within the plant, when compared to a reference plant not treated with the microbes or cell-free or inactive preparations of the disclosure. The metabolites produced by said microbial population may be beneficial to the plant species.

Plant Growth Regulators and Biostimulants

In some embodiments, the agricultural compositions of the present disclosure comprise plant growth regulators and/or biostimulants, used in combination with the taught microbes.

In some embodiments, the individual microbes, or microbial consortia, or microbial communities, developed according to the disclosed methods can be combined with known plant growth regulators in the agricultural space, such as: auxins, gibberellins, cytokinins, ethylene generators, growth inhibitors, and growth retardants.

For example, in some embodiments, the present disclosure teaches agricultural compositions comprising one or more of the following active ingredients including: ancymidol, butralin, alcohols, chloromequat chloride, cytokinin, daminozide, ethepohon, flurprimidol, giberrelic acid, gibberellin mixtures, indole-3-butryic acid (IBA), maleic hydrazide, mefludide, mepiquat chloride, mepiquat pentaborate, naphthalene-acetic acid (NAA), 1-napthaleneacetemide, (NAD), n-decanol, placlobutrazol, prohexadione calcium, trinexapac-ethyl, uniconazole, salicylic acid, abscisic acid, ethylene, brassinosteroids, jasmonates, polyamines, nitric oxide, strigolactones, or karrikins among others.

In some embodiments, the individual microbes, or microbial consortia, or microbial communities, developed according to the disclosed methods can be combined with seed inoculants known in the agricultural space, such as: QUICKROOTS®, VAULT®, RHIZO-STICK®, NODULATOR®, DORMAL®, SABREX®, among others. In some embodiments, a *Bradyrhizobium* inoculant is utilized in combination with any single microbe or microbial consortia disclosed here. In particular aspects, a synergistic effect is observed when one combines one of the aforementioned inoculants, e.g. QUICKROOTS® or *Bradyrhizobium*, with a microbe or microbial consortia as taught herein.

In some embodiments, the agricultural compositions of the present disclosure comprise a plant growth regulator, which contains: kinetin, gibberellic acid, and indole butyric acid, along with copper, manganese, and zinc.

In some aspects, the agricultural compositions comprising microbes of the disclosure (e.g. any microbe or combination thereof from Tables 1-3) and kinetin, gibberellic acid, and indole butyric acid, along with copper, manganese, and zinc, exhibit the ability to act synergistically together.

In some embodiments, the present disclosure teaches agricultural compositions comprising one or more commercially available plant growth regulators, including but not limited to: Abide®, A-Rest®, Butralin®, Fair®, Royaltac M®, Sucker-Plucker®, Off-Shoot®, Contact-85®, Citadel®, Cycocel®, E-Pro®, Conklin®, Culbac®, Cytoplex®, Early Harvest®, Foli-Zyme®, Goldengro®, Happygro®, Incite®, Megagro®, Ascend®, Radiate®, Stimulate®, Suppress®, Validate®, X-Cyte®, B-Nine®, Compress®, Dazide®, Boll Buster®, BollD®, Cerone®, Cotton Quik®, Ethrel®, Finish®, Flash®, Florel®, Mature®, MFX®, Prep®, Proxy®, Quali-Pro®, SA-50®, Setup®, Super Boll®, Whiteout®, Gutless®, Legacy®, Mastiff®, Topflor®, Ascend®, Cytoplex®, Ascend®, Early Harvest®, Falgro®, Florgib®, Foli-Zyme®, GA3®, GibGro®, Green Sol®, Incite®, N-Large®, PGR IV®, Pro-Gibb®, Release®, Rouse®, Ryzup®, Stimulate®, BVB®, Chrysal®, Fascination®, Procone®, Fair®, Rite-Hite®, Royal®, Sucker Stuff®, Embark®, Sta-Lo®, Pix®, Pentia®, DipN Grow®, Goldengro®, Hi-Yield®, Rootone®, Antac®, FST-7®, Royaltac®, Bonzi®, Cambistat®, Cutdown®, Downsize®, Florazol®, Paclo®, Paczol®, Piccolo®, Profile®, Shortstop®, Trimmit®, Turf Enhancer®, Apogee®, Armor Tech®, Goldwing®, Governor®, Groom®, Legacy®, Primeraone®, Primo®, Provair®, Solace®, T-Nex®, T-Pac®, Concise®, and Sumagic®.

In some embodiments, the present invention teaches a synergistic use of the presently disclosed microbes or microbial consortia with plant growth regulators and/or stimulants such as phytohormones or chemicals that influence the production or disruption of plant growth regulators.

In some embodiments, the present invention teaches that phytohormones can include: Auxins (e.g., Indole acetic acid IAA), Gibberellins, Cytokinins (e.g., Kinetin), Abscisic acid, Ethylene (and its production as regulated by ACC synthase and disrupted by ACC deaminase).

In some embodiments, the present invention teaches additional plant-growth promoting chemicals that may act in synergy with the microbes and microbial consortia disclosed herein, such as: humic acids, fulvic acids, amino acids, polyphenols and protein hydrolysates.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with Ascend® or other similar plant growth regulators. Ascend® is described as comprising 0.090% cytokinin as kinetin, 0.030% gibberellic acid, 0.045% indole butyric acid, and 99.835% other ingredients.

Thus, in some embodiments, the disclosure provides for the application of the taught microbes in combination with Ascend® upon any crop. Further, the disclosure provides for the application of the taught microbes in combination with Ascend® upon any crop and utilizing any method or application rate.

In some embodiments, the present disclosure teaches agricultural compositions with biostimulants.

As used herein, the term "biostimulant" refers to any substance that acts to stimulate the growth of microorganisms that may be present in soil or other plant growing medium.

The level of microorganisms in the soil or growing medium is directly correlated to plant health. Microorganisms teed on biodegradable carbon sources, and therefore plant health is also correlated with the quantity of organic matter in the soil. While fertilizers provide nutrients to feed and grow plants, in some embodiments, biostimulants provide biodegradable carbon, e.g., molasses, carbohydrates, e.g., sugars, to feed and grow microorganisms. Unless clearly stated otherwise, a biostimulant may comprise a single ingredient, or a combination of several different ingredients, capable of enhancing microbial activity or plant growth and development, due to the effect of one or more of the ingredients, either acting independently or in combination.

In some embodiments, biostimulants are compounds that produce non-nutritional plant growth responses. In some embodiments, many important benefits of biostimulants are based on their ability to influence hormonal activity. Hormones in plants (phytohormones) are chemical messengers regulating normal plant development as well as responses to the environment. Root and shoot growth, as well as other growth responses are regulated by phytohormones. In some embodiments, compounds in biostimulants can alter the hormonal status of a plant and exert large influences over its growth and health. Thus, in some embodiments, the present disclosure teaches sea kelp, humic acids, fulvic acids, and B Vitamins as common components of biostimulants. In some embodiments, the biostimulants of the present disclosure enhance antioxidant activity, which increases the plant's defensive system. In some embodiments, vitamin C, vitamin E, and amino acids such as *glycine* are antioxidants contained in biostimulants.

In other embodiments, biostimulants may act to stimulate the growth of microorganisms that are present in soil or other plant growing medium. Prior studies have shown that when certain biostimulants comprising specific organic seed extracts (e.g., soybean) were used in combination with a microbial inoculant, the biostimulants were capable of stimulating growth of microbes included in the microbial inoculant. Thus, in some embodiments, the present disclosure teaches one or more biostimulants that, when used with a microbial inoculant, is capable of enhancing the population of both native microbes and inoculant microbes. For a review of some popular uses of biostimulants, please see Calvo et al., 2014, Plant Soil 383:3-41.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with any plant biostimulant.

In some embodiments, the present disclosure teaches agricultural compositions comprising one or more commercially available biostimulants, including but not limited to: Vitazyme®, Diehard™ Biorush®, Diehard™ Biorush® Fe, Diehard™ Soluble Kelp, Diehard™ Humate SP, Phocon®, Foliar Plus™, Plant Plus™, Accomplish LM®, Titan®, Soil Builder™, Nutri Life, Soil Solution™, Seed Coat™ PercPlus™, Plant Power, CropKarb®, Thrust™, Fast2Grow®, Baccarat®, and Potente® among others.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with ProGibb® or other similar plant growth regulators. ProGibb® is described as comprising 4.0% Gibberellic Acid and 96.00% other ingredients.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with Release® or other similar plant growth regulators. Release® is described as comprising 10.0% Gibberellic Acid and 90.00% other ingredients.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with RyzUp SmartGrass® or other similar plant growth regulators. RyzUp SmartGrass® is described as comprising 40.0% Gibberellin $A_3$ and 60.00% other ingredients.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with X-CYTE™ or other similar plant growth regulators. X-CYTE™ is described as comprising 0.04% Cytokinin, as kinetin and 99.96% other ingredients.

In some embodiments, the present disclosure teaches that the individual microbes, or microbial consortia, or microbial communities, developed according to the disclosed methods—including any single microorganism or combination of microorganisms disclosed in Tables 1-3 of the specification—can be combined with N-Large™ or other similar plant growth regulators. N-Large™ is described as comprising 4.0% Gibberellin $A_3$ and 9600% other ingredients.

In some embodiments, when the microbe or microbial consortia identified according to the taught methods is combined with an active chemical agent one witnesses an additive effect on a plant phenotypic trait of interest. In other embodiments, when the microbe or microbial consortia identified according to the taught methods is combined with an active chemical agent one witness a synergistic effect on a plant phenotypic trait of interest.

In some embodiments, when the microbe or microbial consortia identified according to the taught methods is combined with a fertilizer one witnesses an additive effect on a plant phenotypic trait of interest. In other embodiments, when the microbe or microbial consortia identified according to the taught methods is combined with a fertilizer one witness a synergistic effect on a plant phenotypic trait of interest.

In some embodiments, when the microbe or microbial consortia identified according to the taught methods is combined with a plant growth regulator, one witnesses an additive effect on a plant phenotypic trait of interest. In some embodiments, when the microbe or microbial consortia identified according to the taught methods is combined with a plant growth regulator, one witnesses a synergistic effect. In some aspects, the microbes of the present disclosure are combined with Ascend® and a synergistic effect is observed for one or more phenotypic traits of interest.

In some embodiments, when the microbe or microbial consortia identified according to the taught methods is combined with a biostimulant, one witnesses an additive effect on a plant phenotypic trait of interest. In some embodiments, when the microbe or microbial consortia identified according to the taught methods is combined with a biostimulant, one witnesses a synergistic effect.

The synergistic effect obtained by the taught methods can be quantified according to Colby's formula (i.e. $(E)=X+Y-(X*Y/100)$). See Colby, R. S., "Calculating Synergistic and Antagonistic Responses of Herbicide Combinations," 1967 Weeds, vol. 15, pp. 20-22, incorporated herein by reference in its entirety. Thus, by "synergistic" is intended a component which, by virtue of its presence, increases the desired effect by more than an additive amount.

The isolated microbes and consortia of the present disclosure can synergistically increase the effectiveness of agricultural active compounds and also agricultural auxiliary compounds.

In other embodiments, when the microbe or microbial consortia identified according to the taught methods is combined with a fertilizer one witnesses a synergistic effect.

Furthermore, in certain embodiments, the disclosure utilizes synergistic interactions to define microbial consortia. That is, in certain aspects, the disclosure combines together certain isolated microbial species, which act synergistically, into consortia that impart a beneficial trait upon a plant, or which are correlated with increasing a beneficial plant trait.

The agricultural compositions developed according to the disclosure can be formulated with certain auxiliaries, in order to improve the activity of a known active agricultural compound. This has the advantage that the amounts of active ingredient in the formulation may be reduced while maintaining the efficacy of the active compound, thus allowing costs to be kept as low as possible and any official regulations to be followed. In individual cases, it may also possible to widen the spectrum of action of the active compound since plants, where the treatment with a particular active ingredient without addition was insufficiently successful, can indeed be treated successfully by the addition of certain auxiliaries along with the disclosed microbial isolates and consortia. Moreover, the performance of the active may be increased in individual cases by a suitable formulation when the environmental conditions are not favorable.

Such auxiliaries that can be used in an agricultural composition can be an adjuvant. Frequently, adjuvants take the form of surface-active or salt-like compounds. Depending on their mode of action, they can roughly be classified as modifiers, activators, fertilizers, pH buffers, and the like. Modifiers affect the wetting, sticking, and spreading properties of a formulation. Activators break up the waxy cuticle of the plant and improve the penetration of the active ingredient into the cuticle, both short-term (over minutes) and long-term (over hours). Fertilizers such as ammonium sulfate, ammonium nitrate or urea improve the absorption and solubility of the active ingredient and may reduce the antagonistic behavior of active ingredients. pH buffers are conventionally used for bringing the formulation to an optimal pH.

For further embodiments of agricultural compositions of the present disclosure, See "Chemistry and Technology of Agrochemical Formulations," edited by D. A. Knowles, copyright 1998 by Kluwer Academic Publishers, hereby incorporated by reference.

Seed Treatments

In some embodiments, the present disclosure also concerns the discovery that treating seeds before they are sown or planted with a combination of one or more of the microbes or agricultural compositions of the present disclosure can enhance a desired plant trait, e.g. plant growth, plant health, and/or plant resistance to pests.

Thus, in some embodiments, the present disclosure teaches the use of one or more of the microbes or microbial consortia as seed treatments. The seed treatment can be a seed coating applied directly to an untreated and "naked" seed. However, the seed treatment can be a seed overcoat that is applied to a seed that has already been coated with one or more previous seed coatings or seed treatments. The previous seed treatments may include one or more active compounds, either chemical or biological, and one or more inert ingredients.

The term "seed treatment" generally refers to application of a material to a seed prior to or during the time it is planted in soil. Seed treatment with microbes, and other agricultural compositions of the present disclosure, has the advantages of delivering the treatments to the locus at which the seeds are planted shortly before germination of the seed and emergence of a seedling.

In other embodiments, the present disclosure also teaches that the use of seed treatments minimizes the amount of microbe or agricultural composition that is required to successfully treat the plants, and further limits the amount of contact of workers with the microbes and compositions compared to application techniques such as spraying over soil or over emerging seedlings.

Moreover, in some embodiments, the present disclosure teaches that the microbes disclosed herein are important for enhancing the early stages of plant life (e.g., within the first thirty days following emergence of the seedling). Thus, in some embodiments, delivery of the microbes and/or compositions of the present disclosure as a seed treatment places the microbe at the locus of action at a critical time for its activity.

In some embodiments, the microbial compositions of the present disclosure are formulated as a seed treatment. In some embodiments, it is contemplated that the seeds can be substantially uniformly coated with one or more layers of the microbes and/or agricultural compositions disclosed herein, using conventional methods of mixing, spraying, or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists, or a combination thereof. Liquid seed treatments such as those of the present disclosure can be applied via either a spinning "atomizer" disk or a spray nozzle, which evenly distributes the seed treatment onto the seed as it moves though the spray pattern. In aspects, the seed is then mixed or tumbled for an additional period of time to achieve additional treatment distribution and drying.

The seeds can be primed or unprimed before coating with the microbial compositions to increase the uniformity of germination and emergence. In an alternative embodiment, a dry powder formulation can be metered onto the moving seed and allowed to mix until completely distributed.

In some embodiments, the seeds have at least part of the surface area coated with a microbiological composition, according to the present disclosure. In some embodiments, a seed coat comprising the microbial composition is applied directly to a naked seed. In some embodiments, a seed overcoat comprising the microbial composition is applied to a seed that already has a seed coat applied thereon. In some aspects, the seed may have a seed coat comprising, e.g. clothianidin and/or *Bacillus firmus*-I-1582, upon which the present composition will be applied on top of, as a seed overcoat. In some aspects, the taught microbial compositions are applied as a seed overcoat to seeds that have already been treated with PONCHO™ VOTiVO™. In some aspects, the seed may have a seed coat comprising, e.g. Metalaxyl, and/or clothianidin, and/or *Bacillus firmus*-I-1582, upon which the present composition will be applied on top of, as a seed overcoat. In some aspects, the taught microbial compositions are applied as a seed overcoat to seeds that have already been treated with ACCELERON™.

In some embodiments, the microorganism-treated seeds have a microbial spore concentration, or microbial cell concentration, from about: $10^3$ to $10^{12}$, $10^3$ to $10^{11}$, $10^3$ to $10^{10}$, $10^3$ to $10^9$, $10^3$ to $10^8$, $10^3$ to $10^7$, $10^3$ to $10^0$, $10^3$ to $10^5$, or $10^3$ to $10^4$ per seed.

In some embodiments, the microorganism-treated seeds have a microbial spore concentration, or microbial cell concentration, from about: $10^4$ to $10^{12}$, $10^4$ to $10^{11}$, $10^4$ to $10^{10}$, $10^4$ to $10^9$, $10^4$ to $10^8$, $10^4$ to $10^7$, $10^4$ to $10^6$, or $10^4$ to $10^5$ per seed.

In some embodiments, the microorganism-treated seeds have a microbial spore concentration, or microbial cell concentration, from about: $10^5$ to $10^{12}$, $10^5$ to $10^{11}$, $10^5$ to $10^{10}$, $10^5$ to $10^9$, $10^5$ to $10^8$, $10^5$ to $10^7$, or $10^5$ to $10^6$ per seed.

In some embodiments, the microorganism-treated seeds have a microbial spore concentration, or microbial cell concentration, from about: $10^5$ to $10^9$ per seed.

In some embodiments, the microorganism-treated seeds have a microbial spore concentration, or microbial cell concentration, of at least about: $1 \times 10^3$, or $1 \times 10^4$, or $1 \times 10^5$, or $1 \times 10^6$, or $1 \times 10^7$, or $1 \times 10^8$, or $1 \times 10^9$ per seed.

In some embodiments, the amount of one or more of the microbes and/or agricultural compositions applied to the seed depend on the final formulation, as well as size or type of the plant or seed utilized. In some embodiments, one or more of the microbes are present in about 2% w/w to about 80% w/w of the entire formulation. In some embodiments, the one or more of the microbes employed in the compositions is about 5% w/w to about 65% w/w, or 10% w/w to about 60% w/w by weight of the entire formulation.

In some embodiments, the seeds may also have more spores or microbial cells per seed, such as, for example about $10^2$, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$ or $10^{17}$ spores or cells per seed.

In some embodiments, the seed coats of the present disclosure can be up to 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm, 510 μm, 520 μm, 530 μm, 540 μm, 550 μm, 560 μm, 570 μm, 580 μm, 590 μm, 600 μm, 610 μm, 620 μm, 630 μm, 640 μm, 650 μm, 660 μm, 670 μm, 680 μm, 690 μm, 700 μm, 710 μm, 720 μm, 730 μm, 740 μm, 750 μm, 760 μm, 770 μm, 780 μm, 790 μm, 800 μm, 810 μm, 820 μm, 830 μm, 840 μm, 850 μm, 860 μm, 870 μm, 880 μm, 890 μm, 900 μm, 910 μm, 920 μm, 930 μm, 940 μm, 950 μm, 960 μm, 970 μm, 980 μm, 990 μm, 1000 μm, 1010 μm, 1020 μm, 1030 μm, 1040 μm, 1050 μm, 1060 μm, 1070 μm, 1080 μm, 1090 μm, 1100 μm, 1110 μm, 1120 μm, 1130 μm, 1140 μm, 1150 μm, 1160 μm, 1170 μm, 1180 μm, 1190 μm, 1200 μm, 1210 μm, 1220 μm, 1230 μm, 1240 μm, 1250 μm, 1260 μm, 1270 μm, 1280 μm, 1290 μm, 1300 μm, 1310 μm, 1320 μm, 1330 μm, 1340 μm, 1350 μm, 1360 μm, 1370 μm, 1380 μm, 1390 μm, 1400 μm, 1410 μm, 1420 μm, 1430 μm, 1440 μm, 1450 μm, 1460 μm, 1470 μm, 1480 μm, 1490 μm, 1500 μm, 1510 μm, 1520 μm, 1530 μm, 1540 μm, 1550 μm, 1560 μm, 1570 μm, 1580 μm, 1590 μm, 1600 μm, 1610 μm, 1620 μm, 1630 μm, 1640 μm, 1650 μm, 1660 μm, 1670 μm, 1680 μm, 1690 μm, 1700 μm, 1710 μm, 1720 μm, 1730 μm, 1740 μm, 1750 μm, 1760 μm, 1770 μm, 1780 μm, 1790 μm, 1800 μm, 1810 μm, 1820 μm, 1830 μm, 1840 μm, 1850 μm, 1860 μm, 1870 μm, 1880 μm, 1890 μm, 1900 μm, 1910 μm, 1920 μm, 1930 μm, 1940 μm, 1950 μm, 1960 μm, 1970 μm, 1980 μm, 1990 μm, 2000 μm, 2010 μm, 2020 μm, 2030 μm, 2040 μm, 2050 μm, 2060 μm, 2070 μm, 2080 μm, 2090 μm, 2100 μm, 2110 μm, 2120 μm, 2130 μm, 2140 μm, 2150 μm, 2160 μm, 2170 μm, 2180 μm, 2190 μm, 2200 μm, 2210 μm, 2220 μm, 2230 μm, 2240 μm, 2250 μm, 2260 μm, 2270 μm, 2280 μm, 2290 μm, 2300 μm, 2310 μm, 2320 μm, 2330 μm, 2340 μm, 2350 μm, 2360 μm, 2370 μm, 2380 μm, 2390 μm, 2400 μm, 2410 μm, 2420 μm, 2430 μm, 2440 μm, 2450 μm, 2460 μm, 2470 μm, 2480 μm, 2490 μm, 2500 μm, 2510 μm, 2520 μm, 2530 μm, 2540 μm, 2550 μm, 2560 μm, 2570 μm, 2580 μm, 2590 μm, 2600 μm, 2610 μm, 2620 μm, 2630 μm, 2640 μm, 2650 μm, 2660 μm, 2670 μm, 2680 μm, 2690 μm, 2700 μm, 2710 μm, 2720 μm, 2730 μm, 2740 μm, 2750 μm, 2760 μm, 2770 μm, 2780 μm, 2790 μm, 2800 μm, 2810 μm, 2820 μm, 2830 μm, 2840 μm, 2850 μm, 2860 μm, 2870 μm, 2880 μm, 2890 μm, 2900 μm, 2910 μm, 2920 μm, 2930 μm, 2940 μm, 2950 μm, 2960 μm, 2970 μm, 2980 μm, 2990 μm, or 3000 μm thick.

In some embodiments, the seed coats of the present disclosure can be 0.5 mm, 1 mm, 1.5 mm, 2 mm, 2.5 mm, 3 mm, 3.5 mm, 4 mm, 4.5 mm, or 5 mm thick.

In some embodiments, the seed coats of the present disclosure can be at least 0.5%, 1%, 1.5%, 2%, 2.5%, 3%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 25.5%, 26%, 26.5%, 27%, 27.5%, 28%, 28.5%, 29%, 29.5%, 30%, 30.5%, 31%, 31.5%, 32%, 32.5%, 33%, 33.5%, 34%, 34.5%, 35%, 35.5%, 36%, 36.5%, 37%, 37.5%, 38%, 38.5%, 39%, 39.5%, 40%, 40.5%, 41%, 41.5%, 42%, 42.5%, 43%, 43.5%, 44%, 44.5%, 45%, 45.5%, 46%, 46.5%, 47%, 47.5%, 48%, 48.5%, 49%, 49.5%, or 50% of the uncoated seed weight.

In some embodiments, the microbial spores and/or cells can be coated freely onto the seeds or they can be formulated in a liquid or solid composition before being coated onto the seeds. For example, a solid composition comprising the microorganisms can be prepared by mixing a solid carrier with a suspension of the spores until the solid carriers are impregnated with the spore or cell suspension. This mixture can then be dried to obtain the desired particles.

In some other embodiments, it is contemplated that the solid or liquid microbial compositions of the present disclosure further contain functional agents e.g., activated carbon, nutrients (fertilizers), and other agents capable of improving the germination and quality of the products or a combination thereof.

Seed coating methods and compositions that are known in the art can be particularly useful when they are modified by the addition of one of the embodiments of the present disclosure. Such coating methods and apparatus for their application are disclosed in, for example: U.S. Pat. Nos. 5,916,029; 5,918,413; 5,554,445; 5,389,399; 4,759,945; 4,465,017, and U.S. patent application Ser. No. 13/260,310, each of which is incorporated by reference herein.

Seed coating compositions are disclosed in, for example: U.S. Pat. Nos. 5,939,356; 5,876,739, 5,849,320; 5,791,084, 5,661,103; 5,580,544, 5,328,942; 4,735,015; 4,634,587; 4,372,080, 4,339,456; and 4,245,432, each of which is incorporated by reference herein.

In some embodiments, a variety of additives can be added to the seed treatment formulations comprising the inventive compositions. Binders can be added and include those composed of an adhesive polymer that can be natural or synthetic without phytotoxic effect on the seed to be coated. The binder may be selected from polyvinyl acetates; polyvinyl acetate copolymers; ethylene vinyl acetate (EVA) copolymers; polyvinyl alcohols; polyvinyl alcohol copolymers; celluloses, including ethylcelluloses, methylcelluloses, hydroxymethylcelluloses, hydroxypropy celluloses and carboxymethylcellulose; polyvinylpyrolidones; polysaccharides, including starch, modified starch, dextrins, maltodextrins, alginate and chitosans; fats; oils; proteins, including gelatin and zeins; gum arabics; shellacs; vinylidene chloride and vinylidene chloride copolymers; calcium lignosulfonates; acrylic copolymers; polyvinylacrylates; polyethylene oxide; acrylamide polymers and copolymers; polyhydroxyethyl acrylate, methylacrylamide monomers; and polychloroprene.

Any of a variety of colorants may be employed, including organic chromophores classified as nitroso; nitro; azo, including monoazo, bisazo and polyazo; acridine, anthraquinone, azine, diphenylmethane, indamine, indophenol, methine, oxazine, phthalocyanine, thiazine, thiazole, triarylmethane, xanthene. Other additives that can be added include trace nutrients such as salts of iron, manganese, boron, copper, cobalt, molybdenum and zinc.

A polymer or other dust control agent can be applied to retain the treatment on the seed surface.

In some specific embodiments, in addition to the microbial cells or spores, the coating can further comprise a layer of adherent. The adherent should be non-toxic, biodegradable, and adhesive. Examples of such materials include, but are not limited to, polyvinyl acetates; polyvinyl acetate copolymers; polyvinyl alcohols; polyvinyl alcohol copolymers; celluloses, such as methyl celluloses, hydroxymethyl celluloses, and hydroxymethyl propyl celluloses; dextrins; alginates; sugars; molasses; polyvinyl pyrrolidones; polysaccharides; proteins; fats; oils; gum a.ra.bics; gelatins; syrups; and starches. More examples can be found in, for example, U.S. Pat. No. 7,213,367, incorporated herein by reference.

Various additives, such as adherents, dispersants, surfactants, and nutrient and buffer ingredients, can also be included in the seed treatment formulation. Other conventional seed treatment additives include, but are not limited to: coating agents, wetting agents, buffering agents, and polysaccharides. At least one agriculturally acceptable carrier can be added to the seed treatment formulation such as water, solids, or dry powders. The dry powders can be derived from a variety of materials such as calcium carbonate, gypsum, vermiculite, talc, humus, activated charcoal, and various phosphorous compounds.

In some embodiments, the seed coating composition can comprise at least one filler, which is an organic or inorganic, natural or synthetic component with which the active components are combined to facilitate its application onto the seed. In aspects, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates.

In some embodiments, the seed treatment formulation may further include one or more of the following ingredients: other pesticides, including compounds that act only below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxi me derivatives; chemical fertilizers; biological fertilizers; and biocontrol agents such as other naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed, or alternatively may be added as part of the seed coating composition of the disclosure.

In some embodiments, the formulation that is used to treat the seed in the present disclosure can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation can be about 0.5% to about 99% by weight (w/w), or 5-40%, or as otherwise formulated by those skilled in the art.

As mentioned above, other conventional inactive or inert ingredients can be incorporated into the formulation. Such inert ingredients include, but are not limited to: conventional sticking agents; dispersing agents such as methylcellulose, for example, serve as combined dispersant/sticking agents for use in seed treatments; polyvinyl alcohol; lecithin, polymeric dispersants (e.g., polyvinylpyrrolidone/vinyl acetate); thickeners (e.g., clay thickeners to improve viscosity and reduce settling of particle suspensions); emulsion stabilizers; surfactants; antifreeze compounds (e.g., urea), dyes, colorants, and the like. Further inert ingredients useful in the present disclosure can be found in McCutcheon's, vol. 1, "Emulsifiers and Detergents," MC Publishing Company, Glen Rock, N.J., U.S.A., 1996, incorporated by reference herein.

The seed coating formulations of the present disclosure can be applied to seeds by a variety of methods, including, but not limited to: mixing in a container (e.g., a bottle or bag), mechanical application, tumbling, spraying, and immersion. A variety of active or inert material can be used for contacting seeds with microbial compositions according to the present disclosure.

In some embodiments, the amount of the microbes or agricultural composition that is used for the treatment of the seed will vary depending upon the type of seed and the type of active ingredients, but the treatment will comprise contacting the seeds with an agriculturally effective amount of the inventive composition.

As discussed above, an effective amount means that amount of the inventive composition that is sufficient to affect beneficial or desired results. An effective amount can be administered in one or more administrations.

In some embodiments, in addition to the coating layer, the seed may be treated with one or more of the following ingredients: other pesticides including fungicides and herbicides; herbicidal safeners; fertilizers and/or biocontrol agents. These ingredients may be added as a separate layer or alternatively may be added in the coating layer.

In some embodiments, the seed coating formulations of the present disclosure may be applied to the seeds using a variety of techniques and machines, such as fluidized bed techniques, the roller mill method, rotostatic seed treaters, and drum coaters. Other methods, such as spouted beds may also be useful. The seeds may be pre-sized before coating. After coating, the seeds are typically dried and then transferred to a sizing machine for sizing. Such procedures are known in the art.

In some embodiments, the microorganism-treated seeds may also be enveloped with a film overcoating to protect the coating. Such overcoatings are known in the art and may be applied using fluidized bed and drum film coating techniques.

In other embodiments of the present disclosure, compositions according to the present disclosure can be introduced onto a seed by use of solid matrix priming. For example, a quantity of an inventive composition can be mixed with a solid matrix material and then the seed can be placed into contact with the solid matrix material for a period to allow the composition to be introduced to the seed. The seed can then optionally be separated from the solid matrix material and stored or used, or the mixture of solid matrix material plus seed can be stored or planted directly. Solid matrix materials which are useful in the present disclosure include polyacrylamide, starch, clay, silica, alumina, soil, sand, polyurea, polyacrylate, or any other material capable of absorbing or adsorbing the inventive composition for a time and releasing that composition into or onto the seed. It is useful to make sure that the inventive composition and the solid matrix material are compatible with each other. For example, the solid matrix material should be chosen so that it can release the composition at a reasonable rate, for example over a period of minutes, hours, or days.

Microorganisms

As used herein "microorganism" should be taken broadly. It includes, but is not limited to, the two prokaryotic domains, Bacteria and Archaea, as well as eukaryotic fungi and protists.

By way of example, the microorganisms may include: Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Bradyrhizobium, Sinorhizobium* and *Halomonas*), Firmicutes (such as *Bacillus, Paenibacillus, Lactobacillus, Mycoplasma,* and *Acetobacterium*), Actinobacteria (such as *Streptomyces, Rhodococcus, Microbacterium,* and *Curtobacterium*), and the fungi Ascomycota (such as *Trichoderma, Ampelomyces, Coniothyrium, Paecoelomyces, Penicillium, Cladosporium, Hypocrea, Beauveria, Metarhizium, Verticullium, Cordyceps, Pichea,* and *Candida*, Basidiomycota (such as *Coprinus, Corticium,* and *Agaricus*) and Oomycota (such as *Pythium, Mucor,* and *Mortierella*).

In a particular embodiment, the microorganism is an endophyte, or an epiphyte, or a microorganism inhabiting the plant rhizosphere or rhizosheath. That is, the microorganism may be found present in the soil material adhered to the roots of a plant or in the area immediately adjacent a plant's roots. In one embodiment, the microorganism is a seed-borne endophyte.

Endophytes may benefit host plants by preventing pathogenic organisms from colonizing them. Extensive colonization of the plant tissue by endophytes creates a "barrier effect," where the local endophytes outcompete and prevent pathogenic organisms from taking hold. Endophytes may also produce chemicals which inhibit the growth of competitors, including pathogenic organisms.

In certain embodiments, the microorganism is unculturable. This should be taken to mean that the microorganism is not known to be culturable or is difficult to culture using methods known to one skilled in the art.

Microorganisms of the present disclosure may be collected or obtained from any source or contained within and/or associated with material collected from any source.

In an embodiment, the microorganisms are obtained from any general terrestrial environment, including its soils, plants, fungi, animals (including invertebrates) and other biota, including the sediments, water and biota of lakes and rivers; from the marine environment, its biota and sediments (for example sea water, marine muds, marine plants, marine invertebrates (for example sponges), marine vertebrates (for example, fish)); the terrestrial and marine geosphere (regolith and rock, for example crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, road surfaces).

In another embodiment the microorganisms are collected from a source likely to favor the selection of appropriate microorganisms. By way of example, the source may be a particular environment in which it is desirable for other plants to grow, or which is thought to be associated with terroir. In another example, the source may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the microorganisms may be collected from commercial crops grown in such environments, or more specifically from individual crop plants best displaying a trait of interest amongst a crop grown in any specific environment, for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste, or smell. The microorganisms may be collected from a plant of interest or any material occurring in the environment of interest, including fungi and other animal and plant biota, soil, water, sediments, and other elements of the environment as referred to previously. In certain embodiments, the microorganisms are individual isolates separated from different environments.

In one embodiment, a microorganism or a combination of microorganisms, of use in the methods of the disclosure may be selected from a pre-existing collection of individual microbial species or strains based on some knowledge of their likely or predicted benefit to a plant. For example, the microorganism may be predicted to: improve nitrogen fixation; release phosphate from the soil organic matter; release phosphate from the inorganic forms of phosphate (e.g. rock phosphate); "fix carbon" in the root microsphere; live in the rhizosphere of the plant thereby assisting the plant in absorbing nutrients from the surrounding soil and then providing these more readily to the plant; increase the number of nodules on the plant roots and thereby increase the number of symbiotic nitrogen fixing bacteria (e.g. *Rhizobium* species) per plant and the amount of nitrogen fixed by the plant; elicit plant defensive responses such as ISR (induced systemic resistance) or SAR (systemic acquired resistance) which help the plant resist the invasion and spread of pathogenic microorganisms; compete with microorganisms deleterious to plant growth or health by antagonism, or competitive utilization of resources such as nutrients or space; change the color of one or more part of the plant, or change the chemical profile of the plant, its smell, taste or one or more other quality.

In one embodiment a microorganism or combination of microorganisms is selected from a pre-existing collection of individual microbial species or strains that provides no knowledge of their likely or predicted benefit to a plant. For example, a collection of unidentified microorganisms isolated from plant tissues without any knowledge of their ability to improve plant growth or health, or a collection of microorganisms collected to explore their potential for producing compounds that could lead to the development of pharmaceutical drugs.

In one embodiment, the microorganisms are acquired from the source material (for example, soil, rock, water, air, dust, plant or other organism) in which they naturally reside. The microorganisms may be provided in any appropriate form, having regard to its intended use in the methods of the disclosure. However, by way of example only, the microorganisms may be provided as an aqueous suspension, gel, homogenate, granule, powder, slurry, live organism or dried material.

The microorganisms of the disclosure may be isolated in substantially pure or mixed cultures. They may be concentrated, diluted, or provided in the natural concentrations in which they are found in the source material. For example, microorganisms from saline sediments may be isolated for use in this disclosure by suspending the sediment in fresh water and allowing the sediment to fall to the bottom. The water containing the bulk of the microorganisms may be removed by decantation after a suitable period of settling and either applied directly to the plant growth medium, or concentrated by filtering or centrifugation, diluted to an appropriate concentration and applied to the plant growth medium with the bulk of the salt removed. By way of further example, microorganisms from mineralized or toxic sources may be similarly treated to recover the microbes for application to the plant growth material to minimize the potential for damage to the plant.

In another embodiment, the microorganisms are used in a crude form, in which they are not isolated from the source material in which they naturally reside. For example, the microorganisms are provided in combination with the source material in which they reside; for example, as soil, or the roots, seed or foliage of a plant. In this embodiment, the source material may include one or more species of microorganisms.

In some embodiments, a mixed population of microorganisms is used in the methods of the disclosure.

In embodiments of the disclosure where the microorganisms are isolated from a source material (for example, the material in which they naturally reside), any one or a combination of a number of standard techniques which will be readily known to skilled persons may be used. However, by way of example, these in general employ processes by which a solid or liquid culture of a single microorganism can be obtained in a substantially pure form, usually by physical separation on the surface of a solid microbial growth medium or by volumetric dilutive isolation into a liquid microbial growth medium. These processes may include isolation from dry material, liquid suspension, slurries or homogenates in which the material is spread in a thin layer over an appropriate solid gel growth medium, or serial dilutions of the material made into a sterile medium and inoculated into liquid or solid culture media.

Whilst not essential, in one embodiment, the material containing the microorganisms may be pre-treated prior to the isolation process in order to either multiply all microorganisms in the material, or select portions of the microbial population, either by enriching the material with microbial nutrients (for example, by pasteurizing the sample to select for microorganisms resistant to heat exposure (for example, bacilli), or by exposing the sample to low concentrations of an organic solvent or sterilant (for example, household bleach) to enhance the survival of spore-forming or solvent-resistant microorganisms) Microorganisms can then be isolated from the enriched materials or materials treated for selective survival, as above.

In an embodiment of the disclosure, endophytic or epiphytic microorganisms are isolated from plant material. Any number of standard techniques known in the art may be used and the microorganisms may be isolated from any appropriate tissue in the plant, including for example root, stem and leaves, and plant reproductive tissues. By way of example, conventional methods for isolation from plants typically include the sterile excision of the plant material of interest (e.g. root or stem lengths, leaves), surface sterilization with an appropriate solution (e.g. 2% sodium hypochlorite), after which the plant material is placed on nutrient medium for microbial growth (See, for example, Strobel G and Daisy B (2003) Microbiology and Molecular Biology Reviews 67 (4): 491-502; Zinniel D K et al. (2002) Applied and Environmental Microbiology 68 (5): 2198-2208).

In one embodiment of the disclosure, the microorganisms are isolated from root tissue. Further methodology for isolating microorganisms from plant material are detailed hereinafter.

In one embodiment, the microbial population is exposed (prior to the method or at any stage of the method) to a selective pressure. For example, exposure of the microorganisms to pasteurisation before their addition to a plant growth medium (preferably sterile) is likely to enhance the probability that the plants selected for a desired trait will be associated with spore-forming microbes that can more easily survive in adverse conditions, in commercial storage, or if applied to seed as a coating, in an adverse environment.

In certain embodiments, as mentioned herein before, the microorganism(s) may be used in crude form and need not be isolated from a plant or a media. For example, plant material or growth media which includes the microorganisms identified to be of benefit to a selected plant may be obtained and used as a crude source of microorganisms for the next round of the method or as a crude source of microorganisms at the conclusion of the method. For example, whole plant material could be obtained and optionally processed, such as mulched or crushed. Alternatively, individual tissues or parts of selected plants (such as leaves, stems, roots, and seeds) may be separated from the plant and optionally processed, such as mulched or crushed. In certain embodiments, one or more part of a plant which is associated with the second set of one or more microorganisms may be removed from one or more selected plants and, where any successive repeat of the method is to be conducted, grafted on to one or more plant used in any step of the plant breeding methods.

Plants that are Able to Benefit from the Application of the Disclosed Microbes, Consortia, and Compositions Comprising the Same Any number of a variety of different plants, including mosses and lichens and algae, may be used in the methods of the disclosure. In embodiments, the plants have economic, social, or environmental value. For example, the plants may include those used as: food crops, fiber crops, oil crops, in the forestry industry, in the pulp and paper industry, as a feedstock for biofuel production, and as ornamental plants.

In other embodiments, the plants may be economically, socially, or environmentally undesirable, such as weeds. The following is a list of non-limiting examples of the types of plants the methods of the disclosure may be applied to:

Food Crops:

Cereals e.g maize, rice, wheat, barley, *sorghum*, millet, oats, rye, triticale, and buckwheat;

leafy vegetables e.g. brassicaceous plants such as cabbages, broccoli, bok choy, rocket; salad greens such as spinach, cress, and lettuce;

fruiting and flowering vegetables e.g. avocado, sweet corn, artichokes; curcubits squash, cucumbers, melons, courgettes, pumpkins; solanaceous vegetables/fruits e.g. tomatoes, eggplant, and capsicums;

podded vegetables e.g. groundnuts, peanuts, peas, soybeans, beans, lentils, chickpea, okra;

bulbed and stem vegetables e.g. asparagus, celery, *Allium* crops e.g garlic, onions, and leeks;

roots and tuberous vegetables e.g. carrots, beet, bamboo shoots, cassava, yams, ginger, Jerusalem artichoke, parsnips, radishes, potatoes, sweet potatoes, taro, turnip, and wasabi;

sugar crops including sugar beet (*Beta vulgaris*), sugar cane (*Saccharum officinarum*);

crops grown for the production of non-alcoholic beverages and stimulants e.g. coffee, black, herbal, and green teas, cocoa, marijuana, and tobacco;

fruit crops such as true berry fruits (e.g. kiwifruit, grape, currants, gooseberry, guava, feijoa, pomegranate), citrus fruits (e.g. oranges, lemons, limes, grapefruit), epigynous fruits (e.g. bananas, cranberries, blueberries), aggregate fruit (blackberry, raspberry, boysenberry), multiple fruits (e.g. pineapple, fig), stone fruit crops (e.g. apricot, peach, cherry, plum), pip-fruit (e.g. apples, pears) and others such as strawberries, sunflower seeds;

culinary and medicinal herbs e.g. rosemary, basil, bay laurel, coriander, mint, dill, *Hypericum*, foxglove, alovera, rosehips, and cannabis;

crop plants producing spices e.g. black pepper, cumin cinnamon, nutmeg, ginger, cloves, saffron, cardamom, mace, paprika, masalas, star anise;

crops grown for the production of nuts e.g. almonds and walnuts, Brazil nut, cashew nuts, coconuts, chestnut, macadamia nut, pistachio nuts; peanuts, pecan nuts;

crops grown for production of beers, wines and other alcoholic beverages e.g grapes, and hops;

oilseed crops e.g. soybean, peanuts, cotton, olives, sunflower, sesame, lupin species and brassicaeous crops (e.g. canola/oilseed rape); and, edible fungi e.g. white mushrooms, Shiitake and oyster mushrooms;

Plants Used in Pastoral Agriculture:

legumes: *Trifolium* species, *Medicago* species, and *Lotus* species; White clover (*T. repens*); Red clover (*T. pratense*); Caucasian clover (*T. ambigum*); subterranean clover (*T. subterraneum*); Alfalfa/Lucerne (*Medicago sativum*); annual medics; barrel medic; black medic; Sainfoin (*Onobrychis viciifolia*); Birdsfoot trefoil (*Lotus corniculatus*); Greater Birdsfoot trefoil (*Lotus pedunculatus*);

seed legumes/pulses including Peas (*Pisum sativum*), Common bean (*Phaseolus vulgaris*), Broad beans (*Vicia faba*), Mung bean (*Vigna radiata*), Cowpea (*Vigna unguiculata*), Chick pea (*Cicer arietum*), Lupins (*Lupinus* species); Cereals including Maize/corn (*Zea mays*), Sorghum (*Sorghum* spp.), Millet (*Panicum miliaceum, P. sumatrense*), Rice (*Oryza sativa indica, Oryza sativa japonica*), Wheat (*Triticum sativa*), Barley (*Hordeum vulgare*), Rye (*Secale cereale*), Triticale (*Triticum X Secale*), Oats (*Avena sativa*);

Forage and Amenity grasses: Temperate grasses such as *Lolium* species; *Festuca* species; *Agrostis* spp., Perennial ryegrass (*Lolium perenne*); hybrid ryegrass (*Lolium hybridum*); annual ryegrass (*Lolium multiflorum*), tall fescue (*Festuca arundinacea*); meadow fescue (*Festuca pratensis*); red fescue (*Festuca rubra*); *Festuca ovina; Festuloliums* (*Lolium X Festuca crosses*); Cocksfoot (*Dactylis glomerata*); Kentucky bluegrass *Poa pratensis; Poa palustris; Poa nemoralis; Poa trivialis; Poa compresa; Bromus* species; *Phalaris* (*Phleum* species); *Arrhenatherum elatius; Agropyron* species; *Avena strigosa; Scoria italic;*

Tropical grasses such as: *Phalaris* species; *Brachiaria* species; *Eragrostis* species; *Panicum* species; Bahai grass (*Paspalum notatum*); *Brachypodium* species; and, grasses used for biofuel production such as Switchgrass (*Panicum virgatum*) and *Miscanthus* species;

Fiber Crops:

cotton, hemp, jute, coconut, sisal, flax (*Linum* spp.), New Zealand flax (*Phormium* spp.); plantation and natural forest species harvested for paper and engineered wood fiber products such as coniferous and broadleafed forest species;

Tree and Shrub Species Used in Plantation Forestry and Bio-Fuel Crops:

Pine (*Pinus* species); Fir (*Pseudotsuga* species); Spruce (*Picea* species); Cypress (*Cupressus* species); Wattle (*Acacia* species); Alder (*Alnus* species); Oak species (*Quercus* species); Redwood (*Sequoiadendron* species); willow (*Salix* species); birch (*Betula* species); Cedar (*Cedurus* species); Ash (*Fraxinus* species); Larch (*Larix* species); Eucalyptus species; Bamboo (*Bambuseae* species) and Poplars (*Populus* species).

Plants Grown for Conversion to Energy, Biofuels or Industrial Products by Extractive, Biological, Physical or Biochemical Treatment:

Oil-producing plants such as oil palm, jatropha, soybean, cotton, linseed; Latex-producing plants such as the Para Rubber tree, *Hevea brasiliensis* and the Panama Rubber Tree *Castilla elastica*; plants used as direct or indirect feedstocks for the production of biofuels i.e. after chemical, physical (e.g. thermal or catalytic) or biochemical (e.g. enzymatic pre-treatment) or biological (e.g. microbial fermentation) transformation during the production of biofuels, industrial solvents or chemical products e.g, ethanol or butanol, propane dials, or other fuel or industrial material including sugar crops (e.g. beet, sugar cane), starch producing crops (e.g. C3 and C4 cereal crops and tuberous crops), cellulosic crops such as forest trees (e.g. Pines, Eucalypts) and Graminaceous and Poaceous plants such as bamboo, switch grass, *miscanthus*; crops used in energy, biofuel or industrial chemical production via gasification and/or microbial or catalytic conversion of the gas to biofuels or other industrial raw materials such as solvents or plastics, with or without the production of biochar (e.g. biomass crops such as coniferous, eucalypt, tropical or broadleaf forest trees, graminaceous and poaceous crops such as bamboo, switch grass, *miscanthus*, sugar cane, or hemp or softwoods such as poplars, willows; and, biomass crops used in the production of biochar;

Crops Producing Natural Products Useful for the Pharmaceutical. Agricultural Nutraceutical and Cosmeceutical Industries:

crops producing pharmaceutical precursors or compounds or nutraceutical and cosmeceutical compounds and materials for example, star anise (shikimic acid), Japanese knotweed (resveratrol), kiwifruit (soluble fiber, proteolytic enzymes);

Floricultural, Ornamental and Amenity Plants Grown for their Aesthetic or Environmental Properties:

Flowers such as roses, tulips, chrysanthemums;

Ornamental shrubs such as *Buxus, Hebe, Rosa, Rhododendron, Hedera*

Amenity plants such as *Platanus, Choisya, Escallonia, Euphorbia, Carex*

Mosses such as *sphagnum* moss

Plants Grown for Bioremediation:

*Helianthus, Brassica, Salix, Populus, Eucalyptus*

Hybrid and GM Plant Improvement

In certain aspects, the microbes of the present disclosure are applied to hybrid plants to increase beneficial traits of said hybrids. In other aspects, the microbes of the present disclosure are applied to genetically modified plants to increase beneficial traits of said GM plants. The microbes taught herein are able to be applied to hybrids and GM plants and thus maximize the elite genetics and trait technologies of these plants.

It should be appreciated that a plant may be provided in the form of a seed, seedling, cutting, propagule, or any other plant material or tissue capable of growing. In one embodiment the seed may be surface-sterilised with a material such as sodium hypochlorite or mercuric chloride to remove surface-contaminating microorganisms. In one embodiment, the propagule is grown in axenic culture before being placed in the plant growth medium, for example as sterile plantlets in tissue culture.

Methods of Application

The microorganisms may be applied to a plant, seedling, cutting, propagule, or the like and/or the growth medium containing said plant, using any appropriate technique known in the art.

However, by way of example, an isolated microbe, consortia, or composition comprising the same may be applied to a plant, seedling, cutting, propagule, or the like, by spraying or dusting.

In another embodiment, the isolated microbe, consortia, or composition comprising the same may applied directly to a plant seed prior to sowing.

In another embodiment, the isolated microbe, consortia, or composition comprising the same may applied directly to a plant seed, as a seed coating.

In one embodiment of the present disclosure, the isolated microbe, consortia, or composition comprising the same is supplied in the form of granules, or plug, or soil drench that is applied to the plant growth media.

In other embodiments, the the isolated microbe, consortia, or composition comprising the same are supplied in the form of a foliar application, such as a foliar spray or liquid composition. The foliar spray or liquid application may be applied to a growing plant or to a growth media, e.g. soil.

In another embodiment, the isolated microbe, consortia, or composition comprising the same may be formulated into granules and applied alongside seeds during planting. Or the granules may be applied after planting. Or the granules may be applied before planting.

In some embodiments, the isolated microbe, consortia, or composition comprising the same are administered to a plant or growth media as a topical application and/or drench application to improve crop growth, yield, and quality. The topical application may be via utilization of a thy mix or powder or dusting composition or may be a liquid based formulation.

In embodiments, the the isolated microbe, consortia, or composition comprising the same can be formulated as: (1) solutions; (2) wettable powders; (3) dusting powders; (4) soluble powders; (5) emulsions or suspension concentrates; (6) seed dressings or coatings, (7) tablets; (8) water-dispersible granules; (9) water soluble granules (slow or fast release); (10) microencapsulated granules or suspensions; and (11) as irrigation components, among others. In in certain aspects, the compositions may be diluted in an aqueous medium prior to conventional spray application. The compositions of the present disclosure can be applied to the soil, plant, seed, rhizosphere, rhizosheath, or other area to which it would be beneficial to apply the microbial compositions. Further still, ballistic methods can be utilized as a means for introducing endophytic microbes.

In aspects, the compositions are applied to the foliage of plants. The compositions may be applied to the foliage of plants in the form of an emulsion or suspension concentrate, liquid solution, or foliar spray. The application of the compositions may occur in a laboratory, growth chamber, greenhouse, or in the field.

In another embodiment, microorganisms may be inoculated into a plant by cutting the roots or stems and exposing the plant surface to the microorganisms by spraying, dipping, or otherwise applying a liquid microbial suspension, or gel, or powder.

In another embodiment, the microorganisms may be injected directly into foliar or root tissue, or otherwise inoculated directly into or onto a foliar or root cut, or else into an excised embryo, or radicle, or coleoptile. These inoculated plants may then be further exposed to a growth media containing further microorganisms; however, this is not necessary.

In other embodiments, particularly where the microorganisms are unculturable, the microorganisms may be transferred to a plant by any one or a combination of grafting, insertion of explants, aspiration, electroporation, wounding, root pruning, induction of stomatal opening, or any physical, chemical or biological treatment that provides the opportunity for microbes to enter plant cells or the intercellular space. Persons of skill in the art may readily appreciate a number of alternative techniques that may be used.

In one embodiment, the microorganisms infiltrate parts of the plant such as the roots, stems, leaves and/or reproductive plant parts (become endophytic), and/or grow upon the surface of roots, stems, leaves and/or reproductive plant parts (become epiphytic) and/or grow in the plant rhizosphere. In one embodiment, the microorganisms form a symbiotic relationship with the plant.

EXAMPLES

I. Increased Yield in Agriculturally Important Crops

In certain embodiments of the disclosure, the present methods aim to increase the yields for a given crop.

The methodologies presented herein based upon utilizing the disclosed isolated microbes, consortia, and compositions comprising the same have the potential to increase the yield of important agricultural crops. These yield increases can be realized without the need for further fertilizer addition.

Example 1: Increasing Ryegrass Biomass with Isolated Microbes and Microbial Consortia A. Seed Treatment with Isolated Microbe In this example, an isolated microbe from Tables 1-3 will be applied as a seed coating to seeds of ryegrass (*Lolium perenne*). Upon applying the isolated microbe as a seed coating, the ryegrass will be planted and cultivated in the standard manner.

A control plot of ryegrass seeds, which did not have the isolated microbe applied as a seed coating, will also be planted.

It is expected that the ryegrass plants grown from the seeds treated with the seed coating will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

B. Seed Treatment with Microbial Consortia

In this example, a microbial consortium, comprising at least two microbes from Tables 1-3 will be applied as a seed coating to seeds of ryegrass (*Lolium perenne*). Upon applying the microbial consortium as a seed coating, the ryegrass will be planted and cultivated in the standard manner.

A control plot of ryegrass seeds, which did not have the microbial consortium applied as a seed coating, will also be planted.

It is expected that the ryegrass plants grown from the seeds treated with the seed coating will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

C. Treatment with Agricultural Composition Comprising Isolated Microbe

In this example, an isolated microbe from Tables 1-3 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

D. Treatment with Agricultural Composition Comprising Microbial Consortia

In this example, a microbial consortium, comprising at least two microbes from Tables 1-3 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiably higher biomass than the control ryegrass plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

Example 2: Increasing Maize Biomass with Isolated Microbes and Microbial Consortia A. Seed Treatment with Isolated Microbe In this example, an isolated microbe from Tables 1-3 will be applied as a seed coating to seeds of corn (Zea mays). Upon applying the isolated microbe as a seed coating, the corn will be planted and cultivated in the standard manner.

A control plot of corn seeds, which did not have the isolated microbe applied as a seed coating, will also be planted.

It is expected that the corn plants grown from the seeds treated with the seed coating will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

B. Seed Treatment with Microbial Consortia

In this example, a microbial consortium, comprising at least two microbes from Tables 1-3 will be applied as a seed coating to seeds of corn (Zea mays) Upon applying the microbial consortium as a seed coating, the corn will be planted and cultivated in the standard manner.

A control plot of corn seeds, which did not have the microbial consortium applied as a seed coating, will also be planted.

It is expected that the corn plants grown from the seeds treated with the seed coating will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

C. Treatment with Agricultural Composition Comprising Isolated Microbe

In this example, an isolated microbe from Tables 1-3 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

D. Treatment with Agricultural Composition Comprising Microbial Consortia

In this example, a microbial consortium, comprising at least two microbes from Tables 1-3 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiably higher biomass than the control corn plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

Example 3: Increasing Soybean Biomass with Isolated Microbes and Microbial Consortia A. Seed Treatment with Isolated Microbe In this example, an isolated microbe from Tables 1-3 will be applied as a seed coating to seeds of soybean (*Glycine max*). Upon applying the isolated microbe as a seed coating, the soybean will be planted and cultivated in the standard manner.

A control plot of soybean seeds, which did not have the isolated microbe applied as a seed coating, will also be planted.

It is expected that the soybean plants grown from the seeds treated with the seed coating will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

B. Seed Treatment with Microbial Consortia

In this example, a microbial consortium, comprising at least two microbes from Tables 1-3 will be applied as a seed coating to seeds of soybean (*Glycine max*). Upon applying the microbial consortium as a seed coating, the soybean will be planted and cultivated in the standard manner.

A control plot of soybean seeds, which did not have the microbial consortium applied as a seed coating, will also be planted.

It is expected that the soybean plants grown from the seeds treated with the seed coating will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

C. Treatment with Agricultural Composition Comprising Isolated Microbe

In this example, an isolated microbe from Tables 1-3 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

D. Treatment with Agricultural Composition Comprising Microbial Consortia

In this example, a microbial consortium, comprising at least two microbes from Tables 1-3 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiably higher biomass than the control soybean plants.

The biomass from the treated plants may be about 1-10% higher, 10-20% higher, 20-30% higher, 30-40% higher, 40-50% higher, 50-60% higher, 60-70% higher, 70-80% higher, 80-90% higher, or more.

The biomass from the treated plants may equate to about a 1 bushel per acre increase over the controls, or a 2 bushel per acre increase, or a 3 bushel per acre increase, or a 4 bushel per acre increase, or a 5 bushel per acre increase, or more.

In some aspects, the biomass increase is statistically significant. In other aspects, the biomass increase is not statistically significant, but is still quantifiable.

Example 4: Modifying Wheat Seedling Biomass with Isolated Microbes

A. Seed Treatment with Isolated Microbe

Figure 5:
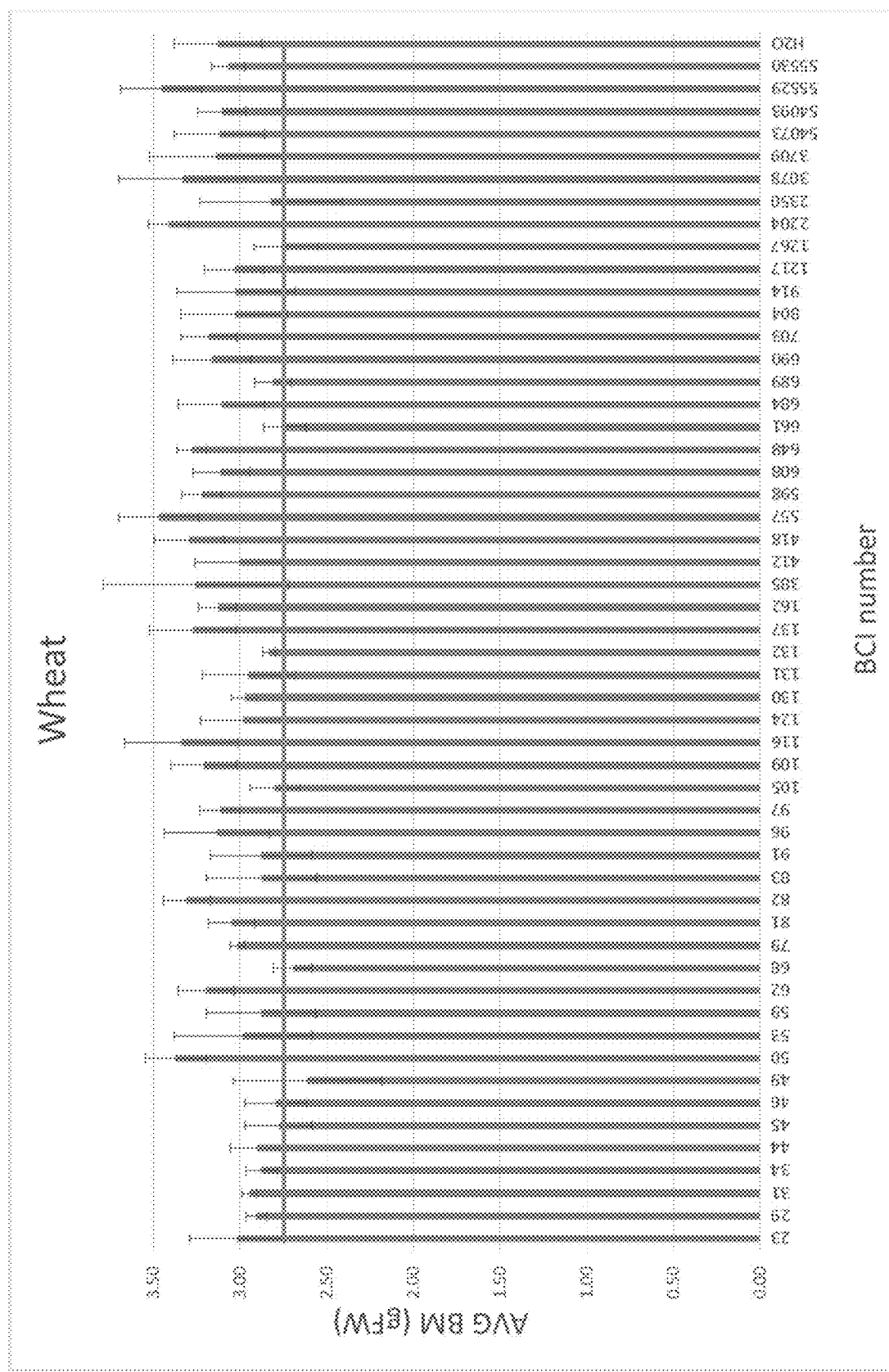
FIG. 5 shows a graphic representation of the average total biomass of wheat, in grams of fresh weight, at seven days post inoculation with individual microbial strains (BCI).

In this example, wheat seeds were inoculated with individual microbial strains (BCIs), and allowed to germinate (FIG. 5).

The seeds were inoculated and placed on wet paper towels and rolled. The rolls were then incubated at 25° C. in plastic bins covered with wet towels. Each strain appearing in FIG. 5 was tested in triplicate, with 20 seeds per replicate test.

Total biomass was measured at seven days post treatment. An uninoculated 'water' control treatment was run and measured simultaneously. The solid line parallel to the x axis and bisecting the bars near the top of the y-axis of FIG. 5 represents uninoculated control seeds. Some of the inoculated strains revealed relative increases in biomass at seven days post inoculation (DPI) compared to untreated control in vitro.

Table 11 provides a breakout of the biomass increase in wheat having been inoculated as described above, relative to a water-only treatment control (H2O) and an untreated (Unt) control. The two columns immediately to the right of the species reflect the percentage increase over control (% IOC) for the water-only treatment control and the untreated control. Both increases and decreases in the biomasses are reflected in the data of table 11. A smaller plant reflects potential for in-field conservation of nutrients and water where these resources may be limited by drought or local conditions, thus decreases are hypothesized to be yield relevant.

The results demonstrated that ~19 strains caused a relative increase in total biomass of wheat at seven days post inoculation (DPI) compared to the water-only and untreated controls in vitro. Eight strains showed greater than a 5% increase over both controls, whereas 19 strains showed greater than a 5% decrease in biomass over the water control.

TABLE 11

| Strain | Species | % IOC UNT | % IOC H2O |
|---|---|---|---|
| 557 | Novosphingobium resinovorum | 26.2 | 10.9 |
| 55529 | Pantoea vagans | 25.7 | 10.4 |
| 2204 | Duganella violaceinigra | 24.3 | 9.2 |
| 50 | Exiguobacterium aurantiacum | 22.7 | 7.8 |
| 116 | Exiguobacterium sibiricum | 21.5 | 6.7 |
| 3078 | Variovorax ginsengisoli | 21.3 | 6.6 |
| 82 | Novosphingobium sediminicola | 20.4 | 5.7 |
| 418 | Paenibacillus glycanilyticus | 19.9 | 5.3 |
| 648 | Acidovorax soli | 19.3 | 4.8 |
| 137 | Variovorax ginsengisoli | 19.0 | 4.6 |
| 385 | Achromobacter spanius | 18.6 | 4.1 |
| 598 | Pedobacter rhizosphaerae | 17.2 | 3.0 |
| 109 | Chitinophaga terrae | 16.7 | 2.5 |
| 62 | Arthrobacter cupressi | 16.4 | 2.2 |
| 703 | Bosea thiooxidans | 15.8 | 1.7 |
| 690 | Acidovorax soli | 15.2 | 1.2 |
| 3709 | Novosphingobium resinovorum | 14.2 | 0.3 |
| 96 | Dyadobacter soli | 14.1 | 0.2 |
| 162 | Herbaspirillum chlorophenolicum | 13.9 | 0.1 |
| H2O | | 13.8 | 0.0 |
| 97 | Massilia albidiflava | 13.5 | −0.3 |
| 54073 | Stenotrophomonas maltophilia | 13.5 | −0.3 |
| 608 | Novosphingobium lindaniclasticum | 13.2 | −0.5 |
| 684 | Novosphingobium lindaniclasticum | 13.1 | −0.7 |
| 54093 | Rhodococcus erythropolis | 13.0 | −0.8 |
| 55530 | Pseudomonas oryzihabitans | 11.6 | −1.9 |
| 81 | Exiguobacterium sp. | 10.9 | −2.6 |
| 804 | Pseudomonas jinjuensis | 10.4 | −3.0 |
| 1217 | Massilia niastensis | 10.4 | −3.0 |
| 914 | Shingopyxis alaskensis | 10.1 | −3.3 |
| 23 | Exiguobacterium acetylicum | 9.8 | −3.5 |
| 79 | Chitinophaga terrae | 9.7 | −3.6 |
| 412 | Sphingopyxis alaskensis | 9.3 | −4.0 |
| 124 | Delftia lacustris | 8.7 | −4.5 |
| 53 | Pedobacter terrae | 8.6 | −4.6 |
| 130 | Novosphingobium sediminicola | 8.4 | −4.8 |
| 131 | Ensifer adhaerens | 7.4 | −5.7 |
| 31 | Duganella radicis | 7.3 | −5.8 |
| 29 | Rahnella aquatilis | 5.7 | −7.2 |
| 44 | Kosakonia radicincitans | 5.6 | −7.3 |
| 59 | Arthrobacter cupressi | 4.7 | −8.0 |
| 83 | Exiguobacterium acetylicum | 4.7 | −8.0 |
| 91 | Pedobacter terrae | 4.7 | −8.0 |
| 34 | Rhizobium rhizoryzae | 4.7 | −8.1 |
| 132 | Microbacterium oleivorans | 3.0 | −9.5 |
| 2350 | Delftia lacustris | 2.8 | −9.7 |
| 689 | Bosea robiniae | 2.3 | −10.1 |
| 105 | Duganella radicis | 1.9 | −10.5 |
| 46 | Rhizobium sp. | 1.7 | −10.7 |
| 45 | Chryseobacterium daecheongense | 1.2 | −11.1 |
| UNT | | 0.0 | −12.2 |
| 661 | Rhizobium rhizoryzae | −0.3 | −12.4 |
| 1267 | Bosea eneae | −0.4 | −12.5 |
| 68 | Dyadobacter soli | −1.8 | −13.8 |
| 49 | Achromobacter pulmonis | −5.0 | −16.5 |

Example 5: Increasing Root and Shoot Length of Maize, and Tomato with Isolated Microbes A. Seed Treatment with Isolated Microbe In this example, seeds of maize, wheat, and tomato were inoculated with individual microbial strains (BDNZ strains), and allowed to germinate.

The seeds were inoculated and placed on wet paper towels and rolled. The rolls were then incubated at 25° C. in sealed plastic bags, Each strain appearing in table 12 was tested in germination tests in duplicate, with 30 seeds per replicate test for wheat and maize and 50 seeds for tomato.

Root length and shoot length (RL and SL) were measured at four days post treatment. A control treatment of seeds with water and the absence of a microbial inoculant of the present disclosure. Some of the inoculated strains revealed relative increases in root and/or shoot length at four days point inoculation (DPI) compared to untreated control.

Figure 6:
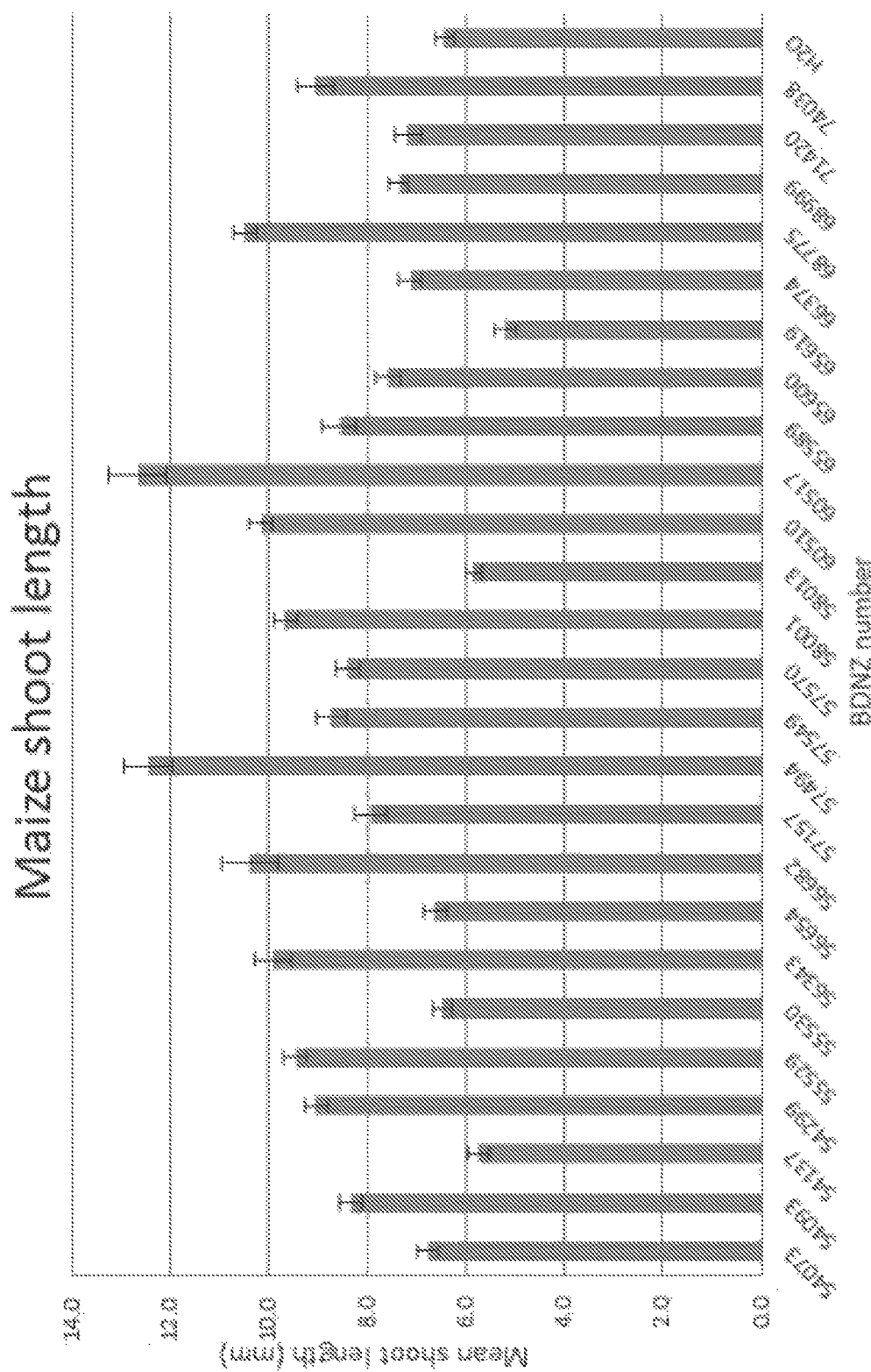
FIG. 6 shows a graphic representation of the average shoot length, in millimeters, of maize at 4 days post treatment with individual microbial strains. Maize seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 30 seeds each. Shoot length was measured at 4 days post inoculation (DPI). Standard error bars are shown. Results show that while germination rates were good for all strains tested, some strains caused a relative increase in shoot length at 4 days post inoculation (DPI) compared to the water control in vivo.
Figure 7:
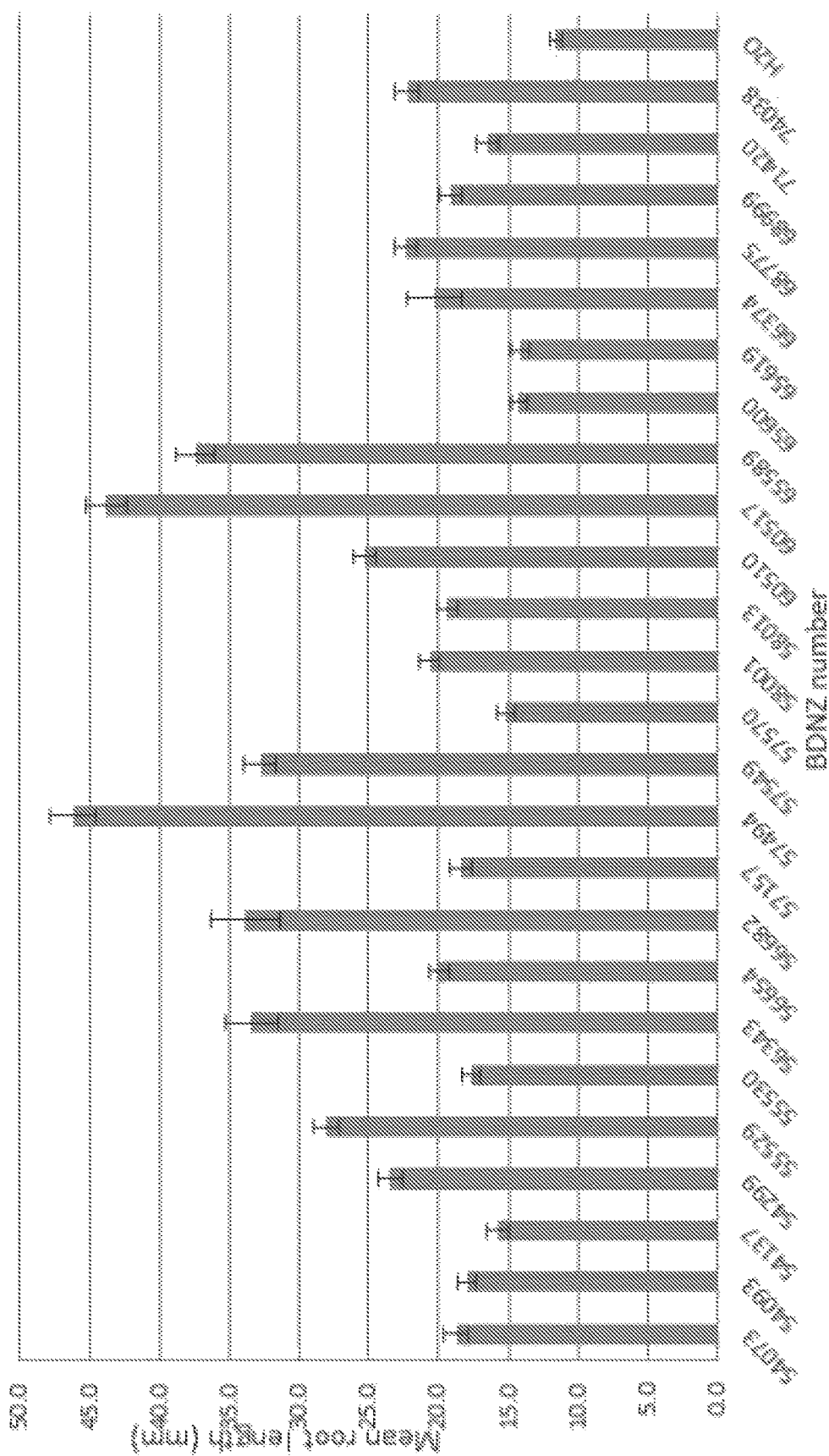
FIG. 7 shows a graphic representation of the average root length, in millimeters, of maize at 4 days post treatment with individual microbial strains. Maize seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 30 seeds each. Root length was measured at 4 days post inoculation (DPI). Standard error bars are shown. Results show that while germination rates were good for all strains tested, some strains caused a relative increase in root length at 4 days post inoculation (DPI) compared to the water control in vivo.

Each strain applied to maize seed was tested in duplicates of 30 seeds each. Results show that while germination rates were good for all strains tested, and some strains caused a relative increase in root and/or shoot length at 4 days post inoculation (DPI) compared to the water control in vitro (See FIGS. 6 and 7).

Figure 8:
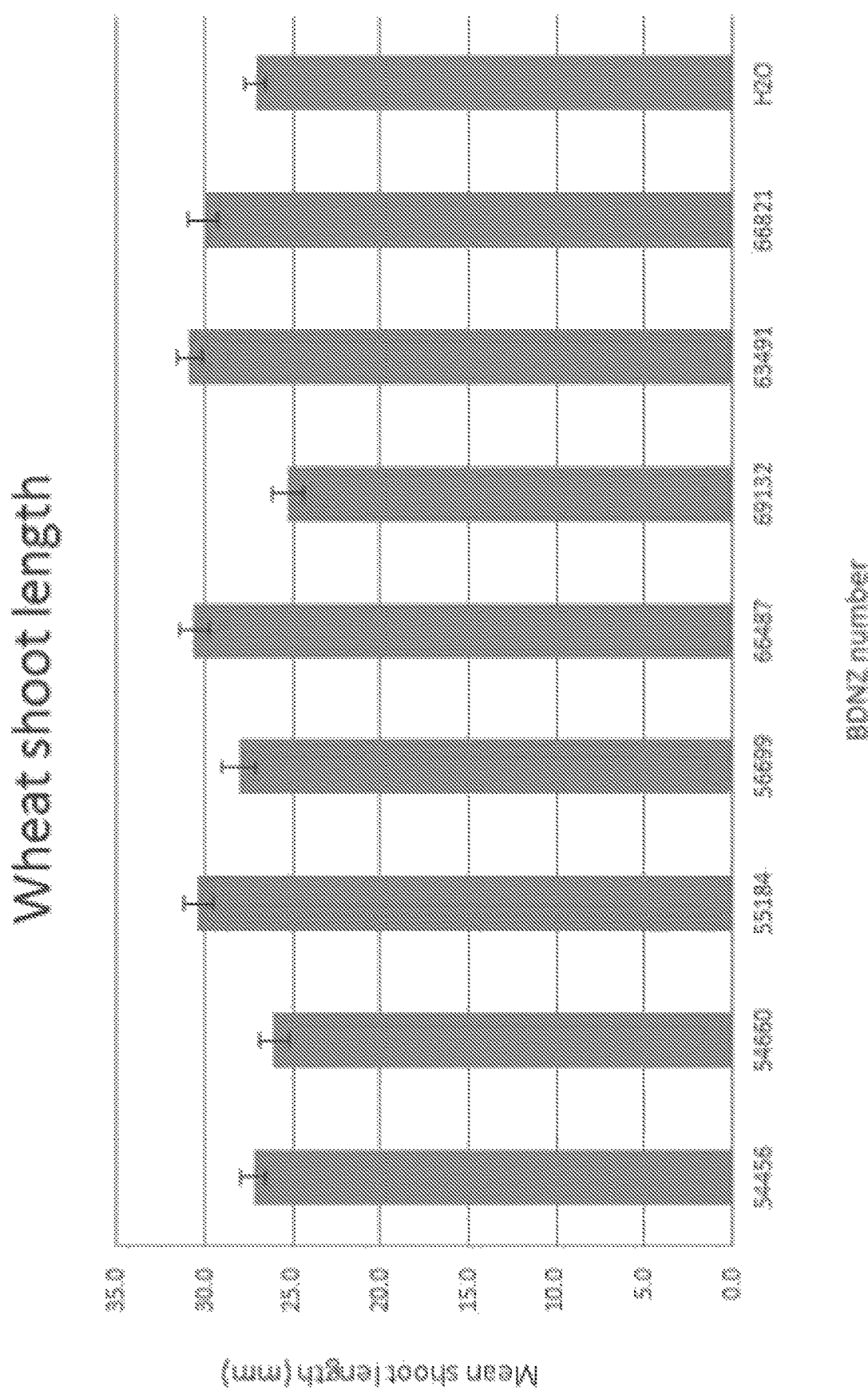
FIG. 8 shows a graphic representation of the average shoot length, in millimeters, of wheat at 4 days post treatment with individual microbial strains. Wheat seeds were inoculated with individual microbial strains (BDNZ numbers) and subjected to a germination test. Seed were inoculated, placed on wet paper towels and roiled. Rolls were incubated in sealed plastic bags at 25° C. Each individual strain was tested in duplicates of 30 seeds each. Shoot length was measured at 4 days post treatment. Results show that germination rates were good for all strains tested (>90%) and some strains caused a relative increase in shoot length at 4 days post inoculation (DPI) compared to the water control in vitro.
Figure 9:
FIG. 9 shows a graphic representation of the average root length, in millimeters, of wheat at 4 days post treatment with individual microbial strains. Wheat seeds were inoculated with individual microbial strains (BDNZ numbers) and subjected to a germination test. Seed were inoculated, placed on wet paper towels and rolled. Rolls were incubated in sealed plastic bags at 25° C. Each individual strain was tested in duplicates of 30 seeds each. Root length was measured at 4 days post treatment. Results show that germination rates were good for all strains tested (>90%) and some strains caused a relative increase in root length at 4 days post inoculation (DPI) compared to the water control in vitro.

Each strain applied to wheat seed was tested in duplicates of 30 seeds each. Root and shoot length were measured at 4 days post treatment. Results show that germination rates were good for all strains tested (>90%), and some strains caused a relative increase in root and/or shoot length at 4 days post inoculation (DPI) compared to the water control in vitro (See FIGS. 8 and 9).

Figure 10:
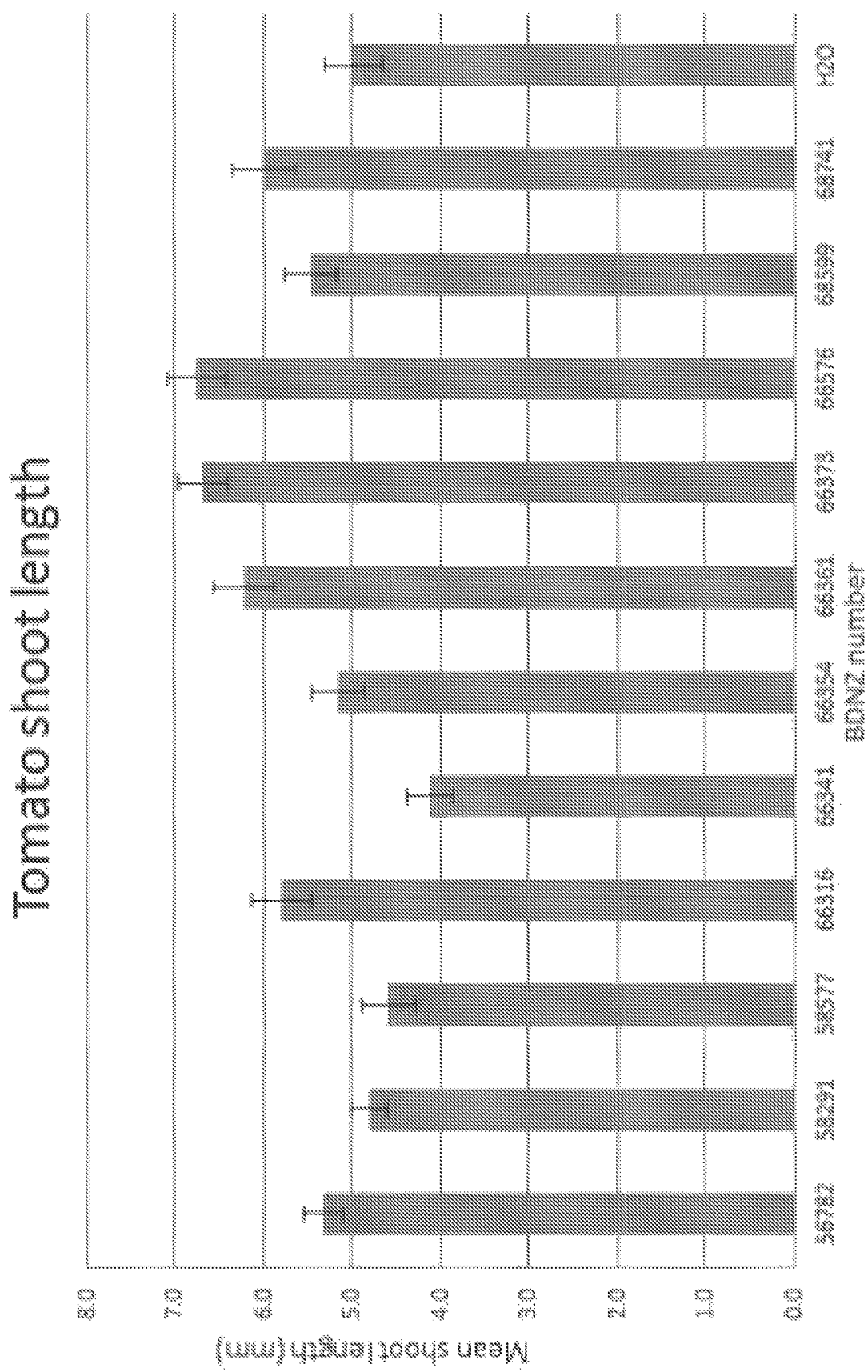
FIG. 10 shows a graphic representation of the average shoot length, in millimeters, of tomato at 4 days post treatment with individual microbial strains. Tomato seeds were inoculated with individual microbial strains (BDNZ numbers) and subjected to a germination test. Seeds were inoculated, placed on wet paper towels and rolled. Rolls were incubated in sealed plastic bags at 25° C. Each individual strain was tested in duplicates of 50 seeds each. Shoot length was measured at 4 days post treatment. The mean length of shoots of the water control seed can be seen in the far right bar labelled "H2O". Results show that germination rates were good for all strains tested and some strains caused a relative increase in shoot length at 4 days post inoculation (DPI) compared to the water control in vitro.

Each strain applied to tomato seed was tested in duplicates of 50 seeds each. Root and shoot length were measured at 4 days post inoculation (DPI). Results show that germination rates were good for all strains tested, and some strains caused a relative increase in root and/or shoot length at 4 days post inoculation (DPI) compared to the water control in vitro (See FIGS. 10 and 11).

Table 12 provides a breakout of the root and shoot length increase (in mm) after inoculation as described above, relative to a water-only treatment control (H2O). The columns immediately to the right of the species reflect the percentage increase over control (% IOC) for the water-only treatment control. Both increases and decreases are reflected in the data. A smaller plant reflects potential for in-field conservation of nutrients and water where these resources may be limited by drought or local conditions, thus decreases are hypothesized to be yield relevant.

The results demonstrated that a number of strains isolated from superior plants caused a significant increase over the water control in root and/or shoot length (p<0.1, Fisher's LSD) at four days post inoculation (DPI). Twenty strains isolated from superior plants caused a significant increase over the water control in maize root length and 19 caused a significant increase in maize shoot length. Four strains caused a significant increase over control in root and shoot length of wheat. Four strains caused a significant increase over control in root and shoot length of tomato.

TABLE 2

| Strain | Crop | Species | % IOC RL | % IOC SL |
|---|---|---|---|---|
| 54073 | Maize | Stenotrophomonas maltophilia | 61.8 | 5 |
| 54093 | Maize | Rhodococcus erythropolis | 54.6 | 29.7 |
| 54137 | Maize | Pantoea agglomerans | 36.1 | −10.5 |
| 54299 | Maize | Rhodococcus erythropolis | 102.7 | 40.7 |
| 55529 | Maize | Pantoea agglomerans | 142.4 | 47.3 |
| 55530 | Maize | Pseudomonas oryzihabitans | 52.3 | 0.6 |
| 56343 | Maize | Chitinophaga arvensicola | 188.6 | 54.3 |
| 56654 | Maize | Paenibacillus chronoitinus | 72.1 | 3.1 |
| 56682 | Maize | Paenibacillus chronoitinus | 192.5 | 61.8 |
| 57157 | Maize | Rahnella aquatilis | 58.5 | 23.2 |
| 57494 | Maize | Bosea minatitlanensis | 298.9 | 93.8 |
| 57549 | Maize | Luteibacter yoejuensis | 183 | 35.9 |
| 57570 | Maize | Caulobacter henricii | 30.5 | 30.6 |
| 58001 | Maize | Stenotrophomonas maltophilia | 78 | 50.5 |
| 58013 | Maize | Rahnella aquatilis | 67 | −9 |
| 60510 | Maize | Dyella ginsengisoli | 118 | 58.2 |
| 65017 | Maize | Frateuria sp. | 278.5 | 96.9 |
| 65589 | Maize | Novosphingobium rosa | 223 | 33.2 |
| 65600 | Maize | Herbaspirillum huttiense | 23 | 18 |
| 65619 | Maize | Novosphingobium rosa | 22.4 | −19.3 |
| 66374 | Maize | Albidiferax sp. | 75.3 | 10.9 |
| 68775 | Maize | Rhodoferax ferrireducens | 93 | 63.1 |
| 68999 | Maize | Chitinophaga arvensicola | 65.4 | 14.5 |
| 71420 | Maize | Luteibacter yoejuensis | 42.3 | 11.6 |
| 74038 | Maize | Pseudomonas oryzihabitans | 92.2 | 40.7 |
| 54456 | Wheat | Janthinobacterium sp. | 7.7 | 0.5 |

TABLE 2-continued

| Strain | Crop | Species | % IOC RL | % IOC SL |
|---|---|---|---|---|
| 54660 | Wheat | Paenibacillus amylolyticus | −4 | −3.9 |
| 55184 | Wheat | Massilia niastensis | 16.1 | 12.2 |
| 56699 | Wheat | Massilia niastensis | 0.8 | 3.6 |
| 66487 | Wheat | Flavobacterium saccharophilum | 7.2 | 13 |
| 69132 | Wheat | Flavobacterium glaciei | −10.2 | −6.8 |
| 63491 | Wheat | Janthinobacterium sp. | 10.2 | 13.9 |
| 66821 | Wheat | Polaromonas ginsengisoli | −3.1 | 11.1 |
| 56782 | Tomato | Sphingobium quisquiliarum | 14.1 | 7 |
| 58291 | Tomato | Duganella violaceinigra | 13.4 | −3.5 |
| 58577 | Tomato | Ramlibacter sp. | 5.6 | −8 |
| 66316 | Tomato | Paenibacillus amylolyticus | 28.1 | 16.2 |
| 66341 | Tomato | Calubacter henricii | −4.8 | −17.4 |
| 66354 | Tomato | Bosea minatitlanensis | 9.4 | 3.4 |
| 66361 | Tomato | Duganella violaceinigra | 34.9 | 24.6 |
| 66373 | Tomato | Polaromonas ginsengisoli | 23.5 | 34 |
| 66576 | Tomato | Sphingobium quisquilarum | 28.1 | 35.4 |
| 68599 | Tomato | Stenotrophomonas terrae | 15.9 | 9.6 |
| 68741 | Tomato | Stenotrophomonas terrae | 15.8 | 20.3 |

In table 12, the root and shoot length were assessed to evaluate the effect of the microbe treatments on early plant development. Both increases and decreases in biomass have been noted to reflect the possibility that decreases are hypothesized to be yield relevant; for example a smaller plant reflects potential for in-field conservation of nutrients and water where these may be limited by drought or local conditions. Results show that of all strains tested, some 40 strains caused a relative increase in root length at 4 days post inoculation (DPI) and 35 strains caused a relative increase in shoot length compared to water controls in vitro. Four tomato strains, three wheat strains and 17 maize strains caused a significant increase in both shoot length and root length (p<0.1, Fishers least squared difference).

II. Increased Drought Tolerance and $H_2O$ Use Efficiency in Agriculturally Important Crops In certain embodiments of the disclosure, the present methods aim to increase the drought tolerance and water use efficiency for a given crop.

The methodologies presented herein based upon utilizing the disclosed isolated microbes, consortia, and compositions comprising the same have the potential to increase the drought tolerance and water use efficiency of important agricultural crops. This will enable a more sustainable agricultural system and increase the regions of the world that are suitable for growing important crops.

Example 1: Increasing Ryegrass Drought Tolerance and $H_2O$ Use Efficiency with Isolated Microbes and Microbial Consortia A. Seed Treatment with Isolated Microbe In this example, an isolated microbe from Tables 1-3 will be applied as a seed coating to seeds of ryegrass (*Lolium perenne*). Upon applying the isolated microbe as a seed coating, the ryegrass will be planted and cultivated in the standard manner.

A control plot of ryegrass seeds, which did not have the isolated microbe applied as a seed coating, will also be planted.

It is expected that the ryegrass plants grown from the seeds treated with the seed coating will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

B. Seed Treatment with Microbial Consortia

In this example, a microbial consortium, comprising at least two microbes from Tables 1-3 will be applied as a seed coating to seeds of ryegrass (*Lolium perenne*). Upon applying the microbial consortium as a seed coating, the ryegrass will be planted and cultivated in the standard manner.

A control plot of ryegrass seeds, did not have the microbial consortium applied as a seed coating, will also be planted.

It is expected that the ryegrass plants grown from the seeds treated with the seed coating will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

C. Treatment with Agricultural Composition Comprising Isolated Microbe

In this example, an isolated microbe from Tables 1-3 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the with the agricultural composition will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

D. Treatment with Agricultural Composition Comprising Microbial Consortia

In this example, a microbial consortium, comprising at least two microbes from Tables 1-3 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the with the agricultural composition will exhibit a quantifiable and superior ability to tolerate drought conditions and/or exhibit superior water use efficiency, as compared to the control ryegrass plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

Example 2: Increasing Maize Drought Tolerance and $H_2O$ Use Efficiency with Isolated Microbes and Microbial Consortia A. Seed Treatment with Isolated Microbe In this example, an isolated microbe from Tables 1-3 will be applied as a seed coating to seeds of corn (*Zea mays*). Upon applying the isolated microbe as a seed coating, the corn will be planted and cultivated in the standard manner.

A control plot of corn seeds, which did not have the isolated microbe applied as a seed coating, will also be planted.

It is expected that the corn plants grown from the seeds treated with the seed coating will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

B. Seed Treatment with Microbial Consortia

In this example, a microbial consortium, comprising at least two microbes from Tables 1-3 will be applied as a seed coating to seeds of corn (*Zea mays*). Upon applying the microbial consortium as a seed coating, the corn will be planted and cultivated in the standard manner.

A control plot of corn seeds, which did not have the microbial consortium applied as a seed coating, will also be planted.

It is expected that the corn plants grown from the seeds treated with the seed coating will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

C. Treatment with Agricultural Composition Comprising Isolated Microbe

In this example, an isolated microbe from Tables 1-3 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate hulk tank on the planter and sprayed into the rows upon planting the corn seed.

A control plot of corn seeds, which are not administered the agricultural composition, will also be planted.

It is expected that the corn plants grown from the seeds treated with the with the agricultural composition will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

D. Treatment with Agricultural Composition Comprising Microbial Consortia

In this example, a microbial consortium, comprising at least two microbes from Tables 1-3 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the with the agricultural composition will exhibit a quantifiable and superior ability to tolerate drought conditions and/or exhibit superior water use efficiency, as compared to the control corn plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

Example 3: Increasing Soybean Drought Tolerance and H$_2$0 Use Efficiency with Isolated Microbes and Microbial Consortia A. Seed Treatment with Isolated Microbe In this example, an isolated microbe from Tables 1-3 will be applied as a seed coating to seeds of soybean (*Glycine max*). Upon applying the isolated microbe as a seed coating, the soybean will be planted and cultivated in the standard manner.

A control plot of soybean seeds, which did not have the isolated microbe applied as a seed coating, will also be planted.

It is expected that the soybean plants grown from the seeds treated with the seed coating will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

B. Seed Treatment with Microbial Consortia

In this example, a microbial consortium, comprising at least two microbes from Tables 1-3 will be applied as a seed coating to seeds of soybean (*Glycine max*). Upon applying the microbial consortium as a seed coating, the soybean will be planted and cultivated in the standard manner.

A control plot of soybean seeds, which did not have the microbial consortium applied as a seed coating, will also be planted.

It is expected that the soybean plants grown from the seeds treated with the seed coating will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

C. Treatment with Agricultural Composition Comprising Isolated Microbe

In this example, an isolated microbe from Tables 1-3 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into row. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the with the agricultural composition will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

D. Treatment with Agricultural Composition Comprising Microbial Consortia

In this example, a microbial consortium, comprising at least two microbes from Tables 1-3 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the with the agricultural composition will exhibit a quantifiable and superior ability to tolerate drought conditions and/or exhibit superior water use efficiency, as compared to the control soybean plants.

The drought tolerance and/or water use efficiency can be based on any number of standard tests from the art, e.g leaf water retention, turgor loss point, rate of photosynthesis, leaf color and other phenotypic indications of drought stress, yield performance, and various root morphological and growth patterns.

III. Increased Nitrogen Use Efficiency in Agriculturally Important Crops

In certain embodiments of the disclosure, the present methods aim to decrease the amount of nitrogen that must be deposited into a given agricultural system and yet achieve the same or better yields for a given crop.

The methodologies presented herein based upon utilizing the disclosed isolated microbes, consortia, and compositions comprising the same have the potential to reduce the amount of nitrogen fertilizer that is lost by farmers every year due to nitrogen leaching into the air, soil, and waterways. This will enable a more sustainable agricultural system that is still able to produce yield results consistent with today's agricultural expectations.

Example 1: Increasing Ryegrass NUE with Isolated Microbes and Microbial Consortia A. Seed Treatment with Isolated Microbe In this example, an isolated microbe from Tables 1-3 will be applied as a seed coating to seeds of ryegrass (*Lolium perenne*). Upon applying the isolated microbe as a seed coating, the ryegrass will be planted and cultivated in the standard manner.

A control plot of ryegrass seeds, which did not have the isolated microbe applied as a seed coating, will also be planted.

It is expected that the ryegrass plants grown from the seeds treated with the seed coating will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

B. Seed Treatment with Microbial Consortia

In this example, a microbial consortium, comprising at least two microbes from Tables 1-3 will be applied as a seed coating to seeds of ryegrass *Lolium perenne*). Upon applying the microbial consortium as a seed coating, the ryegrass will be planted and cultivated in the standard manner.

A control plot of ryegrass seeds, which did not have the microbial consortium applied as a seed coating, will also be planted.

It is expected that the ryegrass plants grown from the seeds treated with the seed coating will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

C. Treatment with Agricultural Composition Comprising Isolated Microbe

In this example, an isolated microbe from Tables 1-3 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

D. Treatment with Agricultural Composition Comprising Microbial Consortia

In this example, a microbial consortium, comprising at least two microbes from Tables 1-3 will be applied as an agricultural composition, administered to the ryegrass seed at the time of sowing.

For example, it is anticipated that a farmer will apply the agricultural composition to the ryegrass seeds simultaneously upon broadcasting said seeds into the field. This can be accomplished, for example, by applying the agricultural composition to a hopper or spreader, which contains the ryegrass seeds and which is configured to broadcast the same.

A control plot of ryegrass seeds, which are not administered the agricultural composition, will also be planted.

It is expected that the ryegrass plants grown from the seeds treated with the agricultural composition will exhibit a quantifiable and superior ability to utilize nitrogen, as compared to the control ryegrass plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

Example 2: Increasing Maize NUE with Isolated Microbes and Microbial Consortia

A. Seed Treatment with Isolated Microbe

In this example, an isolated microbe from Tables 1-3 will be applied as a seed coating to seeds of corn (*Zea mays*). Upon applying the isolated microbe as a seed coating, the corn will be planted and cultivated in the standard manner.

A control plot of corn seeds, which did not have the isolated microbe applied as a seed coating, will also be planted.

It is expected that the corn plants grown from the seeds treated with the seed coating will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

B. Seed Treatment with Microbial Consortia

In this example, a microbial consortium, comprising at least two microbes from Tables 1-3 will be applied as a seed coating to seeds of corn (*Zea mays*). Upon applying the microbial consortium as a seed coating, the corn will be planted and cultivated in the standard manner.

A control plot of corn seeds, which did not have the microbial consortium applied as a seed coating, will also be planted.

It is expected that the corn plants grown from the seeds treated with the seed coating will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

C. Treatment with Agricultural Composition Comprising Isolated Microbe

In this example, an isolated microbe from Tables 1-3 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

D. Treatment with Agricultural Composition Comprising Microbial Consortia

In this example, a microbial consortium, comprising at least two microbes from Tables 1-3 will be applied as an agricultural composition, administered to the corn seed at the time of sowing.

For example, it is anticipated that a farmer will apply the agricultural composition to the corn seeds simultaneously upon planting the seeds into the field. This can be accomplished, for example, by applying the agricultural composition to a hopper/bulk tank on a standard 16 row planter, which contains the corn seeds and which is configured to plant the same into rows. Alternatively, the agricultural composition can be contained in a separate bulk tank on the planter and sprayed into the rows upon planting the corn seed.

A control plot of corn seeds, which are not administered the agricultural composition, will also be planted.

It is expected that the corn plants grown from the seeds treated with the agricultural composition will exhibit a quantifiable and superior ability to utilize nitrogen, as compared to the control corn plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

Example 3: Increasing Soybean NUE with Isolated Microbes and Microbial Consortia A. Seed Treatment with Isolated Microbe In this example, an isolated microbe from Tables 1-3 will be applied as a seed coating to seeds of soybean (*Glycine max*). Upon applying the isolated microbe as a seed coating, the soybean will be planted and cultivated in the standard manner.

A control plot of soybean seeds, which did not have the isolated microbe applied as a seed coating, will also be planted.

It is expected that the soybean plants grown from the seeds treated with the seed coating will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

B. Seed Treatment with Microbial Consortia

In this example, a microbial consortium, comprising at least two microbes from Tables 1-3 will be applied as a seed coating to seeds of soybean (*Glycine max*). Upon applying the microbial consortium as a seed coating, the soybean will be planted and cultivated in the standard manner.

A control plot of soybean seeds, which did not have the microbial consortium applied as a seed coating, will also be planted.

It is expected that the soybean plants grown from the seeds treated with the seed coating will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

C. Treatment with Agricultural Composition Comprising Isolated Microbe

In this example, an isolated microbe from Tables 1-3 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

D. Treatment with Agricultural Composition Comprising Microbial Consortia

In this example, a microbial consortium, comprising at least two microbes from Tables 1-3 will be applied as an agricultural composition, administered to the soybean seed at the time of sowing.

For example, it is anticipated that a farmer will apply the agricultural composition to the soybean seeds simultaneously upon planting the seeds into the field. This can be accomplished, for example, by applying the agricultural composition to a hopper/bulk tank on a standard 16 row planter, which contains the soybean seeds and which is configured to plant the same into rows. Alternatively, the agricultural composition can be contained in a separate bulk tank on the planter and sprayed into the rows upon planting the soybean seed.

A control plot of soybean seeds, which are not administered the agricultural composition, will also be planted.

It is expected that the soybean plants grown from the seeds treated with the agricultural composition will exhibit a quantifiable and superior ability to utilize nitrogen, as compared to the control soybean plants.

The nitrogen use efficiency can be quantified by recording a measurable change in any of the main nitrogen metabolic pool sizes in the assimilation pathways (e.g., a measurable change in one or more of the following: nitrate, nitrite, ammonia, glutamic acid, aspartic acid, glutamine, asparagine, lysine, leucine, threonine, methionine, *glycine*, tryptophan, tyrosine, total protein content of a plant part, total nitrogen content of a plant part, and/or chlorophyll content), or where the treated plant is shown to provide the same or elevated biomass or harvestable yield at lower nitrogen fertilization levels compared to the control plant, or where the treated plant is shown to provide elevated biomass or harvestable yields at the same nitrogen fertilization levels compared to a control plant.

IV. Increased Metabolite Expression in Agriculturally Important Crops

In certain embodiments of the disclosure, the present methods aim to increase the production of a metabolite of interest for a given crop.

The methodologies presented herein based upon utilizing the disclosed isolated microbes, consortia, and compositions comprising the same have the potential to increase the production of a metabolite of interest for a given crop.

Example 1: Increasing Sugar Content in Basil with Isolated Microbes and Microbial Consortia A. Seed Treatment with Isolated Microbe In this example, an isolated microbe from Tables 1-3 will be applied as a seed coating to seeds of basil (*Ocium basilicum*). Upon applying the isolated microbe as a seed coating, the basil will be planted and cultivated in the standard manner.

A control plot of basil seeds, which did not have the isolated microbe applied as a seed coating, will also be planted.

It is expected that the basil plants grown from the seeds treated with the seed coating will exhibit a quantifiable increase in water-soluble carbohydrate content, as compared to the control basil plants.

B. Seed Treatment with Microbial Consortia

In this example, a microbial consortium, comprising at least two microbes from Tables 1-3 will be applied as a seed coating to seeds of basil (*Ocium basilicum*). Upon applying the microbial consortium as a seed coating, the basil will be planted and cultivated in the standard manner.

A control plot of basil seeds, which did not have the microbial consortium applied as a seed coating, will also be planted.

It is expected that the basil plants grown from the seeds treated with the seed coating will exhibit a quantifiable increase in water-soluble carbohydrate content, as compared to the control basil plants.

V. Synergistic Effect Achievable with Combination of Microbes and Ascend®

A. Seed Treatment with Isolated Microbe Combined with Ascend®

In this example, an isolated microbe from Tables 1-3 will be combined with Ascend® and applied as a seed coating to seeds of a plant. Upon applying the isolated microbe/Ascend® combination as a seed coating, the plant will be planted and cultivated in the standard manner.

A control plot of plant seeds, which did not have the isolated microbe/Ascend® combination applied as a seed coating, will also be planted.

It is expected that the plants grown from the seeds treated with the seed coating will exhibit a quantifiable increase in a phenotypic trait of interest, as compared to the control plants. It is expected that a synergistic effect may be observed for the phenotypic trait of interest.

B. Seed Treatment with Microbial Consortia Combined with Ascend®

In this example, a microbial consortium, comprising at least two microbes from Tables 1-3 will be combined with Ascend® and then applied as a seed coating to seeds of a plant. Upon applying the microbial consortium/Ascend® combination as a seed coating, the plant will be planted and cultivated in the standard manner.

A control plot of plant seeds, which did not have the microbial consortium/Ascend.® combination applied as a seed coating, will also be planted.

It is expected that the plants grown from the seeds treated with the seed coating will exhibit a quantifiable increase in a phenotypic trait of interest, as compared to the control plants. It is expected that a synergistic effect may be observed for the phenotypic trait of interest.

VI. Microbial Consortia

The microbial consortia utilized in the examples are presented in Table 13 in a non-limiting matter, while recognizing that the microbial consortia may comprise any one or more microbes presented in tables 1-3.

TABLE 13

| Consortia Compositions | | | |
|---|---|---|---|
| ID | Microbes | ID | Microbes |
| D1 | Stenotrophomonas maltophilia BDNZ 54073<br>Rhodococcus erythropolis BDNZ 54093<br>Pantoea vagans BDNZ 55529<br>Pseudomonas oryzihabitans BDNZ 55530 | D2 | Rhodococcus erythropolis BDNZ 54093<br>Pseudomonas oryzihabitans BDNZ 55530<br>Rahnella aquatilis BDNZ 56532 |
| D3 | Stenotrophomonas maltophilia BDNZ 54073<br>Rhodococcus erythropolis BDNZ 54093<br>Pantoea vagans BDNZ 55529<br>Rahnella aquatilis BDNZ 56532 | D4 | Stenotrophomonas maltophilia BDNZ 54073<br>Rhodococcus erythropolis BDNZ 54093<br>Pseudomonas fluorescens BDNZ 56530<br>Pantoea agglomerans BDNZ 57547 |
| D5 | Rhodococcus erythropolis BDNZ 54093<br>Pseudomonas fluorescens BDNZ 56530<br>Pantoea agglomerans BDNZ 57547 | D6 | Rahnella aquatilis BDNZ 57157<br>Rahnella aquatilis BDNZ 58013<br>Rhizobium etli BDNZ 60473 |

TABLE 13-continued

Consortia Compositions

| ID | Microbes | ID | Microbes |
|---|---|---|---|
| D7 | *Stenotrophomonas maltophilia* BDNZ 54073<br>*Rhodococcus erythropolis* BDNZ 54093<br>*Pantoea vagans* BDNZ 55529<br>*Pseudomonas oryzihabitans* BDNZ 55530<br>*Rahnella aquatilis* BDNZ 56532 | D8 | *Stenotrophomonas maltophilia* BDNZ 54073<br>*Rhodococcus erythropolis* BDNZ 54093<br>*Pantoea vagans* BDNZ 55529<br>*Pseudomonas oryzihabitans* BDNZ 55530<br>*Rahnella aquatilis* BDNZ 57157<br>*Rahnella aquatilis* BDNZ 58013<br>*Rhizobium etli* BDNZ 60473 |
| D9 | *Rahnella aquatilis* BDNZ 56532 | D10 | *Rhodococcus erythropolis* BDNZ 54093<br>*Pantoea vagans* BDNZ 55529<br>*Pseudomonas oryzihabitans* BDNZ 55530<br>*Rahnella aquatilis* BDNZ 56532 |
| D11 | *Exiguobacterium aurantiacum* BCI 50<br>*Duganella radicis* BCI 105<br>*Rhizobium pusense* BCI 106<br>*Kosakonia radicincitans* BCI 107<br>*Delftia lacustris* BCI 124 | D12 | *Rahnella aquatilis* BCI 29<br>*Duganella radicis* BCI 31<br>*Exiguobacterium sibiricum* BCI 116<br>*Novosphingobium sediminicola* BCI 130<br>*Ensifer* sp. BCI 131<br>*Microbacterium oleivorans* BCI 132 |
| D13 | *Chitinophaga terrae* BCI 79<br>*Exiguobacterium* sp. BCI 81<br>*Novosphingobium sediminicola* BCI 82<br>Exiguobacterium acetylicum BCI 83<br>*Variovorax ginsengisoli* BCI 137 | D14 | *Exiguobacterium acetylicum* BCI 23<br>*Rahnella aquatilis* BCI 29<br>*Rhizobium lemnae* BCI 34<br>*Achromobacter spanius* BCI 385 |
| D15 | *Dyadobacter soli* BCI 68<br>*Chitinophaga terrae* BCI 79<br>*Pedobacter terrae* BCI 91<br>*Massilia albidiflava* BCI 97<br>*Novosphingobium sediminicola* BCI 136 | D16 | *Rhodococcus erythropolis* BDNZ 54093<br>*Pantoea vagans* BDNZ 55529<br>*Pseudomonas oryzihabitans* BDNZ 55530 |
| D17 | *Rhodococcus erythropolis* BDNZ 54093<br>*Rahnella aquatilis* BDNZ 56532<br>*Rahnella aquatilis* BDNZ 58013<br>*Rhizobium etli* BDNZ 60473 | D18 | *Exiguobacterium acetylicum* BCI125<br>*Bacillus megaterium* BCI 255<br>*Paenibacillus glycanilyticus* BCI 418 |
| D19 | *Agrobacterium fabrum* BCI 608<br>*Acidovorax soli* BCI 690<br>*Rhizobium grahamii* BCI 691<br>*Bacillus subtilis* BCI 989 | D20 | *Arthrobacter pascens* BCI 682<br>*Novosphingobium lindaniclasticum* BCI 684<br>*Bosea robiniae* BCI 688<br>*Microbacterium maritypicum* BCI 689<br>*Sphingopyxis alaskensis* BCI 914 |
| D21 | *Chryseobacterium rhizosphaerae* BCI 615<br>*Hydrogenophaga atypica* BCI 687 | D22 | *Novosphingobium resinovorum* BCI 557<br>*Arthrobacter mysorens* BCI 700 |

TABLE 13-continued

| Consortia Compositions | | | |
|---|---|---|---|
| ID | Microbes | ID | Microbes |
| | *Bosea robiniae* BCI 689 *Microbacterium maritypicum* BCI 688 *Agrobacterium fabrum* BCI 958 | | *Bosea thiooxidans* BCI 703 *Bacillus oleronius* BCI 1071 |
| D23 | *Pedobacter rhizosphaerae* BCI 598 *Bacillus* sp. BCI 715 *Pseudomonas jinjuensis* BCI 804 *Pseudomonas putida* BCI 805 | D24 | *Novosphingobium sediminicola* BCI 130 *Ensifer* sp. BCI 131 *Microbacterium oleivorans* BCI 132 |
| D25 | *Arthrobacter cupressi* BCI 59 *Dyadobacter soli* BCI 68 | D26 | *Bosea robiniae* BCI 689 *Bosea thiooxidans* BCI 703 *Bosea eneae* BCI 1267 |
| A1 | *Stenotrophomonas maltophilia* BDNZ 54073 *Rhodococcus erythropolis* BDNZ 54093 *Pantoea vagans* BDNZ 55529 *Pseudomonas oryzihabitans* BDNZ55530 | A2 | *Flavobacterium glaciei* BDNZ 66487 *Massilia niastensis* BDNZ 55184 *Pseudomonas fluorescens* BDNZ 54480 |
| A3 | *Azospirillum lipoferum* BDNZ 57661 *Herbaspirillum huttiense* BDNZ 54487 *Pantoea agglomerans* BDNZ 54499 *Pseudomonas fluorescens* BDNZ 54480 | A4 | *Janthinobacterium* sp. BDNZ 54456 *Mucilaginibacter dorajii* BDNZ 66513 *Pseudomonas psychrotolerans* BDNZ 54517 |
| A5 | *Janthinobacterium* sp. BDNZ 54456 *Mucilaginibacter dorajii* BDNZ 66513 *Pseudomonas psychrotolerans* BDNZ 54517 | A6 | *Rhizobium etli* BDNZ 61443 *Caulobacter henrici* BDNZ 66341 *Duganella violaceinigra* BDNZ 66361 |
| A7 | *Duganella violaceinigra* BDNZ 66361 | A8 | *Ramlibacter henchirensis* BDNZ 66331 *Rhizobium pisi* BDNZ 66326 *Mucilaginibacter gosypii* BDNZ 66321 *Paenibacillus amylolyticus* BDNZ 66316 |
| A9 | *Polaromonas ginsengisoli* BDNZ 66373 | A10 | *Sphingobium quisquiliarum* BDNZ 66576 *Bacillus subtilis* BDNZ 66347 *Azospirillum lipoferum* BDNZ 66297 |
| A11 | *Rhodoferax ferrireducens* BDNZ 66374 *Mucilaginibacter gosypii* BDNZ 66321 *Paenibacillus amylolyticus* BDNZ 66316 *Azospirillum lipoferum* BDNZ66315 | A12 | *Rhodococcus erythropolis* BDNZ 54093 *Pseudomonas oryzihabitans* BDNZ 55530 *Rahnella aquatilis* BDNZ 56532 |
| A13 | *Rhodococcus erythropolis* BDNZ 54093 *Rahnella aquatilis* BDNZ 57157 *Azotobacter chroococcum* BDNZ57597 | A14 | *Rhodococcus erythropolis* BDNZ54299 *Rahnella aquatilis* BDNZ58013 *Herbaspirillum huttiense* BDNZ 65600 |
| A15 | *Rhodococcus erythropolis* BDNZ 54093 *Pseudomonas oryzihabitans* | | |

TABLE 13-continued

| Consortia Compositions | | | |
|---|---|---|---|
| ID | Microbes | ID | Microbes |
| | BDNZ 55530 *Rahnella aquatilis* BDNZ 56532 | | |

VII. Effects of Microbial Consortia on Plant Phenotypes

Example 1: Evaluate Phenotype of Plants Exposed to Microbial Consortia in U.S. Trials Plants disclosed in Table 14 were grown in a controlled environment in a rooting volume of 167 ml and typically in a soil substrate. The chamber photoperiod was set to 16 hours for all experiments on all species. The light intensity ranged from 180 µmol PAR $m^{-2}$ $s^{-1}$ to approximately µmol PAR $m^{-2}$ $s^{-1}$ as plant height increased during experiments.

The air temperature was typically 28° C. during the photoperiod, decreasing to 23° C. during the night for *Zea mays*, *Glycine max*, and *Sorghum bicolor* experiments. Air temperature was typically 24° C. during the photoperiod, decreasing to 20° C. during the night for *Triticum aestivum* experiments.

Phenotypes were measured during early vegetative growth, typically before the V3 developmental stage.

Leaf chlorophyll content was measured midway along the youngest fully-expanded leaf, non-destructively using a meter providing an index of leaf chlorophyll content (CCM-200, Opti Sciences, Hudson, N.H., US).

Whole plant, shoot, and root dry weight was measured after plants had been dried to a constant weight in a drying oven set to 80° C. At least 10 replicate plants were measured for each phenotype measured in each experiment.

A control treatment of uninoculated seeds was run in each experiment for comparison with plants grown from seeds inoculated with microbial consortia.

TABLE 14

| | | | | Controlled Environment Efficacy (%) | | | | |
|---|---|---|---|---|---|---|---|---|
| Consortia | Crop | Assay | Evaluations | Plant | Shoot | Root | Chorophyll | T leaf |
| D1 | Zea mays | early vigor | 21 | | | 74 | | 25 |
| D6 | Zea mays | early vigor | 15 | | | 36 | 36 | 22 |
| D7 | Zea mays | early vigor | 15 | 72 | 63 | 65 | 25 | 0 |
| D11 | Zea mays | early vigor | 17 | | | 60 | | 20 |
| D13 | Zea mays | early vigor | 12 | | 40 | | 33 | 0 |
| D14 | Zea mays | early vigor | 15 | 62 | 69 | | 22 | 10 |
| D15 | Zea mays | early vigor | 12 | | | 70 | 25 | 0 |
| D25 | Zea mays | early vigor | 13 | | | 63 | 22 | 0 |
| D2 | Zea mays | early vigor | 5/4* | 100 | 100 | 100* | 60 | — |
| D3 | Zea mays | early vigor | 5/4* | 80 | 100 | 75* | 60 | — |
| D4 | Zea mays | early vigor | 5/4* | 80 | 80 | 75* | 60 | — |
| D5 | Zea mays | early vigor | 5/4* | 60 | 80 | 100* | 80 | — |
| D8 | Zea mays | early vigor | 5/4* | 60 | 80 | 75* | 40 | — |
| D12 | Zea mays | early vigor | 3 | 100 | 100 | 100 | 66 | — |
| D24 | Zea mays | early vigor | 2 | 100 | 100 | 100 | 0 | 0 |
| D1 | Sorghum bicolor | early vigor | 5 | 60 | 80 | 80 | 40 | 20 |
| D11 | Sorghum bicolor | early vigor | 3 | 60 | 80 | 80 | 40 | 20 |
| D13 | Sorghum bicolor | early vigor | 5 | 80 | 60 | 80 | 60 | 40 |
| D14 | Sorghum bicolor | early vigor | 5 | 80 | 80 | 100 | 40 | 20 |
| D15 | Sorghum bicolor | early vigor | 3 | 100 | 66 | 100 | 33 | 0 |
| D6 | Sorghum bicolor | early vigor | 3 | 100 | 100 | 100 | 33 | 66 |
| D7 | Sorghum bicolor | early vigor | 3 | 33 | 33 | 33 | 33 | 66 |
| D25 | Sorghum bicolor | early vigor | 3 | 66 | 100 | 66 | 33 | 66 |
| D9 | Triticum aestivum | early vigor | 8/6* | | 38 | 63 | 33* | — |
| D10 | Triticum aestivum | early vigor | 8/6* | 63 | 38 | 63 | | — |
| D16 | Triticum aestivum | early vigor | 8/6* | | | 63 | 33* | — |
| D17 | Triticum aestivum | early vigor | 8/6* | 76 | 63 | 75 | 33* | — |
| D18 | Triticum aestivum | early vigor | 8/6* | | 50 | 50 | 33* | — |
| D26 | Triticum aestivum | early vigor | 8/6* | | 66 | 66 | 0* | — |

TABLE 14-continued

| | | | | Controlled Environment Efficacy (%) | | | | |
|---|---|---|---|---|---|---|---|---|
| Consortia | Crop | Assay | Evaluations | Plant | Shoot | Root | Chorophyll | T leaf |
| D19 | Glycine max | early vigor | 2 | 0 | 0 | 0 | — | — |
| D20 | Glycine max | early vigor | 2 | 100 | 100 | 100 | 0 | — |
| D21 | Glycine max | early vigor | 2 | 0 | 0 | 0 | 0 | — |
| D22 | Glycine max | early vigor | 2 | | | 0 | | — |
| D23 | Glycine max | early vigor | 2 | | 100 | | | — |
| A1 | Zea mays | early vigor | 5 | — | 80 | 80 | — | — |
| A2 | Triticum aestivum | cold tolerance | 4 | — | 75 | 75 | — | — |
| A3 | Triticum aestivum | cold tolerance | 4 | — | 75 | 75 | — | — |
| A4 | Triticum aestivum | cold tolerance | 2 | — | 100 | 100 | — | — |
| A5 | Triticum aestivum | early vigor | 2 | — | 50 | 50 | — | — |
| A6 | Solanum sp. | early vigor | 2 | — | 100 | 100 | — | — |
| A7 | Solanum sp. | early vigor | 3 | — | 100 | 100 | — | — |
| A8 | Solanum sp. | early vigor | 3 | — | 100 | 66 | — | — |
| A9 | Solanum sp. | early vigor | 3 | — | 66 | 100 | — | — |
| A10 | Solanum sp. | early vigor | 3 | — | 66 | 66 | — | — |
| A11 | Solanum sp. | early vigor | 3 | — | 100 | 66 | — | — |
| A12 | Solanum sp. | early vigor | 2 | — | 100 | 50 | — | — |
| A13 | Triticum aestivum | early vigor | 2 | — | 0 | 0 | — | — |
| A14 | Triticum aestivum | early vigor | 2 | — | | | — | — |

The data presented in table 14 describes the percentage of time (efficiency) particular consortium changed a phenotype of interest relative to a control run in the same experiment. The measured phenotypes were whole plant dry weight (plant), shoot dry weight (shoot), root dry weight (root), leaf chlorophyll content (chlorophyll), and leaf temperature (Tleaf).

The data presented is averaged across the number of times a specific consortium was tested against a control (evaluations). For consortia where different phenotypes were measured in a different number of evaluations, an asterisk was placed next to data points to match the phenotype with the number of evaluations. Evaluations have been broken down and displayed for specific crop species (crop).

The presented data identifies consortia that have increased a phenotype of interest in greater than 60% of evaluations (hit rate>59) and consortia that decreased a phenotype of interest in greater than 60% of evaluations (hit rate<41). Both increases and decreases in a phenotype of interest were recorded to reflect the possibility that decreases in select phenotypes of interest are yield relevant. Improvement in canopy photosynthesis through decreased leaf chlorophyll, and improvement in drought tolerance through decreased shoot biomass constitute two examples.

Example 2: Evaluate Phenotype of Plants Exposed to Microbial Consortia in New Zealand Trials The inoculants were prepared from isolates grown as spread plates on R2A incubated at 25° C. for 48 to 72 hours. Colonies were harvested by blending with sterile distilled water (SDW) which was then transferred into sterile containers. Serial dilutions of the harvested cells were plated and incubated at 25° C. for 24 hours to estimate the number of colony forming units (CFU) in each suspension. Dilutions were prepared using individual isolates or blends of isolates (consortia) to deliver ~1×10$^5$ cfu/microbe/seed and seeds inoculated by either imbibition in the liquid suspension or by overtreatment with 5% vegetable gum and oil.

Seeds corresponding to the plants of table 15 were planted within 24 to 48 hours of treatment in agricultural soil, potting media or inert growing media. Plants were grown in small pots (28 mL to 200 mL) in either a controlled environment or in a greenhouse. Chamber photoperiod was set to 16 hours for all experiments on all species. Air temperature was typically maintained between 22-24° C.

Unless otherwise stated, all plants were watered with tap water 2 to 3 times weekly. Growth conditions were varied according to the trait of interest and included manipulation of applied fertilizer, watering regime and salt stress as follows:

Low N—seeds planted in soil potting media or inert growing media with no applied N fertilizer Moderate N—seeds planted in soil or growing media supplemented with commercial N fertilizer to equivalent of 135 kg/ha applied N Insol P—seeds planted in potting media or inert growth substrate and watered with quarter strength Pikovskaya's liquid medium containing tri-calcium phosphate as the only form phosphate fertilizer.

Cold Stress—seeds planted in soil, potting media or inert growing media and incubated at 10° C. for one week before being transferred to the plant growth room.

Salt stress—seeds planted in soil, potting media or inert growing media and watered with a solution containing between 100 to 200 mg/L NaCl.

Untreated (no applied microbe) controls were prepared for each experiment. Plants were randomized on trays throughout the growth environment. Between 10 and 30 replicate plants were prepared for each treatment in each experiment. Phenotypes were measured during early vegetative growth, typically before the V3 developmental stage and between 3 and 6 weeks after sowing. Foliage was cut and weighed. Roots were washed, blotted dry and weighed. Results indicate performance of treatments against the untreated control.

TABLE 15

| Microbe sp. | Strain ID | Crop | Assay | Shoot IOC (%) | Root IOC (%) |
|---|---|---|---|---|---|
| *Bosea thiooxidans* overall | 1 | 2 | 3 | Efficacy 100% | Efficacy 100% |
| *Bosea thiooxidans* | 54522 | Wheat | Early vigor - insol P | 30-40 | — |
| *Bosea thiooxidans* | 54522 | Ryegrass | Early vigor | 50-60 | 50-60 |
| *Bosea thiooxidans* | 54522 | Ryegrass | Early vigor - moderate P | 0-10 | 0-10 |
| *Duganella violaceinigra* overall | 1 | 1 | 1 | Efficacy 100% | Efficacy 100% |
| *Duganella violaceinigra* | 66361 | Tomato | Early vigor | 0-10 | 0-10 |
| *Duganella violaceinigra* | 66361 | Tomato | Early vigor | 30-40 | 40-50 |
| *Duganella violaceinigra* | 66361 | Tomato | Early vigor | 20-30 | 20-30 |
| *Herbaspirillum huttiense* overall | 2 | 2 | 2 | Efficacy 100% | — |
| *Herbaspirillum huttiense* | 54487 | Wheat | Early vigor - insol P | 30-40 | — |
| *Herbaspirillum huttiense* | 60507 | Maize | Early vigor - salt stress | 0-10 | 0-10 |
| *Janthinobacterium* sp. Overall | 2 | 2 | 2 | Efficacy 100% | — |
| *Janthinobacterium* sp. | 54456 | Wheat | Early vigor - insol P | 30-40 | — |
| *Janthinobacterium* sp. | 54456 | Wheat | Early vigor - insol P | 0-10 | — |
| *Janthinobacterium* sp. | 63491 | Ryegrass | Early vigor - drought stress | 0-10 | 0-10 |
| *Massilia niastensis* overall | 1 | 1 | 2 | Efficacy 80% | Efficacy 80% |
| *Massilia niastensis* | 55184 | Wheat | Early vigor - salt stress | 0-10 | 20-30 |
| *Massilia niastensis* | 55184 | Winter wheat | Early vigor - cold stress | 0-10 | 10-20 |
| *Massilia niastensis* | 55184 | Winter wheat | Early vigor - cold stress | 20-30 | 20-30 |
| *Massilia niastensis* | 55184 | Winter wheat | Early vigor - cold stress | 10-20 | 10-20 |
| *Massilia niastensis* | 55184 | Winter wheat | Early vigor - cold stress | <0 | <0 |
| *Novosphingobium rosa* overall | 2 | 1 | 1 | Efficacy 100% | Efficacy 100% |
| *Novosphingobium rosa* | 65589 | Maize | Early vigor - cold stress | 0-10 | 0-10 |
| *Novosphingobium rosa* | 65619 | Maize | Early vigor - cold stress | 0-10 | 0-10 |
| *Paenibacillus amylolyticus* overall | 1 | 1 | 1 | Efficacy 100% | Efficacy 100% |
| *Paenibacillus amylolyticus* | 66316 | Tomato | Early vigor | 0-10 | 0-10 |
| *Paenibacillus amylolyticus* | 66316 | Tomato | Early vigor | 10-20 | 10-20 |
| *Paenibacillus amylolyticus* | 66316 | Tomato | Early vigor | 0-10 | 0-10 |
| *Pantoea agglomerans* | 3 | 2 | 3 | Efficacy 33% | Efficacy 50% |
| *Pantoea agglomerans* | 54499 | Wheat | Early vigor - insol P | 40-50 | — |
| *Pantoea agglomerans* | 57547 | Maize | Early vigor - low N | <0 | 0-10 |
| *Pantoea vagans* (formerly *P. agglomerans*) | 55529 | Maize | Early vigor | <0 | <0 |
| *Polaromonas ginsengisoli* | 1 | 1 | 1 | Efficacy 66% | Efficacy 100% |
| *Polaromonas ginsengisoli* | 66373 | Tomato | Early vigor | 0-10 | 0-10 |
| *Polaromonas ginsengisoli* | 66373 | Tomato | Early vigor | 20-30 | 30-40 |
| *Polaromonas ginsengisoli* | 66373 | Tomato | Early vigor | <0 | 10-20 |
| *Pseudomonas fluorescens* | 1 | 2 | 2 | Efficacy 100% | — |
| *Pseudomonas fluorescens* | 54480 | Wheat | Early vigor - insol P | >100 | — |
| *Pseudomonas fluorescens* | 56530 | Maize | Early vigor - moderate N | 0-10 | — |
| *Rahnella aquatilis* | 3 | 3 | 4 | Efficacy 80% | Efficacy 63% |
| *Rahnella aquatilis* | 56532 | Maize | Early vigor - moderate N | 10-20 | — |
| *Rahnella aquatilis* | 56532 | Maize | Early vigor - moderate N | 0-10 | 0-10 |
| *Rahnella aquatilis* | 56532 | Wheat | Early vigor - cold stress | 0-10 | 10-20 |

TABLE 15-continued

| Microbe sp. | Strain ID | Crop | Assay | Shoot IOC (%) | Root IOC (%) |
|---|---|---|---|---|---|
| Rahnella aquatilis | 56532 | Wheat | Early vigor - cold stress | <0 | 0-10 |
| Rahnella aquatilis | 56532 | Wheat | Early vigor - cold stress | 10-20 | <0 |
| Rahnella aquatilis | 57157 | Ryegrass | Early vigor | <0 | — |
| Rahnella aquatilis | 57157 | Maize | Early vigor - low N | 0-10 | 0-10 |
| Rahnella aquatilis | 57157 | Maize | Early vigor - low N | 0-10 | <0 |
| Rahnella aquatilis | 58013 | Maize | Early vigor | 0-10 | 10-20 |
| Rahnella aquatilis | 58013 | Maize | Early vigor - low N | 0-10 | <0 |
| Rhodococcus erythropolis | 3 | 1 | 3 | Efficacy 66% | — |
| Rhodococcus erythropolis | 54093 | Maize | Early vigor - low N | 40-50 | — |
| Rhodococcus erythropolis | 54299 | Maize | Early vigor - insol P | >100 | — |
| Rhodococcus erythropolis | 54299 | Maize | Early vigor | <0 | <0 |
| Stenotrophomonas chelatiphaga | 6 | 1 | 1 | Efficacy 60% | Efficacy 60% |
| Stenotrophomonas chelatiphaga | 54952 | Maize | Early vigor | 0-10 | 0-10 |
| Stenotrophomonas chelatiphaga | 47207 | Maize | Early vigor | <0 | 0 |
| Stenotrophomonas chelatiphaga | 64212 | Maize | Early vigor | 0-10 | 10-20 |
| Stenotrophomonas chelatiphaga | 64208 | Maize | Early vigor | 0-10 | 0-10 |
| Stenotrophomonas chelatiphaga | 58264 | Maize | Early vigor | <0 | <0 |
| Stenotrophomonas maltophilia | 6 | 1 | 2 | Efficacy 43% | Efficacy 66% |
| Stenotrophomonas maltophilia | 54073 | Maize | Early vigor - low N | 50-60 | — |
| Stenotrophomonas maltophilia | 54073 | Maize | Early vigor | <0 | 0-10 |
| Stenotrophomonas maltophilia | 56181 | Maize | Early vigor | 0-10 | <0 |
| Stenotrophomonas maltophilia | 54999 | Maize | Early vigor | 0-10 | 0-10 |
| Stenotrophomonas maltophilia | 54850 | Maize | Early vigor | 0 | 0-10 |
| Stenotrophomonas maltophilia | 54841 | Maize | Early vigor | <0 | 0-10 |
| Stenotrophomonas maltophilia | 46856 | Maize | Early vigor | <0 | <0 |
| Stenotrophomonas rhizophila | 8 | 1 | 1 | Efficacy 12.5% | Efficacy 37.5% |
| Stenotrophomonas rhizophila | 50839 | Maize | Early vigor | <0 | <0 |
| Stenotrophomonas rhizophila | 48183 | Maize | Early vigor | <0 | <0 |
| Stenotrophomonas rhizophila | 45125 | Maize | Early vigor | <0 | <0 |
| Stenotrophomonas rhizophila | 46120 | Maize | Early vigor | <0 | 0-10 |
| Stenotrophomonas rhizophila | 46012 | Maize | Early vigor | <0 | <0 |
| Stenotrophomonas rhizophila | 51718 | Maize | Early vigor | 0-10 | 0-10 |
| Stenotrophomonas rhizophila | 66478 | Maize | Early vigor | <0 | <0 |
| Stenotrophomonas rhizophila | 65303 | Maize | Early vigor | <0 | 0-10 |
| Stenotrophomonas terrae | 2 | 2 | 1 | Efficacy 50% | Efficacy 50% |
| Stenotrophomonas terrae | 68741 | Maize | Early vigor | <0 | <0 |
| Stenotrophomonas terrae | 68599 | Maize | Early vigor | <0 | 0-10 |
| Stenotrophomonas terrae | 68599 | Capsicum * | Early vigor | 20-30 | 20-30 |
| Stenotrophomonas terrae | 68741 | Capsicum * | Early vigor | 10-20 | 20-30 |

The data presented in table 15 describes the efficacy with which a microbial species or strain can change a phenotype of interest relative to a control run in the same experiment. Phenotypes measured were shoot fresh weight and root fresh weight for plants growing either in the absence of presence of a stress (assay). For each microbe species, an overall efficacy score indicates the percentage of times a strain of that species increased a both shoot and root fresh weight in independent evaluations. For each species, the specifics of each independent assay is given, providing a strain ID (strain) and the crop species the assay was performed on (crop). For each independent assay the percentage increase in shoot and root fresh weight over the controls is given.

Example 3: Evaluate Yield Effect of Maize Exposed to Microbial Consortia in U.S. Field Trials The data presented in Table 16 summarizes the changes in final yield relative to a control for six consortia tested in eight locations in the mid-West of the United States. Also presented is final yield data from two drought trials performed in California in the United States. Data is expressed as the percentage of trials in which a yield effect in bushels per acre of a particular magnitude was observed. All field trials were run in accordance with standard agronomic practices.

TABLE 16

| | | Field Trial Yield Increases (%) | | |
|---|---|---|---|---|
| Consortia | Trials | >6 bu ac | 0-6 bu ac | <0 bu ac |
| D1 | 8 Yield | 62.5 | 25 | 12.2 |
| D6 | 8 Yield | 25 | 25 | 50 |
| D7 | 8 Yield | 25 | 37.5 | 37.5 |
| D2 | 8 Yield | 25 | 37.5 | 37.5 |
| D3 | 8 Yield | 25 | 25 | 50 |
| D4 | 8 Yield | 25 | 37.5 | 37.5 |

TABLE 16-continued

| Consortia | Trials | Field Trial Yield Increases (%) | | |
| --- | --- | --- | --- | --- |
| | | >6 bu ac | 0-6 bu ac | <0 bu ac |
| D5 | 8 Yield | 25 | 50 | 25 |
| D12 | 2 Drought | 100 | — | — |

Example 4: Evaluate Yield Effect of Maize Exposed to Microbial Consortia in New Zealand Field Trials The data presented in Table 17 summarizes the results of New Zealand field trials for select consortia. The presented data describes the number of trials in which a particular consortia has been tested relative to a control, and the number of trials in which the consortia treatment increased the final yield relative to the control treatment. All field trials were run in accordance with standard agronomic practices.

TABLE 17

| Consortia | Trials | Trials with yield > control |
| --- | --- | --- |
| A1 | 3 | 3 |
| D6 | 2 | 1 |
| A13 | 2 | 1 |
| A14 | 1 | 1 |
| A15 | 3 | 3 |

Example 5: Microbes Deposited with the ARS Culture Collection (NRRL)

In one experimental embodiment, the inventors utilized the following microbial species in applications of the present disclosure. Table 18 details microbial species of the present disclosure which have been deposited with the United States Department of Agriculture ARS Culture Collection (NRRL).

TABLE 18

| | Taxonomy | BCI (US) | BDNZ (NZ) | Deposited date | Accession number | USDA Viability Date |
| --- | --- | --- | --- | --- | --- | --- |
| 1 | *Acidovorax soli* | 648 | | Dec. 29, 2015 | NRRL B-67181 | Jan. 4, 2016 |
| 2 | *Acidovorax soli* | 690 | | Dec. 29, 2015 | NRRL B-67182 | Jan. 4, 2016 |
| 3 | *Arthrobacter cupressi* | 59 | | Dec. 29, 2015 | NRRL B-67183 | Jan. 4, 2016 |
| 4 | *Arthrobacter cupressi* | 62 | | Dec. 29, 2015 | NRRL B-67184 | Jan. 4, 2016 |
| 5 | *Bosea eneae* | 1267 | | Dec. 29, 2015 | NRRL B-67185 | Jan. 4, 2016 |
| 6 | *Bosea robiniae* | 689 | | Dec. 29, 2015 | NRRL B-67186 | Jan. 4, 2016 |
| 7 | *Bosea thiooxidans* | 703 | | Dec. 29, 2015 | NRRL B-67187 | Jan. 4, 2016 |
| 8 | *Chitinophaga terrae* | 79 | | Dec. 29, 2015 | NRRL B-67188 | Jan. 4, 2016 |
| 9 | *Chitinophaga terrae* | 109 | | Dec. 29, 2015 | NRRL B-67189 | Jan. 4, 2016 |
| 10 | *Delftia lacustris* | 124 | | Dec. 29, 2015 | NRRL B-67190 | Jan. 4, 2016 |
| 11 | *Delftia lacustris* | 2350 | | Dec. 29, 2015 | NRRL B-67191 | Jan. 4, 2016 |
| 12 | *Duganella radicis* | 105 | | Dec. 29, 2015 | NRRL B-67192 | Jan. 4, 2016 |
| 13 | *Duganella violaceinigra* | 2204 | | Dec. 29, 2015 | NRRL B-67193 | Jan. 4, 2016 |
| 14 | *Dyadobacter soli* | 68 | | Dec. 29, 2015 | NRRL B-67194 | Jan. 4, 2016 |
| 15 | *Dyadobacter soli* | 96 | | Dec. 29, 2015 | NRRL B-67195 | Jan. 4, 2016 |
| 16 | *Flavobacterium glacei* | 4005 | | Dec. 29, 2015 | NRRL B-67196 | Jan. 4, 2016 |
| 17 | *Herbaspirillum chlorophenolicum* | 162 | | Dec. 29, 2015 | NRRL B-67197 | Jan. 4, 2016 |
| 18 | *Massilia kyonggiensis* (deposited as *Massilia albidiflava*) | 97 | | Dec. 29, 2015 | NRRL B-67198 | Jan. 4, 2016 |
| 19 | *Massilia niastensis* | 1217 | | Dec. 29, 2015 | NRRL B-67199 | Jan. 4, 2016 |
| 20 | *Novosphingobium lindaniclasticum* | 684 | | Dec. 29, 2015 | NRRL B-67201 | Jan. 4, 2016 |
| 21 | *Novosphingobium lindaniclasticum* | 608 | | Dec. 29, 2015 | NRRL B-67200 | Jan. 4, 2016 |
| 22 | *Novosphingobium resinovorum* | 557 | | Dec. 29, 2015 | NRRL B-67202 | Jan. 4, 2016 |
| 23 | *Novosphingobium resinovorum* | 3709 | | Dec. 29, 2015 | NRRL B-67203 | Jan. 4, 2016 |
| 24 | *Paenibacillus glycanilyticus* | 418 | | Dec. 29, 2015 | NRRL B-67204 | Jan. 4, 2016 |
| 25 | *Pedobacter rhizosphaerae* (deposited as *Pedobacter soli*) | 598 | | Dec. 29, 2015 | NRRL B-67205 | Jan. 4, 2016 |
| 26 | *Pedobacter terrae* | 91 | | Dec. 29, 2015 | NRRL B-67206 | Jan. 4, 2016 |
| 27 | *Pseudomonas jinjuensis* | 804 | | Dec. 29, 2015 | NRRL B-67207 | Jan. 4, 2016 |
| 28 | *Ramlibacter henchirensis* | 739 | | Dec. 29, 2015 | NRRL B-67208 | Jan. 4, 2016 |
| 29 | *Ramlibacter henchirensis* | 1959 | | Dec. 29, 2015 | NRRL B-67209 | Jan. 4, 2016 |

TABLE 18-continued

| | Taxonomy | BCI (US) | BDNZ (NZ) | Deposited date | Accession number | USDA Viability Date |
|---|---|---|---|---|---|---|
| 30 | Rhizobium rhizoryzae (previously R. lemnae) | 34 | | Dec. 29, 2015 | NRRL B-67210 | Jan. 4, 2016 |
| 31 | Rhizobium rhizoryzae (previously R. lemnae) | 661 | | Dec. 29, 2015 | NRRL B-67211 | Jan. 4, 2016 |
| 32 | Rhizobium sp. | 106 | | Dec. 29, 2015 | NRRL B-67212 | Jan. 4, 2016 |
| 33 | Sinorhizobium Chiapanecum (now Ensifer adhaerens) | 111 | | Dec. 29, 2015 | NRRL B-67213 | Jan. 4, 2016 |
| 34 | Sphingopyxis alaskensis | 412 | | Dec. 29, 2015 | NRRL B-67214 | Jan. 4, 2016 |
| 35 | Sphingopyxis alaskensis | 914 | | Dec. 29, 2015 | NRRL B-67215 | Jan. 4, 2016 |
| 36 | Variovorax ginsengisoli | 137 | | Dec. 29, 2015 | NRRL B-67216 | Jan. 4, 2016 |
| 37 | Variovorax ginsengisoli | 3078 | | Dec. 29, 2015 | NRRL B-67217 | Jan. 4, 2016 |
| 38 | Achromobacter pulmonis | 49 | | Dec. 18, 2015 | NRRL B-67174 | Dec. 21, 2015 |
| 39 | Chryseobacterium daecheongense | 45 | | Dec. 18, 2015 | NRRL B-67172 | Dec. 21, 2015 |
| 40 | Duganella radicis | 31 | | Jan. 13, 2016 | NRRL B-67166 | Jan. 15, 2016 |
| 41 | Exiguobacterium aurantiacum | 50 | | Dec. 18, 2015 | NRRL B-67175 | Dec. 21, 2015 |
| 42 | Exiguobacterium sibiricum | 116 | | Dec. 18, 2015 | NRRL B-67167 | Dec. 21, 2015 |
| 43 | Kosakonia radicincitans | 44 | | Dec. 18, 2015 | NRRL B-67171 | Dec. 21, 2015 |
| 44 | Microbacterium oleivorans | 132 | | Dec. 18, 2015 | NRRL B-67170 | Dec. 21, 2015 |
| 45 | Novosphingobium sediminicola | 130 | | Dec. 18, 2015 | NRRL B-67168 | Dec. 21, 2015 |
| 46 | Pedobacter terrae | 53 | | Dec. 18, 2015 | NRRL B-67176 | Dec. 21, 2015 |
| 47 | Rahnella aquatilis | 29 | | Dec. 18, 2015 | NRRL B-67165 | Dec. 21, 2015 |
| 48 | Rhizobium sp. (deposited as Agrobacterium fabrum) | 46 | | Dec. 18, 2015 | NRRL B-67173 | Dec. 21, 2015 |
| 49 | Sinorhizobium chiapanecum (Ensifer adhaerens - current classification) | 131 | | Dec. 18, 2015 | NRRL B-67169 | Dec. 21, 2015 |
| 50 | Pantoea vagans | | 55529 | Jan. 29, 2016 | NRRL B-67224 | |
| 51 | Pseudomonas oryzihabitans | | 55530 | Jan. 29, 2016 | NRRL B-67225 | |
| 52 | Stenotrophomonas maltophilia | | 54073 | Jan. 29, 2016 | NRRL B-67226 | |
| 53 | Rahnella aquatilis | | 58013 | Jan. 29, 2016 | NRRL B-67229 | |
| 54 | Rahnella aquatilis | | 56532 | Jan. 29, 2016 | NRRL B-67228 | |
| 55 | Rhodococcus erythropolis | | 54093 | Jan. 29, 2016 | NRRL B-67227 | |
| 56 | Herbaspirillum chlorophenolicum | 58 | | Feb. 8, 2016 | NRRL B-67236 | |
| 57 | Bacillus niacini | 4718 | | Feb. 8, 2016 | NRRL B-67230 | |
| 58 | Polaromonas ginsengisoli | | 66373 | Feb. 8, 2016 | NRRL B-67231 | |
| 59 | Polaromonas ginsengisoli | | 66821 | Feb. 8, 2016 | NRRL B-67234 | |
| 60 | Duganella violaceinigra | | 66361 | Feb. 8, 2016 | NRRL B-67232 | |
| 61 | Duganella violaceinigra | | 58291 | Feb. 8, 2016 | NRRL B-67233 | |
| 62 | Massilia niastensis | | 55184 | Feb. 8, 2016 | NRRL B-67235 | |

Example 6: Novel Microbial Species Deposited with the ARS Culture Collection (NRRL)

In one experimental embodiment, the inventors utilized the following microbial species in applications of the present disclosure.

TABLE 19

| Taxonomy | BCI (US) | BDNZ (NZ) |
|---|---|---|
| Achromobacter pulmonis | 49 | |
| Acidovorax soli | 648 | |
| Acidovorax soli | 690 | |

TABLE 19-continued

| Taxonomy | BCI (US) | BDNZ (NZ) |
|---|---|---|
| *Arthrobacter cupressi* | 59 | |
| *Arthrobacter cupressi* | 62 | |
| *Bacillus niacini* | 4718 | |
| *Bosea eneae* | 1267 | |
| *Bosea robiniae* | 689 | |
| *Bosea thiooxidans* | 703 | |
| *Chitinophaga terrae* | 79 | |
| *Chitinophaga terrae* | 109 | |
| *Chryseobacterium daecheongense* | 45 | |
| *Delftia lacustris* | 124 | |
| *Delftia lacustris* | 2350 | |
| *Duganella radicis* | 105 | |
| *Duganella radicis* | 31 | |
| *Duganella violaceinigra* | 2204 | |
| *Duganella violaceinigra* | | 66361 |
| *Duganella violaceinigra* | | 58291 |
| *Dyadobacter soli* | 68 | |
| *Dyadobacter soli* | 96 | |
| *Exiguobacterium aurantiacum* | 50 | |
| *Exiguobacterium sibiricum* | 116 | |
| *Flavobacterium glacei* | 4005 | |
| *Herbaspirillum chlorophenolicum* | 162 | |
| *Herbaspirillum chlorophenolicum* | 58 | |
| *Kosakonia radicincitans* | 44 | |
| *Massilia kyonggiensis* (deposited as *Massilia albidiflava*; new taxonomy is *kyonggiensis*) | 97 | |
| *Massilia niastensis* | 1217 | |
| *Massilia niastensis* | | 55184 |
| *Microbacterium oleivorans* | 132 | |
| *Novosphingobium lindaniclasticum* | 684 | |
| *Novosphingobium lindaniclasticum* | 608 | |
| *Novosphingobium resinovorum* | 557 | |
| *Novosphingobium resinovorum* | 3709 | |
| *Novosphingobium sediminicola* | 130 | |
| *Paenibacillus glycanilyticus* | 418 | |
| *Pantoea vagans* | | 55529 |
| *Pedobacter rhizosphaerae* (deposited as *Pedobacter soli*) | 598 | |
| *Pedobacter terrae* | 91 | |
| *Pedobacter terrae* | 53 | |
| *Polaromonas ginsengisoli* | | 66373 |
| *Polaromonas ginsengisoli* | | 66821 |
| *Pseudomonas jinjuensis* | 804 | |
| *Pseudomonas oryzihabitans* | | 55530 |
| *Rahnella aquatilis* | 29 | |
| *Rahnella aquatilis* | | 58013 |
| *Rahnella aquatilis* | | 56532 |
| *Ramlibacter henchirensis* | 739 | |
| *Ramlibacter henchirensis* | 1959 | |
| *Rhizobium rhizoryzae* | 34 | |
| *Rhizobium rhizoryzae* | 661 | |
| *Rhizobium* sp. | 106 | |
| *Rhizobium* sp. (deposited as *Agrobacterium fabrum* - in taxonomic flux) | 46 | |
| *Rhodococcus erythropolis* | | 54093 |
| *Sinorhizobium chiapanecum* (now *Ensifer adhaerens*) | 131 | |
| *Sinorhizobium Chiapanecum* (now *Ensifer adhaerens*) | 111 | |
| *Sphingopyxis alaskensis* | 412 | |
| *Sphingopyxis alaskensis* | 914 | |
| *Stenotrophomonas maltophilia* | | 54073 |
| *Variovorax ginsengisoli* | 137 | |
| *Variovorax ginsengisoli* | 3078 | |

Example 7: Deposited Microbial Species Novel to Agriculture

In one experimental embodiment, the inventors utilized the following microbial species in applications of the present disclosure. Table 20 notes microbial organisms of the present disclosure which have been deposited with the NRRL, ATCC, and/or DSMZ depositories with the respective accession numbers.

TABLE 20

Species novel to Agriculture (in Tables 1, 2, 3, and 17)

| Species | NRRL # | DSMZ # | ATTC # |
|---|---|---|---|
| *Acidovorax soli* | NRRL B-67181 | | |
| | NRRL B-67182 | | |
| *Agrobacterium fabrum* or *Rhizobium pusense* (In Taxonomic Flux) | NRRL B-67173 | | |
| *Arthrobacter cupressi* | NRRL B-67183 | | |
| | NRRL B-67184 | | |
| *Bosea eneae* | NRRL B-67185 | | |
| *Bosea minatitlanensis* | | DSM-13099 | 700918 |
| *Bosea robinae* | NRRL B-67186 | | |
| *Caulobacter henricii* | | DSM-4730 | 15253 |
| *Chitinophaga arvensicola* | | DSM-3695 | 51264 |
| *Chitinophaga terrae* | NRRL B-67188 | | |
| *Delftia lacustris* | NRRL B-67190 | | |
| | NRRL B-67191 | | |
| *Duganella radicis* | NRRL B-67192 | | |
| | NRRL B-67166 | | |
| *Duganella violaceinigra* (*Pseudoduganella violaceinigra*) | NRRL B-67193 | | |
| | NRRL B-67232 | | |
| | NRRL B-67233 | | |
| *Dyadobacter soli* | NRRL B-67193 | | |
| | NRRL B-67194 | | |
| *Flavobacterium glaciei* | NRRL B-67196 | | |
| *Frateuria aurantia* | | DSM-6220 | |
| *Frateuria terrea* | | DSM-26515 | |
| *Herbaspirillum chlorophenolicum* | NRRL B-67197 | | |
| | NRRL B-67236 | | |
| *Janthinobacterium agaricidamnosum* | | DSM-9628 | |
| *Janthinobacterium lividum* | | DSM-1522 | |
| *Luteibacter yeojuensis* | | DSM-17673 | |
| *Massilia albidiflava* | NRRL B-67198 | | |
| *Massilia niastensis* | NRRL B-67199 | | |
| | NRRL B-67235 | | |
| *Microbacterium* sp. (*OLIEVORANS* DEPOSITED) | | DSM-16050 | 31001 |
| *Novosphingobium lindaniclasticum* | NRRL B-67201 | | |
| | NRRL B-67200 | | |
| *Novosphingobium resinovorum* | NRRL B-67202 | | |
| | NRRL B-67203 | | |
| *Novosphingobium rosa* | | DSM-7285 | 51837 |
| *Paenibacillus amylolyticus* | | DSM-11730 | 9995 |
| *Paenibacillus chondroitinus* | | DSM-5051 | 51184 |
| *Paenibacillus glycanilyticus* | NRRL B-67204 | | |
| *Pedobacter rhizosphaerae* (*Pedobacter soli*) | NRRL B-67205 | | |
| *Pedobacter terrae* | NRRL B-67206 | | |
| | NRRL B-67176 | | |
| *Polaromonas ginsengisoli* | NRRL B-67231 | | |
| | NRRL B-67234 | | |
| *Pseudomonas jinjuensis* | NRRL B-67207 | | |
| *Ramlibacter henchirensis* | NRRL B-67208 | | |
| *Rhizobium rhizoryzae* | NRRL B-67210 | | |
| | NRRL B-67211 | | |
| *Rhodoferax ferrireducens* | | DSM-15236 | BAA-621 |
| *Sinorhizobium chiapanecum* (*Ensifer adhaerens*) | NRRL B-67213 | | |
| | NRRL B-67169 | | |
| *Sphingobium quisquiliarum* | | DSM-24952 | |
| *Sphingopyxis alaskensis* | NRRL B-67214 | | |
| | NRRL B-67215 | | |
| *Stenotrophomonas terrae* | | DSM-18941 | |
| *Variovorax ginsengisoli* | NRRL B-67216 | | |
| | NRRL B-67217 | | |

Example 8: Microbial Consortia Embodiments

In one experimental embodiment, the inventors utilized the following microbial consortia in applications of the present disclosure. Table 21 notes microbial consortia D1, A1, D6, D7, D12, and A15 of the present disclosure. Underneath each of the consortia designations are the specific strain numbers that identify the microbes present in each of the consortia.

TABLE 21

| Strain BCI# | Strain BDNZ# | Microbe identity | Consortia* D1, A1 | D6 | D7 | D12 | A15 |
|---|---|---|---|---|---|---|---|
| | 54073 | Stenotrophomonas maltophilia (54073) | 54073 | | 54073 | | |
| | 54093 | Rhodococcus erythropolis (54093) | 54093 | | 54093 | | 54093 |
| | 55529 | Pantoea vagans (55529) | 55529 | | 55529 | | |
| | 55530 | Pseudomonas oryzihabitans (55530) | 55530 | | 55530 | | 55530 |
| | 57157 | Rahnella aquatilis (57157) | | 57157 | | | |
| | 58013 | Rahnella aquatilis (58013) | | 58013 | | | |
| | 60473 | Rhizobium etli (60473) | | 60473 | | | |
| | 56532 | Rahnella aquatilis (56532) | | | | 56532 | 56532 |
| 29 | 29 | Rahnella aquatilis (29) | | | | 29 | |
| 31 | 31 | Duganella radicis (31) | | | | 31 | |
| 116 | | Exiguobacterium sibiricum (116) | | | | 116 | |
| 130 | | Novosphingobium sediminicola (130) | | | | 130 | |
| 131 | | Ensifer adhaerens (131) | | | | 131 | |
| 132 | | Microbacterium oleivorans (132) | | | | 132 | |

Example 9: Microbial Strain and Microbial Species Embodiments

In one experimental embodiment, the inventors utilized the following microbial species and/or strains in applications of the present disclosure. Table 22 notes specific microbial species and strains utilized in experimental studies which are novel to agriculture and have exhibited positive results in controlled environment screening experiments of the present disclosure.

TABLE 22

| Individual species of note Species | Strain BDNZ# | Strain BCI# | Individual strains of note Species | Strain BDNZ# |
|---|---|---|---|---|
| Duganella violaceinigra | 66361 | | Stenotrophomonas maltophilia | 54073 |
| Bosea thiooxidans | 54522 | 703 | Rhodococcus erythropolis | 54093 |
| Massilia niastensis | 55184 | 1217 | Pantoea vagans | 55529 |
| Polaromonas ginsengisoli | 66373 | | Pseudomonas oryzihabitans | 55530 |
| Novosphingobium resinovorum | | 557 | | |
| Duganella violaceinigra | | 2204 | | |
| Exiguobacterium aurantiacum | | 50 | | |
| Exiguobacterium sibiricum | | 116 | | |
| Variovorax ginsengisoli | | 3078 | | |
| Pedobacter rhizosphaerae | | 598 | | |
| Duganella radicis | | 31 | | |
| Paenibacillus glycanilyticus | | 418 | | |
| Bacillus niacini | | 1718 | | |

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

REFERENCES

Ascend® plant growth regulator product sheet. EPA reg. No. 9776-335

Calvo, P., Nelson, L, Kloepper, J. W., 2014 Agricultural uses of plant biostimulants. Plant soil 383, 3-41.
"Chemistry and Technology of Agrochemical Formulation," edited by D. A. Knowles, copyright 1998 by Kluwer Academic Publishers.
Colby, R. S., "Calculating Synergistic and Antagonistic Responses of Herbicide Combinations, 1967 Weeds, vol. 15, pp. 20-22.
Current Protocols in Molecular Biology (F. M. Ausubel et al., eds., 1987).
Crameri et al. (1997) Nature Biotech. 15:436-438.
Crameri et al. (1998) Nature 391:288-291.
De Almeida et al., (1989) Mol. Gen. Genetics 218:78-86).
Fahraeus, G. (1957). *J. Gen Microbiol.* 16: 374-381.
Gerhardt, P. (ed.) Methods for General and Molecular Microbiology. American Society for Microbiology, Washington, D.C. (1994).
Gherna, 1Z. L. and C. A. Reddy. 2007. Culture Preservation, p 1019-1033. In C. A. Reddy, T. J. Beveridge, J. A. Breznak, G. A. Marzluf, T. M. Schmidt, and L. R. Snyder, eds. American Society for Microbiology, Washington, D.C., 1033 pages.
Innis et al., eds. (1990) PCR Protocols: A Guide to Methods and Applications (Academic Press, New York),
Innis and Gelfand, eds. (1995) PCR Strategies (Academic Press, New York).
In re Bergstrom, 427 F.2d 1394, (CCPA 1970),
In re Bergs, 596 F.2d 952 (CCPA 1979).
Jones et al., (1985) EMBO J. 4:2411-2418.
Lennette, E. H. (ed.) Manual of Clinical Microbiology, Third Edition. American Society for Microbiology, Washington, D.C. (1980).
*McCutcheon's Detergents and Emulsifiers Annual*, MC Publishing Corp., Ridgewood, N.J., 1998, and in *Encyclopedia of Surfactants*, Vol. Chemical Publishing Co., New York, 1980-81.
McCutcheon's, vol. 1, "Emulsifiers and Detergents," MC Publishing Company, Glen Rock, N.J., USA, 1996.
Merck & Co. v. Olin Mathieson Chemical Corp., 253 F.2d 156 (4th Cir. 1958).
Miche, L and Balandreau, J (2001). Effects of rice seed surface sterilisation with hypochlorite on inoculated *Burkolderia vietamiensis*. *Appl. Environ. Microbiol.* 67(7): p 3046-3052.
Moore et al. (1997) J. Mol. Biol. 272:336-347.
N-Large™ plant growth regulator product sheet. EPA Reg. No. 57538-18.
Parke-Davis & Co. v. H.K. Mulford & Co., 189 F. 95 (S.D.N.Y. 1911).
PCT/NZ2012/000041, published on Sep. 20, 2012, as International Publication No. WO 2012125050 A1.
PCT/NZ2013/000171, published on Mar. 27, 2014, as International Publication No. WO 2014046553 A1.
Pikovskaya R I (1948). Mobilization of phosphorus in soil connection with the vital activity of some microbial species. *Microbiologia* 17:362-370.
ProGibb® plant growth regulator product sheet. EPA Reg. No. 73049-15.
Release® plant growth regulator product sheet. EPA Reg. No. 73049-6.
Ruth Eckford, R., Cook, F. D., Saul, Aislabie J., and J. Foght (2002) Free-living Heterotrophic Bacteria Isolated from Fuel-Contaminated Antarctic Soils. *Appl. Environ. Microbiol* 68(10):5181.
RyzUp SmartGrass® plant growth regulator product sheet. EPA Reg. No. 73049-1.
Sambrook et al. (1989) Molecular Cloning: A Laboratory Manual (2nd ed., Cold Spring Harbor Laboratory Press, Plainview, N.Y.).
Stemmer (1994) Nature 370:389-391.
Stemmer (1994) PNAS 91:10747-10751,
Strobel G and Daisy B (2003) Microbiology and Molecular Biology Reviews 67 (4): 491-502.
U.S. Pat. No. 8,652,490 "Pasteuria Strain" issued Feb. 18, 2014.
U.S. Pat. No. 8,383,097 "Bacteria Cultures and Compositions Comprising Bacteria Cultures" issued Feb. 26, 2013.
Vandamme et al. 1996. Polyphasic taxonomy, a consensus approach to bacterial systematics. *Microbiol Rev* 1996, 60:407-438.
Bergey's Manual of Systematic Bacteriology $2^{nd}$ Edition Volume 1 (2001) The Archaea and the deeply branching and phototrophic Bacteria, Editor-in-Chief: George M. Garrity. Editors: David R. Boone and Richard W. Castenholz. ISBN 0-387-98771-1.
Bergey's Manual of Systematic Bacteriology $2^{nd}$ Edition Volume 2 (2005) The Proteobacteria. Editor-in-Chief: George M. Garrity, Editors: Don J. Brenner, Noel R. Krieg and James T. Staley. ISBN 0-387-95040-0.
Bergey's Manual of Systematic Bacteriology $2^{nd}$ Edition Volume 3 (2009) The Firmicutes. Editors: Paul De Vos, George Garrity, Dorothy Jones, Noel R. Krieg, Wolfgang Ludwig, Fred A. Rainey, Karl-Heinz Schleifer and William B. Whitman. ISBN 0-387-95041-9.
Bergey's Manual of Systematic Bacteriology $2^{nd}$ Edition Volume 4 (2011) The Bacteroidetes, Spirochaetes, Tenericutes (Mollicutes), Acidobacteria, Fibrobacteres, Fusobacteria, Dictyoglomi, Gemmatimonadetes, Lentisphaerae, Verrucomicrobia, Chlamydiae, and Planctomycetes. Editors: Noel R. Krieg, James T. Staley, Daniel R. Brown, Brian P. Hedlund, Bruce J. Paster, Naomi L. Ward, Wolfgang Ludwig and William B. Whitman. ISBN 0-387-95042-6
Bergey's Manual of Systematic Bacteriology $2^{nd}$ Edition Volume 5 (2012) The Actinobacteria. Editors: Michael Goodfellow, Peter Kampfer, Hans-Jurgen Busse, Martha E. Trujillo, Ken-ichiro Suzuki, Wolfgang Ludwig and William B. Whitman. ISBN 0-387-95042-7.
Yemm and Willis (Biochem. J. 1954, 57: 508-514).
X-CYTE™ plant growth regulator product sheet. EPA Reg. No. 57538-15.
Zhang et al. (1997) PNAS 94:4504-4509.
Zinniel D K et al. (2002) Applied and Environmental Microbiology 68 (5): 2198-2208).
Pikovskaya R I (1948), Mobilization of phosphorus in soil connection with the vital activity of some microbial species. *Microbiologia* 17:362-370.

What is claimed is:

1. A method of imparting at least one beneficial trait upon a plant species, the method comprising:
applying at least one isolated bacterial strain to a plant or to a growth medium having a plant, wherein growing the plant applied with the at least one bacterial strain exhibits an increased productivity as compared to a plant of the same species that is not applied with the at least one bacterial strain; wherein the at least one bacterial strain is selected from the group consisting of:
*Arthrobacter cupressi* deposited as NRRL Accession Deposit No. NRRL B-67183;
*Arthrobacter cupressi* deposited as NRRL Accession Deposit No. NRRL B-67184;
*Novosphingobium lindaniclasticum* deposited as NRRL Accession Deposit No. NRRL B-67201; and

*Novosphingobium lindaniclasticum* deposited as NRRL Accession Deposit No. NRRL B-67200; and wherein the at least one bacterial strain is heterologous to the plant.

2. The method of claim 1, wherein the applying comprises applying a microbial consortia comprising at least two of the isolated bacterial strains.

3. The method of claim 1, wherein the applying occurs by: coating a plant seed with said bacteria, coating a plant part with said bacteria, spraying said bacteria onto a plant part, spraying said bacteria into a furrow into which a plant or seed will be placed, drenching said bacteria onto a plant part or into an area into which a plant will be placed, spreading said bacteria onto a plant part or into an area into which a plant will be placed, broadcasting said bacteria onto a plant part or into an area into which a plant will be placed, combining the bacteria with a fertilizer or other agricultural composition and combinations thereof.

4. The method of claim 1, wherein the isolated bacterial strain is formulated in an agricultural composition with one or more of the following: an agriculturally acceptable carrier, a pesticide, a plant growth regulator, a beneficial agent or a biologically active agent.

* * * * *